US008501894B2

(12) United States Patent
Crowther et al.

(10) Patent No.: US 8,501,894 B2
(45) Date of Patent: Aug. 6, 2013

(54) HYDROSILYATION OF VINYL MACROMERS WITH METALLOCENES

(75) Inventors: Donna J. Crowther, Seabrook, TX (US); Jacqueline A. Lovell, Houston, TX (US); Patrick Brant, Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 157 days.

(21) Appl. No.: 13/072,305

(22) Filed: Mar. 25, 2011

(65) Prior Publication Data

US 2012/0245300 A1    Sep. 27, 2012

(51) Int. Cl.
*C08G 77/12* (2006.01)

(52) U.S. Cl.
USPC .......................................................... 528/31

(58) Field of Classification Search
USPC .......................................................... 528/31
See application file for complete search history.

(56) References Cited

U.S. PATENT DOCUMENTS

| | | | |
|---|---|---|---|
| 3,022,305 A | 2/1962 | Carboni | |
| 3,235,484 A | 2/1966 | Colfer | |
| 4,069,023 A | 1/1978 | Brois et al. | |
| 4,110,377 A | 8/1978 | Clerici et al. | |
| 4,197,398 A | 4/1980 | Floyd et al. | |
| 4,619,756 A | 10/1986 | Dickakian | |
| 4,814,540 A | 3/1989 | Watanabe et al. | |
| 4,973,414 A | 11/1990 | Nerger et al. | |
| 4,988,764 A | 1/1991 | Nishio et al. | |
| 5,026,948 A | 6/1991 | Forbus | |
| 5,049,535 A | 9/1991 | Resconi et al. | |
| 5,211,834 A | 5/1993 | Forester | |
| 5,229,022 A | 7/1993 | Song et al. | |
| 5,252,677 A | 10/1993 | Tomita et al. | |
| 5,266,186 A | 11/1993 | Kaplan | |
| 5,382,634 A | 1/1995 | Koyama et al. | |
| 5,439,607 A | 8/1995 | Patil | |
| 5,444,125 A | 8/1995 | Tomita et al. | |
| 5,498,809 A | 3/1996 | Emert et al. | |
| 5,504,172 A | 4/1996 | Imuta et al. | |
| 5,705,577 A | 1/1998 | Rossi et al. | |
| 5,741,946 A | 4/1998 | Wei | |
| 5,744,541 A | 4/1998 | Sawaguchi et al. | |
| 5,750,815 A | 5/1998 | Grubbs et al. | |
| 5,756,428 A | 5/1998 | Emert et al. | |
| 5,811,379 A | 9/1998 | Rossi et al. | |
| 5,859,159 A | 1/1999 | Rossi et al. | |
| 5,936,041 A | 8/1999 | Diana et al. | |
| 6,017,859 A | 1/2000 | Rossi et al. | |
| 6,114,445 A | 9/2000 | Tzoganakis et al. | |
| 6,117,962 A | 9/2000 | Weng et al. | |
| 6,143,686 A | 11/2000 | Vizzini et al. | |
| 6,197,910 B1 | 3/2001 | Weng et al. | |
| 6,225,432 B1 | 5/2001 | Weng et al. | |
| 6,255,426 B1 | 7/2001 | Lue et al. | |
| 6,268,518 B1 | 7/2001 | Resconi et al. | |
| 6,410,666 B1 | 6/2002 | Grubbs et al. | |
| 6,444,773 B1 | 9/2002 | Markel | |
| 6,448,350 B1 | 9/2002 | Dall'Occo et al. | |
| 6,476,167 B2 | 11/2002 | Peters | |
| 6,525,157 B2 | 2/2003 | Cozewith et al. | |
| 6,703,457 B2 | 3/2004 | Van Baar et al. | |
| 6,750,307 B2 | 6/2004 | Weng et al. | |
| 6,897,261 B1 | 5/2005 | Machida et al. | |
| 6,939,930 B2 | 9/2005 | Reinking et al. | |
| 7,126,031 B2 | 10/2006 | Boussie et al. | |
| 7,247,385 B1 | 7/2007 | Tzoganakis et al. | |
| 7,276,567 B2 | 10/2007 | Voskoboynikov et al. | |
| 7,294,681 B2 | 11/2007 | Jiang et al. | |
| 7,524,910 B2 | 4/2009 | Jiang et al. | |
| 7,541,413 B2 | 6/2009 | Crowther et al. | |
| 7,589,160 B2 | 9/2009 | Resconi et al. | |
| 7,790,810 B2 | 9/2010 | Coates et al. | |
| 7,820,607 B2 | 10/2010 | Matsuda et al. | |
| 7,897,679 B2 | 3/2011 | Stevens et al. | |
| 7,943,716 B2 | 5/2011 | Resconi et al. | |
| 7,960,487 B2 | 6/2011 | Yang et al. | |
| 8,058,351 B2 | 11/2011 | Pawlow et al. | |
| 2002/0037408 A1 * | 3/2002 | Tsutsui et al. | 428/373 |
| 2002/0137978 A1 | 9/2002 | Grubbs et al. | |
| 2003/0161752 A1 | 8/2003 | Luk et al. | |
| 2004/0054086 A1 | 3/2004 | Schauder et al. | |
| 2004/0127649 A1 | 7/2004 | Arjunan | |
| 2004/0214953 A1 | 10/2004 | Yamada et al. | |
| 2004/0249046 A1 | 12/2004 | Abhari et al. | |

(Continued)

FOREIGN PATENT DOCUMENTS

| | | |
|---|---|---|
| CN | 101011062 | 8/2007 |
| EP | 0 767 182 | 4/1997 |

(Continued)

OTHER PUBLICATIONS

Bulgakova et al., "Organosilicon hydrides in macromolecular design: Reactions of chain-transfer and hydrosilylation" European Polymer Journal (2007) 43(2) 644-651.*
Britovsek et al., *Novel Olefin Polymerization Catalysts Based on Iron and Cobalt*, Chemical Communications, 1998, No. 7, pp. 849-850.
Britovsek et al., *Iron and Cobalt Ethylene Polymerization Catalysts Bearing 2,6-Bis(Imino)Pyridyl Ligands: Synthesis, Structures, and Polymerization Studies*, Journal of the American Chemical Society, 1999, vol. 121, No. 38, pp. 8728-8740.
Chen et al., *Preparation of Epoxy-modified Polyethylene by Graft Extrusion and its Applications to Polyphenylene Sulfide Alloys as a Compatibilizer*, Reactive & Functional Polymers, 2008, vol. 68, No. 9, pp. 1307-1313.
Cossy et al., "Cross-Metathesis reaction. Generation of Highly Functionalized Olefins from Unsaturated Alcohols", Journal of Organometallic Chemistry, 2001, vol. 634, Issue 2, pp. 216-221.
Hansell et al., *Additive-Free Clicking for Polymer Functionalization and Coupling by Tetrazine-Norbornene Chemistry*, Journal of the American Chemical Society, 2011, vol. 133, No. 35, pp. 13828-13831.
Liu et al., *Kinetics of Initiation, Propagation, and Termination for the [rac-(C2H4(1-indenyl)2)ZrMe]{MeB(C6F5)3}-Catalyzed Polymerization of 1-Hexene*, Journal of the American Chemical Society, 2001, vol. 123, pp. 11193-11207.

(Continued)

*Primary Examiner* — Kuo-Liang Peng

(74) *Attorney, Agent, or Firm* — Kevin M. Faulkner; Catherine L. Bell

(57) ABSTRACT

This invention relates to a process to functionalize polyolefins comprising contacting a metallocene catalyst with a hydrosilane, and one or more vinyl terminated polyolefins. This invention further relates to the hydrosilane-functionalized polyolefins produced thereby.

5 Claims, 4 Drawing Sheets

U.S. PATENT DOCUMENTS

| | | | |
|---|---|---|---|
| 2005/0054793 A1 | 3/2005 | Reinking et al. |
| 2005/0159299 A1 | 7/2005 | Rodriguez et al. |
| 2005/0261440 A1 | 11/2005 | Dickakian et al. |
| 2006/0052553 A1 | 3/2006 | Resconi et al. |
| 2006/0270814 A1 | 11/2006 | Mako et al. |
| 2007/0293640 A1 | 12/2007 | Jiang et al. |
| 2008/0228017 A1 | 9/2008 | Burdett et al. |
| 2008/0234451 A1 | 9/2008 | Kenwright et al. |
| 2009/0198089 A1 | 8/2009 | Burton et al. |
| 2009/0221750 A1 | 9/2009 | Tsunogae et al. |
| 2009/0247441 A1 | 10/2009 | Baum |
| 2009/0318640 A1 | 12/2009 | Brant et al. |
| 2009/0318644 A1 | 12/2009 | Brant et al. |
| 2009/0318646 A1 | 12/2009 | Brant et al. |
| 2009/0318647 A1 | 12/2009 | Hagadorn et al. |
| 2010/0069573 A1 | 3/2010 | Arriola et al. |
| 2010/0152388 A1 | 6/2010 | Jiang et al. |
| 2010/0170829 A1 | 7/2010 | Ng et al. |

FOREIGN PATENT DOCUMENTS

| | | |
|---|---|---|
| EP | 0 802 216 | 10/1997 |
| EP | 0 958 309 | 11/1999 |
| EP | 1 361 232 | 11/2003 |
| EP | 1 849 757 | 10/2007 |
| EP | 1 862 491 | 12/2007 |
| GB | 1 310 847 | 3/1973 |
| JP | 02-064115 | 3/1990 |
| JP | 1993/320260 | 12/1993 |
| JP | 2000/038420 | 2/2000 |
| JP | 2005/139284 | 6/2005 |
| JP | 2005-336092 | 12/2005 |
| JP | 2007/169340 | 7/2007 |
| JP | 2007/246433 | 9/2007 |
| JP | 2008/050278 | 3/2008 |
| JP | 2009-299046 | 12/2009 |
| JP | 2010/037555 | 2/2010 |
| JP | 2010-202628 | 9/2010 |
| JP | 2011/026448 | 2/2011 |
| JP | 2012/051859 | 3/2012 |
| JP | 2012/052062 | 3/2012 |
| WO | WO 95/27717 | 10/1995 |
| WO | WO 97/47665 | 12/1997 |
| WO | WO 99/05182 | 2/1999 |
| WO | WO 99/46270 | 9/1999 |
| WO | WO 00/00576 | 1/2000 |
| WO | WO 00/55218 | 9/2000 |
| WO | WO 03/040095 | 5/2003 |
| WO | WO 03/040233 | 5/2003 |
| WO | WO 03/040442 | 5/2003 |
| WO | WO 2004/031250 | 4/2004 |
| WO | WO 2004/046214 | 6/2004 |
| WO | WO 2005/090425 | 9/2005 |
| WO | WO 2005/090426 | 9/2005 |
| WO | WO 2005/090427 | 9/2005 |
| WO | WO 2005/092935 | 10/2005 |
| WO | WO 2006/127483 | 11/2006 |
| WO | WO 2007/003238 | 1/2007 |
| WO | WO 2008/027268 | 3/2008 |
| WO | WO 2008/080081 | 7/2008 |
| WO | WO 2008/141941 | 11/2008 |
| WO | WO 2009/009158 | 1/2009 |
| WO | WO 2009/155517 | 12/2009 |
| WO | WO 2010/037059 | 4/2010 |

OTHER PUBLICATIONS

Nagai et al., *Novel Well-defined Funcationalized Polyolefins and Polyolefin-polar Polymer Block Copolymers: Formations and Their Features*, Poly Preprints, 2008, vol. 49, No. 2, 776-777.

Nakatsuka et al., *Creation and Application of New Materials by a Fusion of FI-catalyst Technology and Fine Organic Synthesis Technology*, Shokubai, 2010, vol. 52, No. 8, pp. 569-574.

Rodriguez et al., *Poly(4-vinylpyridazine). First Synthesis, Characterization and Properties*, Polymeric Materials Science and Engineering, Proceedings of the ACS Division of Polymeric Materials Science and Engineering, 1990, vol. 63, pp. 376-382 (Abstract).

Shiono et al., *Copolymerization of poly(propylene) macromonomer with ethylene by (tertbutanamide)dimethyl(tetramethyl-qscyclopentadienyl) silane titanium dichloride/methylaluminoxane catalyst*, Macromol. Chem. Phys., 1997, vol. 198, pp. 3229-3237.

Weng et al., *Synthesis of Long-Chain Branched Propylene Polymers via Macromonomer Incorporation*, Macromol. Rapid Commun., 2001, vol. 22, No. 18, pp. 1488-1492.

Xu et al., *Ethylene Copolymerization with 1-Octene Using a 2-Methylbenz[e]indenyl-Based ansa-Monocyclopentadienylamido Complex and Methylaluminoxane Catalyst*, Macromolecules, 1998, vol. 31, pp. 4724-4729.

Balboni et al., $C_2$-Symmetric Zirconocenes for High Molecular Weight Amorphous Poly(propylene), Macromolecular Chemistry and Physics, 2001, vol. 202, No. 10, pp. 2010-2028.

Brzezinska et al., "*Synthesis of ABA Triblock Copolymers via Acyclic Diene Metathesis Polymerization and Living Polymerization of α-Amino Acid-N-Carboxyanhydrides*", Macromolecules, 2001, vol. 34, pp. 4348-4354.

Bujadoux et al., *Use of Bridged and Non-bridged Metallocene Catalysts in High Pressure/High Temperature Ethylene/α-olefin Copolymerization*, Metallocene Polymers, 1995, pp. 377-402.

Koo et al., "*Silicon-Modified Ziegler-Natta Polymerization. Catalytic Approaches to Silyl-Capped and Silyl-Linked Polyolefins Using "Single-Site" Cationic Ziegler-Natta Catalysts*", JACS, 1999, vol. 121, pp. 8791-8802.

Passaglia et al., "*Grafting of Diethyl Maleate and Maleic Anhydride Onto Styrene-b-(Ethylene-co-1-Butene)-b-Styrene Triblock Copolymer (SEBS)*", Polymer, 2000, vol. 41, pp. 4389-4400.

Quirk et al., "*Anionic Synthesis of Secondary Amine Functionalized Polymers by Reaction of Polymeric Organolithiums with N-Benzylidenemethylamine*", Macromolecular Chemistry and Physics, 2002, vol. 203, pp. 1178-1187.

Rybak et al., "*Acyclic Diene Metathesis with a Monomer with a Monomer from Renewable Resources: Control of Molecular Weight and One-Step Preparation of Block Copolymers*", ChemSusChem, 2008, vol. 1, pp. 542-547.

Amin et al., "*Versatile Pathways for In Situ Polyolefin Functionalization with Heteroatoms: Catalytic Chain Transfer*", Angewandte Chemie International Edition, 2008, vol. 47, pp. 2006-2025.

Ayinla et al., "Chiral Tantalum and Zironium Biphenyl Amidate Complexes: New Catalysts for the Assymetric Synthesis of Amines", Abstracts of Papers, 238th ACS National Meeting, Washington DC, United States, Aug. 16-20, 2009, INOR-252.

Babu et al., "*Microstructure of Poly(1-hexene) Produced by ansa-Zirconocenium Catalysis*", Macromolecules, 1994, vol. 27, pp. 3383-3388.

Baldwin et al., "*Cationic Alkylaluminum-Complexed Zirconocene Hydrides as Participants in Olefin Polymerization Catalysis*", JACS, 2010, vol. 132, pp. 13969-13971.

Bhriain et al., "*Polymeryl-Exchange Between Ansa-Zirconocene Catalysts for Norbornene-Ethene Copolymerization and Aluminum or Zinc Alkyls*", Macromolecules, 2005, vol. 38, pp. 2056-2063.

Bielawski et al., "*Synthesis of ABA Triblock Copolymers Via a Tandem Ring-Opening Metathesis Polymerization: Atom Transfer Radical Polymerization Approach*", Macromolecules, 2000, vol. 33, pp. 678-680.

Brant et al., "*Effect of Tacticity on the Dilute Solution Coil Dimensions of Poly(α-olefin)s*", Macromolecules, 2005, vol. 38, pp. 7178-7183.

Cherian et al., "*Synthesis of Allyl-Terminated Syndiotactic Polypropylene: Macromonomers for the Synthesis of Branched Polyolefins*", Macromolecules, 2005, vol. 38, pp. 6259-6268.

Chung, "*Synthesis of Functional Polyolefin Copolymers with Graft and Block Structures*", Progress in Polymer Science, 2002, vol. 27, pp. 39-85.

Clerici et al., "*Catalytic C-Alkylation of Secondary Amines With Alkenes*", Synthesis, 1980, vol. 4, pp. 305-306.

Corey et al., "*Reactions of Hydrosilanes and Olefins in the Presence of $Cp_2MCl_2/nBuLi$*", Organometallics, 1992, vol. 11, pp. 672-683.

Crowther et al., "*Group 4 Metal Dicarbollide Chemistry. Synthesis, Structure, and Reactivity of Electrophilie Alkyl Complexes $(Cp^*)(C2B9H_{11})M(R)$ (M = Hf, Zr)*", JACS, 1991, vol. 113, pp. 1455-1457.

Eisenberger et al., "*Tantalum-amidate Complexes for the Hydroaminoalkylation of Secondary Amines: Enhanced Substrate*

Scope and Enantioselective Chiral Amine Synthesis", Angewandte Chemie International Edition, 2009, vol. 48, pp. 8361-8365.

Eshuis et al., "Catalytic Olefin Oligomerization and Polymerization with Cationic Group IV Metal Complexes [Cp*$_2$Mme(THT)]$^+$ [BPh$_4$]$^-$, M=Ti, Zr and Hf", Journal of Molecular Catalysis, 1990, vol. 62, pp. 277-287.

Frauenrath et al., "Polymerization of 1-Hexene Catalyzed by Bis(Cyclopentadienyl)Zirconium Dichloride/Methylaluminoxane; Effect of Temperature on the Molecular Weight and the Microstructure of Poly(1-Hexene)", Macromol. Rapid Commun., 1998, vol. 19, pp. 391-395.

Furuyama et al., "New High-Performance Catalysts Developed at Mitsui Chemicals for Polyolefins and Organic Synthesis", Catalysis Surveys from Asia, 2004, vol. 8, No. 1, pp. 61-71.

Galeotti et al., "Self-Functionalizing Polymer Film Surfaces Assisted by Specific Polystyrene End-Tagging",Chem. Mater., 2010, vol. 22, pp. 2764-2769.

Harney et al., "End-Group-Confined Chain Walking Within a Group 4 Living Polyolefin and Well-Defined Cationic Zirconium Alkyl Complexes for Modeling This Behavior", JACS, 2004, vol. 126, pp. 4536-4537.

Herzon et al., "Direct, Catalytic Hydroaminoalkylation of Unactivated Olefins with N-Alkyl Arylamines", JACS, 2007, vol. 129, pp. 6690-6691.

Herzon et al., "Hydroaminoalkylation of Unactivated Olefins with Dialkylamines", JACS, 2007, vol. 130, pp. 14940-14941.

Janiak et al., "Analyses of Propene and 1-Hexene Oligomers from Zirconium/MAO Catalysts—Mechanistic Implications by NMR, SEC, and MALDI-TOF MS", Macromol. Chem. Phys., 2002, vol. 203, pp. 129-138.

Janiak et al., "Metallocene Catalysts for Olefin Oligomerization", Macromol. Symp., 2006, vol. 236, pp. 14-22.

Janiak et al., "Metallocene and Related Catalysts for Olefin, Alkyne and Silane Dimerization and Oligomerization", Coordination Chemistry Reviews, 2006, vol. 250, pp. 66-94.

Jiang et al., "Highly Z-Selective Metathesis Homocoupling of Terminal Olefins", JACS, 2009, vol. 131, pp. 16630-16631.

Jones et al., "Synthesis and Reactive Blending of Amine and Anhydride End-Functional Polyolefins", Polymer, 2004, vol. 45, pp. 4189-4201.

Kaneyoshi et al., "Synthesis of Block and Graft Copolymers with Linear Polyethylene Segments by Combination of Degenerative Transfer Coordination Polymerization and Atom Transfer Radical Polymerization", Macromolecules, 2005, vol. 38, pp. 5425-5435.

Kesti et al., "Group 4 Metallocene Olefin Hydrosilyation Catalysts", Organometallics, 1992, vol. 11, pp. 1095-1103.

Kissin et al., "Post-Oligomerization of α-Olefin Oligomers: A Route to Single-Component and Multipcomponent Synthetic Lubricating Oils", Journal of Applied Polymer Science, 2009, vol. 111, pp. 273-280.

Kobayashi, "Routes to Functionalized Polyolefins", The Dow Chemical Company.

Kolodka et al., "Synthesis and Characterization of Long-Chain-Branched Polyolefins with Metallocene Catalysts: Copolymerization of Ethylene with Poly(Ethylene-Co-Propylene) Macromonomer", Macromol. Rapid Commun., 2003, vol. 24, pp. 311-315.

Koo et al., "Efficient New Routes to Functionalized Polyolefins", ChemTech. 1999, pp. 13-19.

Kostalik et al., "Solvent Processable Tetraalkylammonium-Functionalized Polyethylene for Use as an Alkaline Anion Exchange Membrane", Macromolecules, 2010, vol. 43, pp. 7147-7150.

Kubiak et al., "Titanium-Catalyzed Hydroaminoalkylation of Alkenes by C-H Bond Activation at SP3 Centers in the Alpha-Position to a Nitrogen Atom", Angewandte Chemie International Edition, 2009, vol. 48, No. 6, pp. 1153-1156.

Langston et al., "One-Pot Synthesis of Long Chain Branch PP (LCBPP) Using Ziegler-Natta Catalyst and Branching Reagents", Macromol. Symp., 2007, vol. 260, pp. 34-41.

Lehmus et al., "Chain End Isomerization as a Side Reaction in Metallocene-Catalyzed Ethylene and Propylene Polymerizations", Macromolecules, 2000, vol. 33, pp. 8534-8540.

Lopez et al., "Synthesis of Well-Defined Polymer Architectures by Successive Catalytic Olefin Polymerization and Living/Controlled Polymerization Reactions", Progress in Polymer Science, 2007, vol. 32, pp. 419-454.

Lu et al., "Reactivity of Common Functional Groups with Urethanes: Models for Reactive Compatibilization of Thermoplastic Polyurethane Blends", Journal of Polymer Science: Part A: Polymer Chemistry, 2002, vol. 40, pp. 2310-2328.

Markel et al., "Metallocene-Based-Branch—Block Thermoplastic Elastomers", Macromolecules, 2000, vol. 33, pp. 8541-8548.

Mathers et al., "Cross Metathesis Functionalization of Polyolefins", Chem. Commun., 2004, pp. 422-423.

Moscardi et al., "Propene Polymerization with the Isospecific, Highly Regioselective rac-Me$_2$C(3-t-Bu-1-Ind)2/ZrCl$_2$/MAO Catalyst. 2. Combined DFT/MM Analysis of Chain Propagation and Chain Release Reactions", Organometallics, 2001, vol. 20, pp. 1918-1931.

Negishi et al., "Reaction of Zirconocene Dichloride with Alkyllithiums or Alkyl Grignard Reagents as a Convenient Method for Generating a "Zirconocene" Equivalent and its Use in Zirconium-Promoted Cyclization of Alkenes, Alkynes, Dienes, Enynes, and Diynes[1]", Tetrahedron Letters, 1986, vol. 27, No. 25, pp. 2829-2832.

Nilsson et al., "Structural Effects on Thermal Properties and Morphology in XLPE", European Polymer Journal, 2010, vol. 46, pp. 1759-1769.

Ornealis et al., "Cross Olefin Metathesis for the Selective Functionalization, Ferrocenylation, and Solubilization in Water of Olefin-Terminated Dendrimers, Polymers, and Gold Nanoparticles and for a Divergent Dendrimer Construction", JACS, 2008, vol. 130, pp. 1495-1506.

Ornealis et al., "Efficient Mono- and Bifunctionalization of Polyolefin Dendrimers by Olefin Metathesis", Angewandte Chemie International Edition, 2005, vol. 44, pp. 7399-7404.

Parks et al., "Studies on the Mechanism of B(C$_6$F$_5$)$_3$-Catalyzed Hydrosilation of Carbonyl Functions", J. Org. Chem., 2000, vol. 65, pp. 3090-3098.

Prochnow et al., "Tetrabenzyltitanium: An Improved Catalyst for the Activation of SP3 C-H Bonds Adjacent to Nitrogen Atoms", ChemCatChem, 2009, vol. 1, No. 1, pp. 162-172.

Resconi et al., "Chain Transfer Reactions in Propylene Polymerization with Zirconocene Catalysts", Topics in Catalysis, 1999, vol. 7, pp. 145-163.

Resconi et al., "Olefin Polymerization at Bis(pentamethylcyclopentadienyl)zirconium and —hafnium Centers: Chain-Transfer Mechanisms", JACS, 1992, vol. 114, pp. 1025-1032.

Reznichenko et al., "Group 5 Metal Binapthalate Complexes for Catalytic Asymmetric Hydroaminoalkylation and Hydroamination/Cyclization", Organometallics, 2011, vol. 30, pp. 921-924.

Roesky, "Catalytic Hydroaminoalkylation", Angewandte Chemie International Edition, 2009, vol. 48, pp. 4892-4894.

Rose et al., "Poly(Ethylene-Co-Propylene Macromonomer)s: Synthesis and Evidence for Starlike Conformations in Dilute Solution", Macromolecules, 2008, vol. 41, pp. 559-567.

Rossi et al., "End Groups in 1-Butene Polymerization Via Methylaluminoxane and Zirconocene Catalyst", Macromolecules, 1995, vol. 28, pp. 1739-1749.

Rulhoff et al., "Synthesis and Characterization of Defined Branched Poly(propylene)s with Different Microstructures by Copolymerization of Propylene and Linear Ethylene Oligomers ($C_n$=26-28) with Metallocenes/MAO Catalysts", Macromolecules, 2006, vol. 16, pp. 1450-1460.

Scherman et al., "Synthesis and Characterization of Stereoregular Ethylene-Vinyl Alcohol Copolymers Made by Ring-Opening Metathesis Polymerization", Macromolecules, 2005, vol. 38, pp. 9009-9014.

Seayed et al., "Hydroaminomethylation of Olefins Using a Rhodium Carbene Catalyst", Tetrahedron Letters, 2003, vol. 44, No. 8, pp. 1679-1683.

Segawa et al., "Catalytic Hydroaminoalkylation of Alkene", Yuki Gosei Kagaku Kyokaishi, 2009, vol. 67, No. 8, pp. 834-844. (Abstract only).

Shiono et al., "*Additive Effects of Trialkylaluminum on Propene Polymerization with (t-BuNSiMe₂Flu)TiMe₂-Based Catalysts*", Applied Catalysis A: General, 2000, vol. 200, pp. 145-152.

Shiono et al., "*Copolymerization of Atactic Polypropene Macromonomer with Propene by an Isospecific Metallocene Catalyst*", Macromolecules, 1999, vol. 32, pp. 5723-5727.

Sill et al., "*Bis-Dendritic Polyethylene Prepared by Ring-Opening Metathesis Polymerization in the Presence of Bis-Dendritic Chain Transfer Agents*", Journal of Polymer Science: Part A: Polymer Chemistry, 2005, vol. 43, pp. 5429-5439.

Small et al., "*Polymerization of Propylene by a New Generation of Iron Catalysts: Mechanisms of Chain Initiation, Propagation, and Termination*", Macromolecules, 1999, vol. 32, pp. 2120-2130.

Stadler et al., "*Long-Chain Branches in Syndiotactic Polypropene Induced by Vinyl Chloride*", Macromolecular Chemistry and Physics, 2010, vol. 211, pp. 1472-1481.

Sun et al., "*Effect of Short Chain Branching on the Coil Dimensions of Polyolefins in Dilute Solution*", Macromolecules, 2001, vol. 34, pp. 6812-6820.

Sunderhaus et al., "*Oxidation of Carbon-Silicon Bonds: The Dramatic Advantage of Strained Siletanes*", Organic Letters, 2003, vol. 5, No. 24, pp. 4571-4573.

Switek et al., "*ABA Triblock Copolymers with a Ring-Opening Metathesis Polymerization/Macromolecular Chain-Transfer Agent Approach*", Journal of Polymer Science: Part A: Polymer Chemistry, 2007, vol. 45, pp. 361-373.

Thomas et al., "*Synthesis of Telechelic Polyisoprene via Ring-Opening Metathesis Polymerization in the Presence of Chain Transfer Agent*", Macromolecules, 2010, vol. 43, pp. 3705-3709.

Wei et al., "*Aufbaureaktion Redux: Scalable Production of Precision Hydrocarbons from AlR₃ (R=Et or iBu) by Dialkyl Zinc Mediated Ternary Living Coordinative Chain-Transfer Polymerization*", Angewandte Chemie Inernational Edition, 2010, vol. 49, pp. 1768-1772.

Weng et al., "*Long Chain Branched Isotactic Polypropylene*", Macromolecules, 2002, vol. 35, pp. 3838-3843.

Weng et al., "*Synthesis of Vinly-Terminated Isotactic Poly(Propylene)*", Macromol. Rapid Commun., 2000, vol. 21, pp. 1103-1107.

Yang et al., "*Catatonic Metallocene Polymerization Catalysts, Synthesis and Properties of the First Base-Free Zirconocene Hydride*", Angewandte Chemie International Edition Engl., 1992, vol. 31, pp. 1375-1377.

Yin et al., "*Scope and Mechanism of Allylic C-H Amination of Terminal Alkenes by the Palladium/PhL(OPiv)₂ Catalyst System: Insights into the Effect of Naphthoquinone*", JACS, 2010, vol. 132, pp. 11978-11987.

Zhang et al., "*Functionalization of Polyolefins Through Catalytic Hydrosilylation and Imidation Reactions*", ANTEC, 2005, pp. 2686-2690.

\* cited by examiner

* = Ph-Si and Si-H resonances

HYDROSILYATION OF VINYL MACROMERS WITH METALLOCENES

RELATED APPLICATIONS

This application is related to U.S. Ser. No. 12/143,663, filed on Jun. 20, 2008 (Published as WO 2009/155471); U.S. Ser. No. 12/487,739, filed on Jun. 19, 2009 (Published as WO 2009/155472); U.S. Ser. No. 12/488,066, filed on Jun. 19, 2009 (Published as WO 2009/155510); 12/488,093, filed on Jun. 19, 2009 (Published as WO 2009/155517); and U.S. Ser. No. 12/642,453, filed Dec. 18, 2009; which is a continuation-in-part application of U.S. Ser. No. 12/533,465 filed on Jul. 31, 2009, which claims priority to and the benefit of U.S. Ser. No. 61/136,172, filed on Aug. 15, 2008; which are all incorporated by reference herein.

This invention also relates to the following concurrently filed applications:

a) U.S. Ser. No. 13/072,280, filed Mar. 25, 2011, entitled "Novel Catalysts and Methods of Use Thereof to Produce Vinyl Terminated Polymers";

b) U.S. Ser. No. 13/072,189, filed Mar. 25, 2011, entitled "Amine Functionalized Polyolefin and Methods for Preparation Thereof";

c) U.S. Ser. No. 13/072,279, filed Mar. 25, 2011, entitled "Enhanced Catalyst Performance for Production of Vinyl Terminated Propylene and Ethylene/Propylene Macromers";

d) U.S. Ser. No. 13/072,383, filed Mar. 25, 2011, entitled "Diblock Copolymers Prepared by Cross Metathesis";

e) U.S. Ser. No. 13/072,261, filed Mar. 25, 2011, entitled "Amphiphilic Block Polymers Prepared by Alkene Metathesis";

f) U.S. Ser. No. 13/072,288, filed Mar. 25, 2011, entitled "Vinyl Terminated Higher Olefin Polymers and Methods to Produce Thereof";

g) U.S. Ser. No. 13/072,330, filed Mar. 25, 2011, entitled "Block Copolymers from Silylated Vinyl Terminated Macromers";

h) U.S. Ser. No. 13/072,249, filed Mar. 25, 2011, entitled "Vinyl Terminated Higher Olefin Copolymers and Methods to Produce Thereof"; and i) U.S. Ser. No. 61/467,681, filed Mar. 25, 2011, entitled "Branched Vinyl Terminated Polymers and Methods for Production Thereof".

FIELD OF THE INVENTION

This invention relates to functionalization of vinyl terminated polyolefins by hydrosilylation reactions with a metallocene.

BACKGROUND OF THE INVENTION

Methods for the production of polyolefins with end-functionalized groups are typically multi-step processes that often create unwanted by-products and waste of reactants and energy. For reviews of methods to form end-functionalized polyolefins, see: (a) S. B. Amin and T. J. Marks *Angew. Chem. Int. Ed.* 2008, 47, 2006-2025; (b) T. C. Chung *Prog. Polym. Sci.* 2002, 27, 39-85; (c) R. G. Lopez, F. D'Agosto, C. Boisson *Prog. Polym. Sci.* 2007, 32, 419-454. A process with a reduced number of steps, even one step, would be desirable.

U.S. Pat. No. 4,110,377 discloses secondary aliphatic amines alkylated with alpha-olefins, such as ethylene, propylene, hexene, and undecene. Likewise, several literature references disclose hydroaminoalkylation of olefins using various catalysts (see J. Am. Chem. Soc. 2008, 130, 14940-14941; J. Am. Chem. Soc. 2007, 129, 6690-6691; Angew. Chem. Int. Ed. 2009, 48, 8361-8365; Angew. Chem. Int. Ed. 2009, 48, 4892-4894; *Yuki Gosei Kagaku Kyokaishi* (2009), 67(8), 843-844; *Angewandte Chemie, International Edition* (2009), 48(6), 1153-1156; *Tetrahedron Letters* (2003), 44(8), 1679-1683; *Synthesis* (1980), (4), 305-306). Corey discloses low molecular weight olefins treated with hydrosilanes in the presence of $Cp_2MCl_2$ and n-BuLi to prepare low molecular weight hydrosilylated products.

None of the above references however disclose functionalization of polyolefins, particularly polyolefins having Mn's over 200 g/mol, more particularly over 500 g/mol having large amounts of vinyl terminal groups.

U.S. Ser. No. 12/487,739, filed Jun. 19, 2009 discloses certain vinyl terminated oligomers and polymers that are functionalized for use in lubricant applications.

U.S. Ser. No. 12/143,663, filed on Jun. 20, 2008 discloses certain vinyl terminated oligomers and polymers that are functionalized in U.S. Ser. No. 12/487,739, filed Jun. 19, 2009.

U.S. Ser. No. 12/488,093, filed Jun. 19, 2009 discloses a process to functionalize propylene homo- or co-oligomer comprising contacting an alkene metathesis catalyst with a heteroatom containing alkene and a propylene homo- or co-oligomer having terminal unsaturation.

None of the above references however disclose functionalization of polyolefins, particularly polyolefins having Mn's over 500 g/mol having large amounts of vinyl terminal groups.

End-functionalized polyolefins that feature a chemically reactive or polar end group are of interest for use in a broad range of applications as compatibilizers, tie-layer modifiers, surfactants, and surface modifiers.

Thus, there is a need to develop a means to provide functionalized polyolefins (particularly end-functionalized) by efficient reactions, particularly reactions with good conversion, preferably under mild reaction conditions with a minimal number of steps, preferably one or two steps.

The instant invention's use of transition metal catalysts, such as metallocenes, to introduce hydrosilane groups is both a commercially economical and an "atom-economical" route to end functionalized polyolefins. Herein is described a novel method for their production by the reaction of vinyl-terminated polyolefins with hydrosilanes in the presence of a metallocene catalyst. This method is useful for a range of vinyl terminated polyolefins, including isotactic polypropylene (iPP), atactic polypropylene (aPP), ethylene propylene copolymer (EP), and polyethylene (PE).

SUMMARY OF THE INVENTION

This invention relates to a process to functionalize polyolefins (as used herein polyolefin is defined to include both polymers and oligomers) comprising contacting a metallocene catalyst with a hydrosilane, and one or more vinyl terminated polyolefins.

This invention further relates to hydrosilane-functionalized polyolefins, preferably represented by the formula: PO—Si(R*)$_m$H$_n$, PO—Si(R*)$_2$H, or PO—Si(R*)$_2$-L-Si(R**)$_2$H wherein m is 1 or 2; n is 1 or 2; m+n=3; PO is substituted or unsubstituted hydrocarbyl group having from 20 to about 10,000 carbon atoms; each R*, independently, is a H, or a $C_1$ to a $C_{20}$ substituted or unsubstituted hydrocarbyl group, where any two R* may form a cyclic structure with Si; L is a bond or a linking group; and each R, where any two R may form a cyclic structure with Si, independently, is a H, or a $C_1$ to a $C_{20}$ substituted or unsubstituted hydrocarbyl group.

The hydrosilylated product can be further converted to other moieties such as an —Si(R*)$_2$-OEt that would be useful to modify inorganic oxides such as silica.

DETAILED DESCRIPTION

Figure 1:
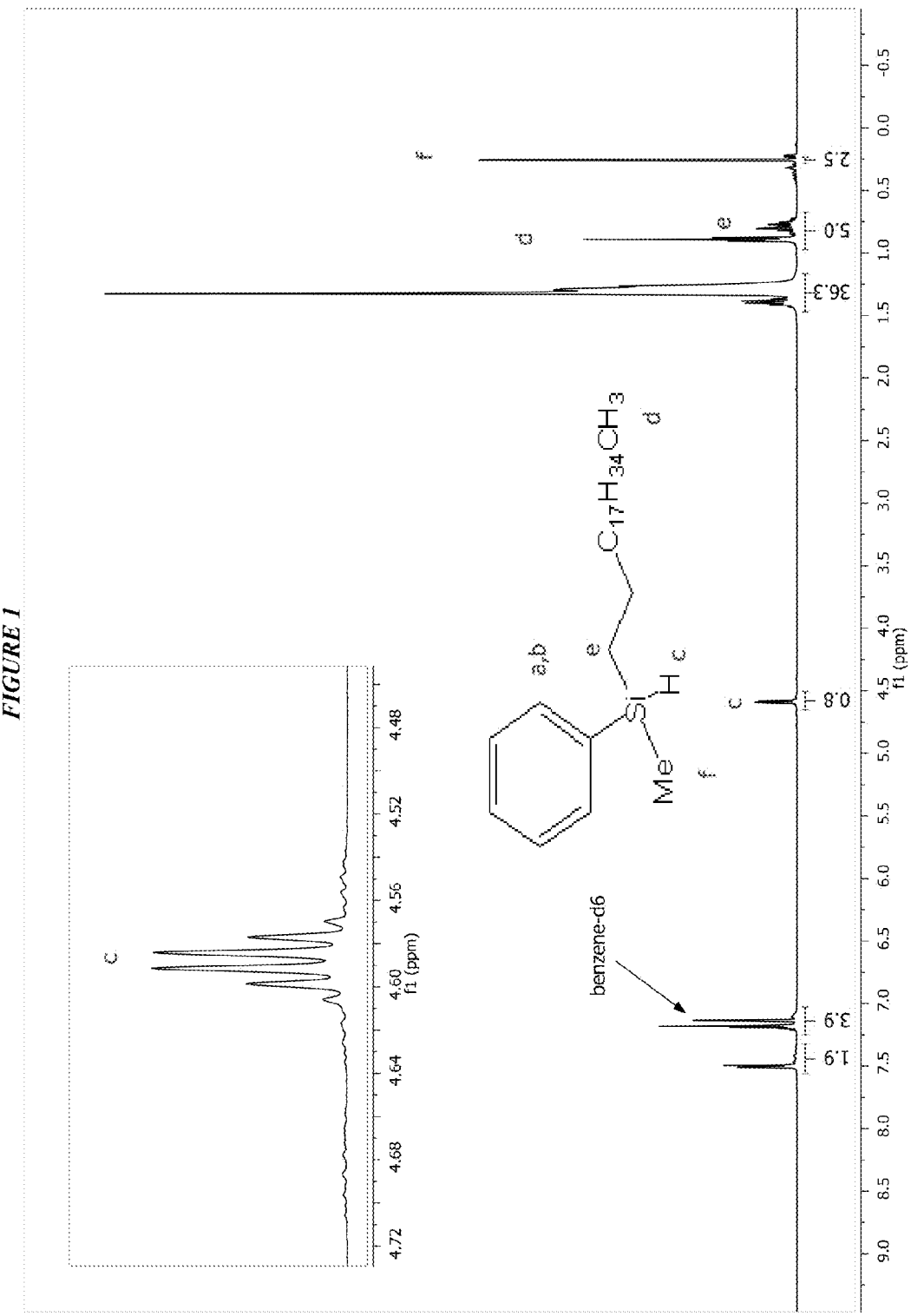
FIG. 1 depicts an $^1$H NMR of C-20 alpha-olefin hydrosilylated with PhMeSiH$_2$ using Cp$_2$ZrMe$_2$/nBuLi catalyst in toluene at 90° C.

As used herein, the term "oligomer" is defined to have an Mn of from 100 to 25,000 g/mol as measured by $^1$H NMR. A polymer has an Mn of more than 25,000 g/mol. A propylene oligomer or polymer is an oligomer or polymer having at least 50 mol % of propylene, respectively. As used herein, Mn is number average molecular weight (measured by $^1$H NMR unless stated otherwise), Mw is weight average molecular weight (measured by Gel Permeation Chromatography), and Mz is z average molecular weight (measured by Gel Permeation Chromatography), wt % is weight percent, and mol % is mole percent. Molecular weight distribution (MWD) is defined to be Mw (measured by Gel Permeation Chromatography) divided by Mn (measured by $^1$H NMR). Unless otherwise noted, all molecular weight units (e.g., Mw, Mn, Mz) are g/mol. An "olefin," alternatively referred to as "alkene," is a linear, branched, or cyclic compound of carbon and hydrogen having at least one double bond. For purposes of this specification and the claims appended thereto, when a polymer or copolymer (or oligomer or co-oligomer) is referred to as comprising an olefin, including, but not limited to ethylene, propylene, and butene, the olefin present in such polymer or copolymer (or oligomer or co-oligomer) is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. A "polymer" has two or more of the same or different mer units. A "homo-oligomer" is an oligomer having mer units that are the same. A "co-oligomer" is an oligomer having two or more mer units that are different from each other. The term "different" as used to refer to mer units indicates that the mer units differ from each other by at least one atom or are different isomerically. Accordingly, the definition of copolymer or co-oligomer, as used herein, includes terpolymers or "ter-oligomers" and the like. The term "different" as used to refer to polyolefins indicates that the mer units of the polyolefins differ from each other by at least one atom, the mer units of the polyolefins differ isomerically, the polyolefins differ in Mn, Mw, Mz, tacticity, Mw/Mn, g'vis, vinyl, vinylidene, vinylene, or internal unsaturation content, amount of comonomer (when the comonomer is the same or different in the polyolefins), density, melting point, heat of fusion, and the like. Accordingly, the definition of copolymer or co-oligomer, as used herein, includes terpolymers or "ter-oligomers" and the like.

A "higher" alpha-olefin is an alpha-olefin having at least 4 carbon atoms. Ethylene shall be considered an alpha-olefin.

Bromine number is determined by ASTM D 1159. ICPES (Inductively Coupled Plasma Emission Spectrometry), which is described in J. W. Olesik, "Inductively Coupled Plasma-Optical Emission Spectroscopy," in the Encyclopedia of Materials Characterization, C. R. Brundle, C. A. Evans, Jr. and S. Wilson, eds., Butterworth-Heinemann, Boston, Mass., 1992, pp. 633-644, is used to determine the amount of an element in a material.

The following abbreviations may used through this specification: Me is methyl, Ph is phenyl, Et is ethyl, Pr is propyl, iPr is isopropyl, n-Pr is normal propyl, Bu is butyl, iBu is isobutyl, tBu is tertiary butyl, nBu is normal butyl, TMS is trimethylsilyl, TIBAL is triisobutylaluminum, TNOAL is triisobutyl n-octylaluminum, MAO is methylalumoxane, pMe is para-methyl, Ar* is 2,6-diisopropylaryl, Bz is benzyl, THF is tetrahydrofuran, RT is room temperature and tol is toluene.

In a preferred embodiment, this invention relates to a process to functionalize polyolefins comprising contacting a metallocene catalyst with a hydrosilylating agent, optionally, in the presence of a reducing agent (e.g., such as nBuLi, EtMgCl, LiAlH$_4$, NaEt, Na or Li), and one or more vinyl terminated polyolefins, wherein:
the bridged or unbridged metallocene is represented by the formula:

T is a bridging group;
n is 0 or 1, indicating the presence or absence of a bridging group;
each Cp is, independently, a substituted or unsubstituted cyclopentadienyl ring;
M is Zr, Ti, or Hf; and
each X is, independently, selected from the group consisting of hydrocarbyl radicals having from 1 to 20 carbon atoms, hydrides, amides, alkoxides, sulfides, phosphides, halogens, dienes, amines, phosphines, ethers, or a combination thereof.

In one aspect, the hydrosilylation agent is represented by the formula: Si(R*)$_m$H$_n$ or Si(R*)$_r$H$_s$LSi(R**)$_p$H$_q$, m=1 or 2, n=2 or 3; m+n=4; each R*, independently, is a H, or a $C_1$ to a $C_{20}$ substituted or unsubstituted hydrocarbyl group, where any two R* may form a cyclic structure with Si, r=0 or 1; s=2 or 3; r+s=3; p=0 or 1; q=2 or 3; p+q=3; L is a bond or a linking group; and R, independently, is a H, or a $C_1$ to a $C_{20}$ substituted or unsubstituted hydrocarbyl group, where any two R may form a cyclic structure with Si.

The vinyl terminated polyolefin is substituted or unsubstituted hydrocarbyl group having from 20 to about 10,000 carbon atoms and at least 5% allyl chain ends (relative to total unsaturations).

Process to Functionalize Polyolefins

This invention relates to a process to functionalize polyolefins (as used herein, polyolefin is defined to include both polymers and oligomers) comprising contacting a metallocene catalyst with a hydrosilylating agent, optionally in the presence of a reducing agent such as a base, and one or more vinyl terminated polyolefins.

The reactants are typically combined in a reaction vessel at a temperature of −50° C. to 300° C. (preferably 25° C., preferably 150° C.). Likewise the reactants are typically combined at a pressure of 0 to 1000 MPa (preferably 0.5 to 500

MPa, preferably 1 to 250 MPa) for a residence time of 0.5 seconds to 10 hours (preferably 1 second to 5 hours, preferably 1 minute to 1 hour).

Typically, from about 0.7 to about 4.0 (e.g., 0.8 to 2.6), preferably from about 1.0 to about 2.0, and most preferably from about 1.1 to about 1.7 moles of the hydrosilylation reagent are charged to the reactor per mole of polyolefin charged.

Typically, 0.00001 to 0.1 moles, preferably 0.0001 to 0.02 moles, preferably 0.0005 to 0.01 moles of metallocene are charged to the reactor per mole of polyolefin charged.

The process is typically a solution process, although it may be a bulk or high pressure process. Homogeneous processes are preferred. (A homogeneous process is defined to be a process where at least 90 wt % of the product is soluble in the reaction media.) A bulk homogeneous process is particularly preferred. (A bulk process is defined to be a process where reactant concentration in all feeds to the reactor is 70 vol % or more.) Alternately no solvent or diluent is present or added in the reaction medium, (except for the small amounts used as the carrier for the catalyst or other additives, or amounts typically found with the reactants; e.g., propane in propylene).

Suitable diluents/solvents for the process include non-coordinating, inert liquids. Examples include straight and branched-chain hydrocarbons such as isobutane, butane, pentane, isopentane, hexanes, isohexane, heptane, octane, dodecane, and mixtures thereof; cyclic and alicyclic hydrocarbons such as cyclohexane, cycloheptane, methylcyclohexane, methylcycloheptane, and mixtures thereof such as can be found commercially (Isopar™); perhalogenated hydrocarbons such as perfluorinated $C_{4-10}$ alkanes, chlorobenzene, and aromatic and alkylsubstituted aromatic compounds such as benzene, toluene, mesitylene, and xylene. In a preferred embodiment, the feed concentration for the process is 60 vol % solvent or less, preferably 40 vol % or less, preferably 20 vol % or less.

The process may be batch, semi-batch or continuous. As used herein, the term continuous means a system that operates without interruption or cessation. For example, a continuous process to produce a polymer would be one where the reactants are continually introduced into one or more reactors and polymer product is continually withdrawn.

Useful reaction vessels include reactors, including continuous stirred tank reactors, batch reactors, reactive extruder, pipe or pump.

In a preferred embodiment, the productivity of the process is at least 200 g of a hydrosilane-functionalized polyolefin per mmol of catalyst per hour, preferably at least 5000 g/mmol/hour, preferably at least 10,000 g/mmol/hr, preferably at least 300,000 g/mmol/hr.

This invention further relates to a process, preferably an in-line process, preferably a continuous process, to produce functionalized polyolefin, comprising introducing monomer and catalyst system into a reactor, obtaining a reactor effluent containing vinyl terminated polyolefin, optionally removing (such as flashing off) solvent, unused monomer and/or other volatiles, obtaining vinyl terminated polyolefin (such as those described herein), introducing vinyl terminated polyolefin, metallocene catalyst (as described herein) and hydrosilane (as described herein) into a reaction zone (such as a reactor, an extruder, a pipe and/or a pump) and obtaining functionalized polyolefin (such as those described herein).

Metallocene Catalysts

A metallocene catalyst is defined as an organometallic compound with at least one π-bound cyclopentadienyl moiety (or substituted cyclopentadienyl moiety) and more frequently two π-bound cyclopentadienyl moieties or substituted cyclopentadienyl moieties. This includes other π-bound moieties such as indenyls or fluorenyls or derivatives thereof.

Useful metallocenes include those represented by the formula: $TnCp_2MX_2$, wherein each Cp is, independently, a substituted cyclopentadienyl ring (preferably selected from the group consisting of hydrocarbyl radicals having from 1 to 20 carbon atoms) or an unsubstituted cyclopentadienyl ring and the Cp groups may be bridged by a bridging group T (preferably represented by the formula $R_2{}^aJ$, where J is C, Si or Ge, and each $R^a$ is, independently, hydrogen, halogen, $C_1$ to $C_{20}$ hydrocarbyl or a $C_1$ to $C_{20}$ substituted hydrocarbyl, and two $R^a$ can form a cyclic structure including aromatic, partially saturated, or saturated cyclic or fused ring system);

n is 0 or 1, indicating the presence or absence of a bridge, T;

M is Zr, Ti, or Hf, preferably Zr;

each X is, independently, selected from the group consisting of hydrocarbyl radicals having from 1 to 20 carbon atoms, hydrides, amides, alkoxides, sulfides, phosphides, halogens, dienes, amines, phosphines, ethers, or a combination thereof.

In a preferred embodiment, n is 0. In another preferred embodiment, at least 1 position on the Cp ring is H, preferably at least 2 positions on the Cp ring are hydrogen, preferably at least 3, preferably at least 4, preferably 5 positions are H, or if the Cp is an indene, at least 1 position on the Cp ring is H, preferably at least 2, at least 3, at least 4, at least 5, at least 6, or 7 of the positions on the indene are hydrogen. In a preferred embodiment, n is 0, and at least 1 position on the Cp ring is hydrogen, preferably at least 2 positions on the Cp ring are H, preferably at least 3, preferably at least 4, preferably 5 positions are H, or if the Cp is an indene, preferably at least 1 position is H, preferably at least 2 positions are H, preferably at least 3, at least 4, at least 5, at least 6, or 7 of the positions on the indene are hydrogen. In another preferred embodiment, n is optionally 0 and at least 2 positions on the Cp ring are hydrogen, preferably at least 3, preferably at least 4, preferably 5, or if the Cp is an indene, preferably at least 2, at least 3, at least 4, at least 5, at least 6, or 7 of the positions in the indene are hydrogen, provided that if any positions on the Cp or indene are substituted that the substituent on the Cp or indene is a small group, such as a $C_1$ to $C_{10}$ hydrocarbyl, preferably a $C_1$ to $C_6$ alkyl, preferably a $C_1$ to $C_4$ alkyl, such as methyl, ethyl, propyl, or butyl. In a particularly preferred embodiment, the substituent groups on the Cp do not form a substituted or unsubstituted fluorene. In another preferred embodiment, the Cp is not a substituted or unsubstituted indene. In a particularly preferred embodiment, the substituent groups on the Cp do not form a substituted or unsubstituted fluorene or a substituted or unsubstituted indene.

In a preferred embodiment, the metallocene is one or more of any precursor that can be reduced to a $[Cp_2ZrII]$ species; generally halides $Cp_2ZrCl_2$, $Cp_2ZrBr_2$, etc, $Cp_2HfCl_2$, $Cp_2TiCl_2$, mixed halides, dimers $[Cp_2ZrCl]_2Cl$, with any halide. These require reductants such as nBuLi, t-BuLi, EtMgCl, Na, Li, Mg, K, LiH, LiBEt$_3$H, NaBH$_4$, LiAlH$_4$, sec-BuLi, (nBu)$_2$Mg, MeLi, R*ZnX*, wherein X* is a leaving group such as a halide and R* is a hydrocarbyl group. The metallocene can be bridged or unbridged.

In another embodiment, the metallocene can be a bridged or unbridged substituted metallocene such as $T_n(CpMe)_2MX_2$, $T_n(CpPrMe)_2MX_2$, $T_n(CpBuMe)_2MX_2$, $T_n(Cpn-Pr)_2MX_2$, $T_n(Cpt-Butyl)_2MX_2$, $T_n(CpSiMe_3)_2MX_2$, $T_n(Indenyl)(Cp)MX_2$, $T_n(Fluorenyl)(Cp)MX_2$, wherein M, T, X and n are as defined above, preferably n is 0. Suitable T groups include, for example, $Me_2Si$, $CR^*_2$, $Et_2Si$, $CH_2CH_2$ and the like wherein R* is a hydrocarbyl group.

A "catalyst system" is combination of at least one catalyst compound, at least one activator, an optional co-activator, and an optional support material, where the system can polymerize monomers to polymer. For the purposes of this invention and the claims thereto, when catalyst systems are described as comprising neutral stable forms of the components, it is well understood by one of ordinary skill in the art, that the ionic form of the component is the form that reacts with the monomers to produce polymers.

In the description herein, the metallocene catalyst may be described as a catalyst precursor, a pre-catalyst compound, or a transition metal compound, and these terms are used interchangeably. An "anionic ligand" is a negatively charged ligand which donates one or more pairs of electrons to a metal ion. A "neutral donor ligand" is a neutrally charged ligand which donates one or more pairs of electrons to a metal ion.

Hydrosilylation Reagents

In one aspect, the hydrosilylation agent is represented by the formula:

where m=1 or 2; n*=2 or 3; m+n*=4; each R*, independently, is a H, or a $C_1$ to a $C_{20}$ substituted or unsubstituted hydrocarbyl group, where any two R* may form a cyclic structure with Si.

Preferably one R* is a $C_1$ to $C_{50}$ hydrocarbyl group, preferably $C_1$ to $C_{30}$, more preferably $C_1$ to $C_{18}$, preferably R* is a hydrogen, a phenyl group, hexyl group or a methyl group.

In one aspect, the hydrosilylation agent is represented by the formula:

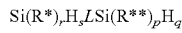

wherein r=0 or 1; s=2 or 3; r+s=3; p=0 or 1; q=2 or 3; p+q=3; L is a bond or a linking group; each R*, independently, is a H, or a $C_1$ to a $C_{20}$ substituted or unsubstituted hydrocarbyl group (preferably hydrogen, a phenyl group, hexyl group or a methyl group), where any two R* may form a cyclic structure with Si; and each R, independently, is a H, or a $C_1$ to a $C_{20}$ substituted or unsubstituted hydrocarbyl group, where any two R may form a cyclic structure with Si.

In another embodiment, preferred hydrosilylation reagents further include those represented by the formulae:

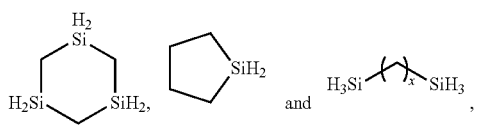

wherein x is a number from 1 to 40. It should be understood that excess hydrosilylation reagent is used during the reaction to cause mono-hydrosilylation to occur and reaction times are kept to a minimum.

In a preferred embodiment, the hydrosilylation agent is one or more of $PhMeSiH_2$, $Ph_2SiH_2$, n-hexylSiH$_3$, allyldimethoxysilane, allylsilane, allylmethylsilane, benzylsilane, benzylmethylsilane, bicycloheptenyl)ethyl]methylsilane, bicycloheptenyl)ethyl]silane, 5-(bicycloheptenyl)methylsilane, 5-(bicycloheptenyl)silane, 2-(bicycloheptyl)silane, 1,4-bis(methylsilyl)benzene, 1,4-bis(methylsilyl)butane, 1,2-bis(methylsilyl)ethane bis(nonafluorohexyl)silane, $SiH_3(CH_2)_2SiH_3$, $SiH_3(CH_2)_6SiH_3$, $SiH_3(CH_2)_{16}SiH_3$, $SiH_3(CH_2)_8SiH_3$, $SiH_3(CH_2)_3SiH_3$, $SiH_3(CH_2)_{10}SiH_3$, $SiH_3(CH_2)_7SiH_3$, ortho, meta or para-$SiH_3(C_6H_4)_2SiH_3$, bis(trimethylsilylmethyl)silane, butenylmethylsilane, t-butylsilane, n-butylmethylsilane, t-butylmethylsilane, p-(t-butyl)phenethylsilane, t-butylphenylsilane, n-butylsilane, (p-chloromethyl)phenylsilane, [2-(3-cyclohexenyl)ethyl]methylsilane, [2-(3-cyclohexenyl)ethyl]silane, 3-cyclohexenylsilane, cyclohexylmethylsilane, cyclooctylsilane, cyclopentylsilane, n-decylsilane, n-decylmethylsilane, di(t-butylamino)silane, di-t-butylsilane, dicyclopentylsilane, diethylsilane, di-n-hexylsilane, diisopropylsilane, dimesitylsilane, (3,3-dimethylbutyl)silane, dimethylsilane, di-n-octylsilane, diphenylsilane, 1,3-disilabutane, 1,4-disilabutane, disilane, 1,3-disilapropane, di(p-tolyl))silane, docosylsilane, dodecylsilane, eicosylsilane, ethylsilane, ethylmethylsilane, n-heptylmethylsilane, n-heptylsilane, hexylsilane, isobutylsilane, isooctylsilane, isopropylmethylsilane, isopropylsilane, methylsilane, p-(methylphenethyl)methylsilane, (1-naphthylmethyl)silane, n-octadecylmethylsilane, n-octadecylsilane, n-octylsilane, n-octylmethylsilane, pentafluorophenylpropylmethylsilane, pentafluorophenylpropylsilane, pentylsilane, n-pentylmethylsilane, phenylethylsilane, 6-phenylhexylsilane, phenylmethylsilane, 1-phenyl-1-(methyl,4-sila)butane, phenylsilane, n-propylsilane, p-tolylsilane, p-tolylmethylsilane, 1,3,5-trisilacyclohexane, trisilane, 10-undecenylsilane, and the like.

Base Reagents

A strong reducing agent such as n-butyl lithium can be used to help facilitate the hydrosilylation process when X is a halide in the metallocene. Other suitable reducing agents include, for example, t-BuLi, EtMgCl, Na, Li, Mg, K, LiH, LiBEt$_3$H, NaBH$_4$, LiAlH$_4$, sec-BuLi, (nBu)$_2$Mg, MeLi, R*ZnX*, wherein X* is a leaving group such as a halide and R* is a hydrocarbyl group.

Vinyl Terminated Polyolefins

For purposes of this invention and claims thereto "Allyl chain ends" (also referred to as "vinyl termination" "vinyl chain ends" or "vinyl content") is defined to be a polyolefin (polymer or oligomer) having at least one terminus represented by formula I:

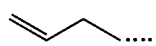

allylic vinyl end group where the "••••" represents the polyolefin chain. In a preferred embodiment, the allyl chain end is represented by the formula II:

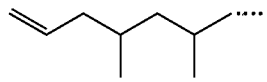

allylic vinyl end group

The amount of allyl chain ends is determined using $^1$H NMR at 120° C. using deuterated tetrachloroethane as the solvent on a 500 MHz machine, and in selected cases confirmed by $^{13}$C NMR. Resconi has reported proton and carbon assignments (neat perdeuterated tetrachloroethane used for proton spectra while a 50:50 mixture of normal and perdeuterated tetrachloroethane was used for carbon spectra; all spectra were recorded at 100° C. on a Bruker AM 300 spectrometer operating at 300 MHz for proton and 75.43 MHz for carbon) for vinyl terminated propylene oligomers in J. American Chemical Soc., 114 1992, pp. 1025-1032 that are useful herein.

"Isobutyl chain end" is defined to be a polyolefin having at least one terminus represented by the formula:

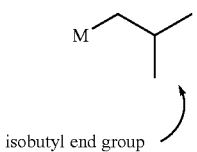
isobutyl end group where M represents the polyolefin chain. In a preferred embodiment, the isobutyl chain end is represented by one of the following formulae:

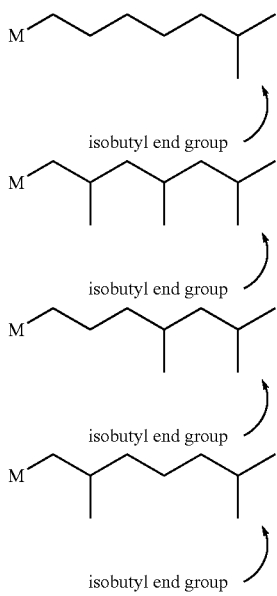

where M represents the polyolefin chain.

Figure 2:
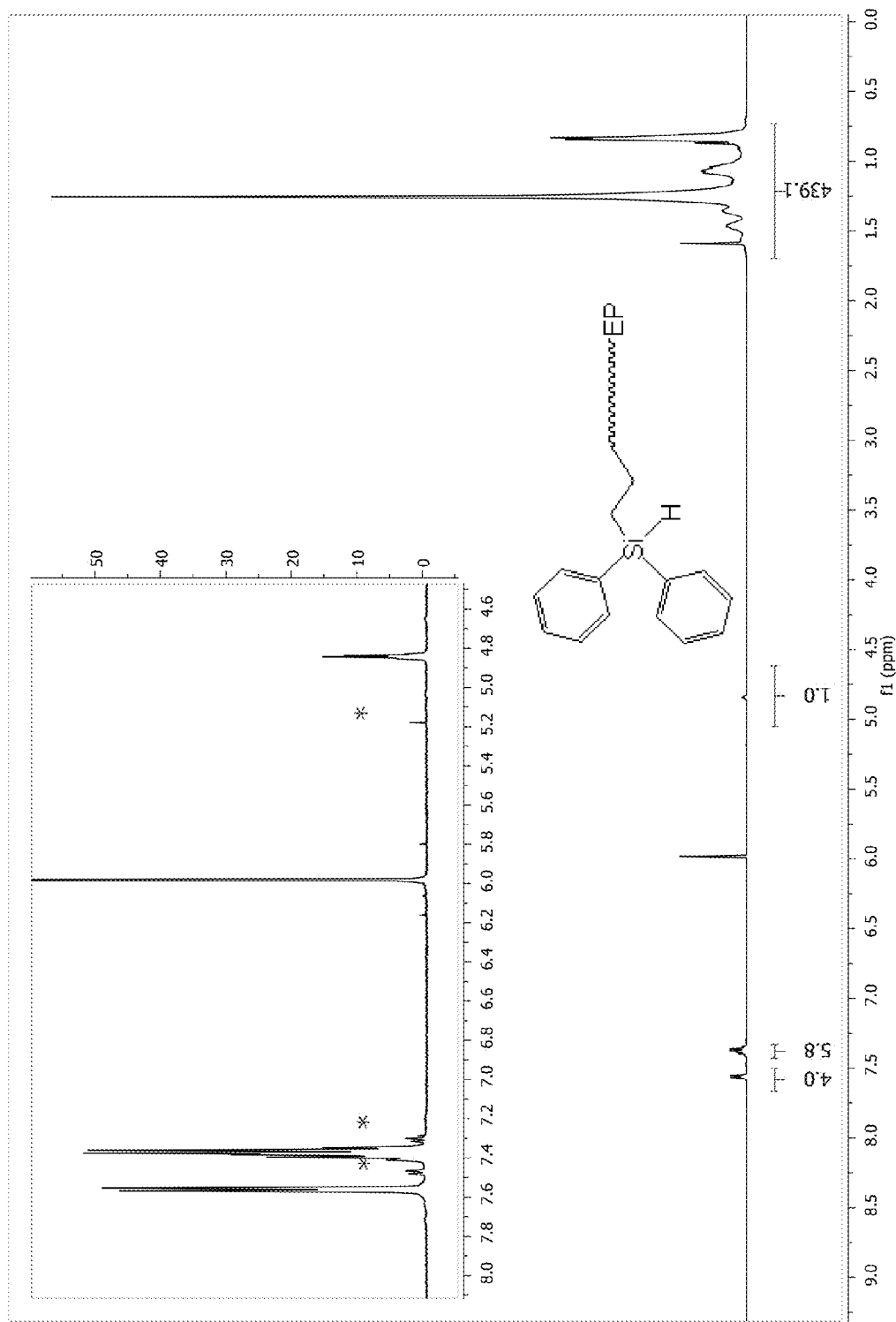
FIG. 2 depicts an $^1$H NMR spectrum of Compound 3 from Scheme 2.
Figure 3:
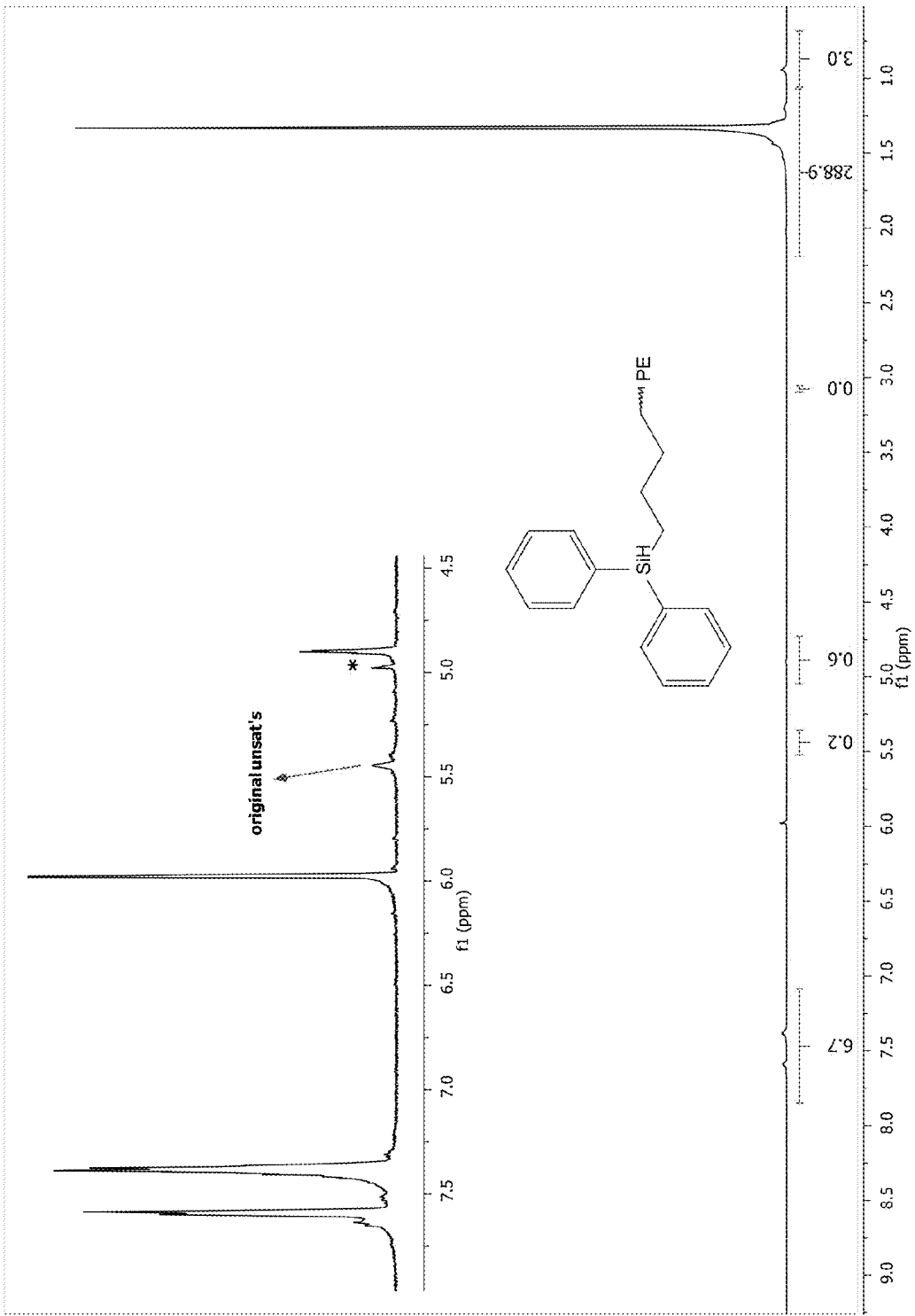
FIG. 3 depicts an $^1$H NMR spectrum of Compound 4 from Scheme 3.
Figure 4:
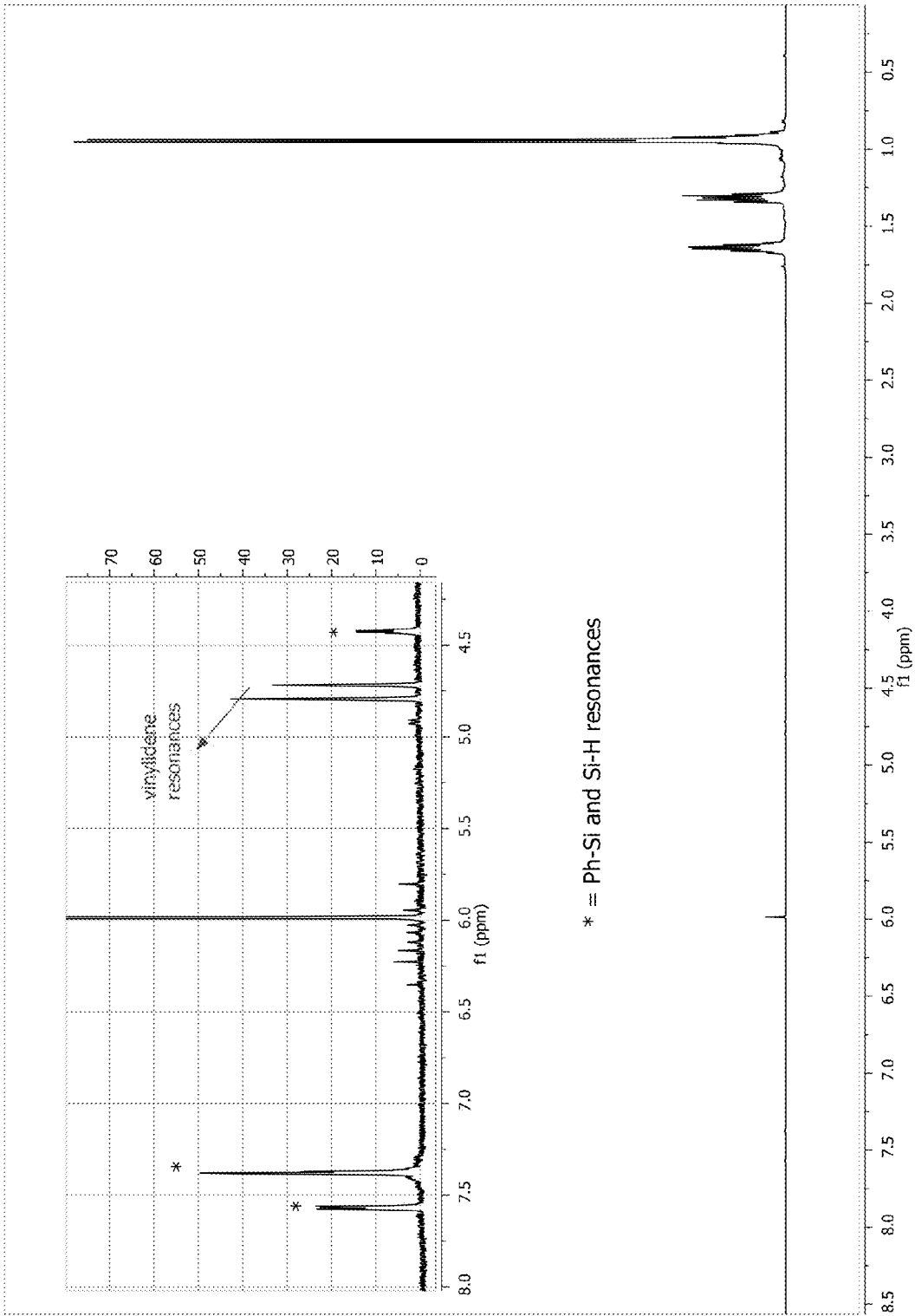
FIG. 4 depicts an $^1$H NMR spectrum of Compound 5 from Scheme 4.

The percentage of isobutyl end groups is determined using $^{13}C$ NMR (as described in the example section) and the chemical shift assignments in Resconi et al, J. Am. Chem. Soc., 1992, 114, pp. 1025-1032 for 100% propylene oligomers (and polymers) and set forth in FIG. 2 for WO 2009/155471.

This invention can be practiced with any vinyl containing materials, preferably with vinyl terminated polyolefins, such as vinyl terminated ethylene homo- and co-polymers, and vinyl terminated propylene homo- and co-polymers. Many of these materials are known in the art and can be functionalized using the processes described herein, e.g., contacting a metallocene catalyst (as described herein) with an hydrosilylation agent (as described herein) and one or more vinyl containing materials. Vinyl terminated polyolefins useful herein include homo- and co-polymers of heteroatom containing monomers, as well as polymers of olefin monomers only. Vinyl terminated oligomers useful herein include homo- and co-oligomers of heteroatom containing monomers, as well as oligomers of olefin monomers only. For purpose of this invention and the claims thereto, the term vinyl terminated polyolefin includes the terms vinyl terminated polymers and vinyl terminated oligomers. Preferred vinyl terminated polyolefins include vinyl terminated isotactic polypropylene (preferably having a melting point of 100° C. or more, preferably 155° C. or more), vinyl terminated polyethylene (preferably having a melting point of 100° C. or more, preferably 155° C. or more).

In a preferred embodiment, the vinyl terminated polyolefin used herein has at least 90% or greater terminal vinyl groups.

In a preferred embodiment, the vinyl terminated polyolefin used herein has an Mn of from 500 to 50,000 g/mol, preferably from 1000 to 30,000 g/mol, preferably from 1,500 to 20,000 g/mol.

In a preferred embodiment, the vinyl terminated polyolefin is a homopolymer, homo-oligomer, copolymer or co-oligomer comprising one or more $C_2$ to $C_{40}$ olefins, preferably $C_2$ to $C_{40}$ alpha-olefins, preferably ethylene, propylene, butene, pentene, hexene, octene, nonene, decene, undecene, dodecene. In a preferred embodiment, the vinyl terminated polyolefin used herein has an Mn of from 500 to 50,000 g/mol, preferably from 1000 to 30,000 g/mol, preferably from 1,500 to 20,000 g/mol and is a homopolymer, homo-oligomer, copolymer or co-oligomer comprising two or more $C_2$ to $C_{40}$ olefins, preferably $C_3$ to $C_{20}$ alpha-olefins, preferably ethylene, propylene, butene, pentene, hexene, octene, nonene, decene, undecene, or dodecene.

In a preferred embodiment, the vinyl terminated polyolefin is a polyolefin having an Mn of from 500 to 100,000 g/mol (preferably 700 to 21,000, preferably 800 to 20,000 g/mol) comprising one or more alpha-olefins selected from the group consisting of $C_2$ to $C_{40}$ alpha-olefins, preferably ethylene, propylene, butene, pentene, hexene, octene, nonene, decene, undecene, or dodecene. In a preferred embodiment the vinyl terminated polyolefin is an oligomer having an Mn of from 500 to 10,000 g/mol (preferably 700 to 21,000, preferably 800 to 20,000 g/mol) comprising two or more alpha-olefins selected from the group consisting of $C_2$ to $C_{40}$ alpha-olefins, preferably $C_3$ to $C_{20}$ alpha-olefins, preferably ethylene, propylene, butene, pentene, hexene, octene, nonene, decene, undecene, or dodecene.

Preferably the vinyl terminated polyolefin is an ethylene oligomer, e.g., a homo-oligomer of ethylene or co-oligomer of ethylene and up to 50 mol % (preferably from 0.5 to 25 mol %, preferably from 1 to 20 mol %) of one or more $C_3$ to $C_{40}$ alpha-olefin co monomers, preferably selected from the group consisting of propylene, butene, pentene, hexene, octene, nonene, decene, undecene, or dodecene. Alternately, the vinyl terminated polyolefin is a propylene oligomer, e.g., a homo-oligomer of propylene or co-oligomer of propylene and up to 50 mol % (preferably from 0.5 to 25 mol %, preferably from 1 to 20 mol %) of one or more $C_2$ and $C_4$ to $C_{40}$ alpha-olefin co monomers, preferably selected from the group consisting of ethylene, butene, pentene, hexene, octene, nonene, decene, undecene, or dodecene. Alternately, the vinyl terminated polyolefin is a copolymer or co-oligomer of ethylene and/or propylene and a $C_4$ to $C_{40}$ alpha-olefin, such as butene, pentene, hexene, octene, nonene, decene, undecene, or dodecene. Alternately, the vinyl terminated polyolefin is a copolymer or co-oligomer of ethylene and/or propylene and two or more $C_4$ to $C_{40}$ alpha-olefins, such as butene, pentene, hexene, octene, nonene, decene, undecene, or dodecene. In a particularly preferred embodiment, the vinyl terminated polyolefin is a copolymer or co-oligomer of:

1) ethylene and two or more $C_4$ to $C_{40}$ branched or unbranched alpha-olefins, such as butene, pentene, hexene, octene, nonene, decene, undecene, dodecene; and
2) propylene and two or more $C_4$ to $C_{40}$ branched or unbranched alpha-olefins, such as butene, pentene, hexene, octene, nonene, decene, undecene, dodecene, and
3) ethylene and propylene and two or more $C_4$ to $C_{40}$ branched or unbranched alpha-olefins, such as butene, pentene, hexene, octene, nonene, decene, undecene, dodecene, and 4) propylene and two or branched or unbranched alpha-olefins selected from butene, pentene, hexene, octene, nonene, decene, undecene, and dodecene.

In a preferred embodiment, the vinyl terminated polyolefin is a polymer having an Mn of greater than 21,000 g/mol (preferably from 25,000 to 100,000, preferably 25,000 to 50,000 g/mol) comprising one or more alpha-olefins selected from the group consisting of $C_2$ to $C_{40}$ alpha-olefins, preferably ethylene, propylene, butene, pentene, hexene, octene, nonene, decene, undecene, or dodecene. Preferably the vinyl terminated polyolefin is an ethylene polymer, e.g., a homopolymer of ethylene or co-polymer of ethylene and up to 50 mol % (preferably from 0.5 to 25 mol %, preferably from 1 to 20 mol %) of one or more $C_3$ to $C_{40}$ alpha-olefin comonomers, preferably selected from the group consisting of propylene, butene, pentene, hexene, octene, nonene, decene, undecene, or dodecene. Alternately, the vinyl terminated polyolefin is propylene polymer, e.g., a homopolymer of propylene or a co-polymer of propylene and up to 50 mol % (preferably from 0.5 to 25 mol %, preferably from 1 to 20 mol %) of one or more $C_2$ to $C_{40}$ alpha-olefins comonomers, preferably selected from the group consisting of ethylene, butene, pentene, hexene, octene, nonene, decene, undecene, or dodecene.

In another embodiment, the vinyl terminated polyolefin consist essentially of propylene, functional group and optionally ethylene.

Alternately $C_4$ olefins (such as isobutylene, butadiene, n-butene) are substantially absent from the vinyl terminated polyolefin. Alternately $C_{4-20}$ olefins are substantially absent from the vinyl terminated polyolefin. Alternately isobutylene is substantially absent from the vinyl terminated polyolefin. By substantially absent is meant that the monomer is present in the polyolefin at 1 wt % or less, preferably at 0.5 wt % or less, preferably at 0 wt %.

In another embodiment, the vinyl terminated polyolefin has a branching index, $g'_{vis}$ (as determined by GPC), of 0.98 or less, alternately 0.96 or less, alternately 0.95 or less, alternately 0.93 or less, alternately 0.90 or less, alternately 0.85 or less, alternately 0.80 or less, alternately 0.75 or less, alternately 0.70 or less, alternately 0.65 or less, alternately 0.60 or less, alternately 0.55 or less.

In a particularly preferred embodiment, the vinyl terminated polyolefin comprises one or more of:
a) a propylene co-oligomer (copolymer) having an Mn of 300 to 30,000 g/mol (as measured by $^1$H NMR) comprising 10 to 90 mol % propylene and 10 to 90 mol % of ethylene, wherein the oligomer has at least X % allyl chain ends (relative to total unsaturations), where: 1) X=(−0.94 (mol % ethylene incorporated)+100), when 10 to 60 mol % ethylene is present in the co-oligomer, and 2) X=45, when greater than 60 and less than 70 mol % ethylene is present in the co-oligomer, and 3) X=(1.83*(mol % ethylene incorporated)−83), when 70 to 90 mol % ethylene is present in the co-oligomer; and/or
b) a propylene oligomer, comprising more than 90 mol % propylene and less than 10 mol % ethylene, wherein the oligomer has: at least 93% allyl chain ends, an Mn of about 500 to about 20,000 g/mol (as measured by $^1$H NMR), an isobutyl chain end to allylic vinyl group ratio of 0.8:1 to 1.35:1.0, and less than 1400 ppm aluminum; and/or
c) a propylene oligomer, comprising at least 50 mol % propylene and from 10 to 50 mol % ethylene, wherein the oligomer has: at least 90% allyl chain ends, Mn of about 150 to about 10,000 g/mol (as measured by $^1$H NMR), and an isobutyl chain end to allylic vinyl group ratio of 0.8:1 to 1.3:1.0, wherein monomers having four or more carbon atoms are present at from 0 to 3 mol %; and/or
d) a propylene oligomer, comprising at least 50 mol % propylene, from 0.1 to 45 mol % ethylene, and from 0.1 to 5 mol % C4 to C12 olefin, wherein the oligomer has: at least 87% allyl chain ends (alternately at least 90%), an Mn of about 150 to about 10,000 g/mol, (as measured by $^1$H NMR), and an isobutyl chain end to allylic vinyl group ratio of 0.8:1 to 1.35:1.0; and/or
e) a propylene oligomer, comprising at least 50 mol % propylene, from 0.1 to 45 mol % ethylene, and from 0.1 to 5 mol % diene, wherein the oligomer has: at least 90% allyl chain ends, an Mn of about 150 to about 10,000 g/mol (as measured by $^1$H NMR), and an isobutyl chain end to allylic vinyl group ratio of 0.7:1 to 1.35:1.0; and/or
f) a homo-oligomer, comprising propylene, wherein the oligomer has: at least 93% allyl chain ends, an Mn of about 500 to about 20,000 g/mol (as measured by $^1$H NMR), an isobutyl chain end to allylic vinyl group ratio of 0.8:1 to 1.2:1.0, and less than 1400 ppm aluminum.

In a preferred embodiment, vinyl terminated polyolefins (such as vinyl terminated olefin oligomers and polymers) useful in this invention include propylene homo-oligomers, comprising propylene and less than 0.5 wt % comonomer, preferably 0 wt % comonomer, wherein the oligomer has:
i) at least 93% allyl chain ends (preferably at least 95%, preferably at least 97%, preferably at least 98%);
ii) a number average molecular weight (Mn) of about 500 to about 20,000 g/mol, as measured by $^1$H NMR (preferably 500 to 15,000, preferably 700 to 10,000, preferably 800 to 8,000 g/mol, preferably 900 to 7,000, preferably 1000 to 6,000, preferably 1000 to 5,000);
iii) an isobutyl chain end to allylic vinyl group ratio of 0.8:1 to 1.3:1.0; and
iv) less than 1400 ppm aluminum, (preferably less than 1200 ppm, preferably less than 1000 ppm, preferably less than 500 ppm, preferably less than 100 ppm).

Vinyl terminated olefin oligomers and polymers useful in this invention also include propylene co-oligomers (or copolymer) having an Mn of 300 to 30,000 g/mol as measured by $^1$H NMR (preferably 400 to 20,000, preferably 500 to 15,000, preferably 600 to 12,000, preferably 800 to 10,000, preferably 900 to 8,000, preferably 900 to 7,000 g/mol), comprising 10 to 90 mol % propylene (preferably 15 to 85 mol %, preferably 20 to 80 mol %, preferably 30 to 75 mol %, preferably 50 to 90 mol %) and 10 to 90 mol % (preferably 85 to 15 mol %, preferably 20 to 80 mol %, preferably 25 to 70 mol %, preferably 10 to 50 mol %) of one or more alpha-olefin comonomers (preferably ethylene, butene, hexene, or octene, preferably ethylene), wherein the oligomer has at least X % allyl chain ends (relative to total unsaturations), where: 1) X=(−0.94 (mol % ethylene incorporated)+100 {alternately 1.20 (−0.94 (mol % ethylene incorporated)+100), alternately 1.50 (−0.94 (mol % ethylene incorporated)+100)}), when 10 to 60 mol % ethylene is present in the co-oligomer, and 2) X=45 (alternately 50, alternately 60), when greater than 60 and less than 70 mol % ethylene is present in the co-oligomer, and 3) X=(1.83*(mol % ethylene incorporated)−83, {alternately 1.20 [1.83*(mol % ethylene incorporated)−83], alternately 1.50 [1.83*(mol % ethylene incorporated)−83]}), when 70 to 90 mol % ethylene is present in the co-oligomer. Alternately X is 80% or more, preferably 85% or more, preferably 90% or more, preferably 95% or more. In an alternate embodiment the oligomer has at least 80% isobutyl chain ends (based upon the sum of isobutyl and n-propyl saturated chain ends), preferably at least 85% isobutyl chain ends, preferably at least 90% isobutyl chain ends. Alternately, the oligomer has an isobutyl chain end to allylic vinyl group ratio of 0.8:1 to 1.35:1.0, preferably 0.9:1 to 1.20:1.0, preferably 0.9:1.0 to 1.1:1.0.

Vinyl terminated olefin oligomers and polymers useful in this invention also include propylene oligomers (or polymers), comprising more than 90 mol % propylene (preferably 95 to 99 mol %, preferably 98 to 99 mol %) and less than 10 mol % ethylene (preferably 1 to 4 mol %, preferably 1 to 2 mol %), wherein the oligomer has:
  i) at least 93% allyl chain ends (preferably at least 95%, preferably at least 97%, preferably at least 98%);
  ii) a number average molecular weight (Mn) of about 400 to about 30,000 g/mol, as measured by $^1$H NMR (preferably 500 to 20,000, preferably 600 to 15,000, preferably 700 to 10,000 g/mol, preferably 800 to 9,000, preferably 900 to 8,000, preferably 1000 to 6,000);
  iii) an isobutyl chain end to allylic vinyl group ratio of 0.8:1 to 1.35:1.0, and
  iv) less than 1400 ppm aluminum, (preferably less than 1200 ppm, preferably less than 1000 ppm, preferably less than 500 ppm, preferably less than 100 ppm).

Vinyl terminated olefin oligomers and polymers useful in this invention also include propylene oligomers, comprising: at least 50 (preferably 60 to 90, preferably 70 to 90) mol % propylene and from 10 to 50 (preferably 10 to 40, preferably 10 to 30) mol % ethylene, wherein the oligomer has:
  i) at least 90% allyl chain ends (preferably at least 91%, preferably at least 93%, preferably at least 95%, preferably at least 98%);
  ii) an Mn of about 150 to about 20,000 g/mol, as measured by $^1$H NMR (preferably 200 to 15,000, preferably 250 to 15,000, preferably 300 to 10,000, preferably 400 to 9,500, preferably 500 to 9,000, preferably 750 to 9,000); and
  iii) an isobutyl chain end to allylic vinyl group ratio of 0.8:1 to 1.3:1.0, wherein monomers having four or more carbon atoms are present at from 0 to 3 mol % (preferably at less than 1 mol %, preferably less than 0.5 mol %, preferably at 0 mol %).

Vinyl terminated olefin oligomers and polymers useful in this invention also include propylene oligomers, comprising: at least 50 (preferably at least 60, preferably at least 70 to 99.5, preferably at least 80 to 99, preferably at least 90 to 98.5) mol % propylene, from 0.1 to 45 (alternately at least 35, preferably 0.5 to 30, preferably 1 to 20, preferably 1.5 to 10) mol % ethylene, and from 0.1 to 5 (preferably 0.5 to 3, preferably 0.5 to 1) mol % $C_4$ to $C_{12}$ olefin (such as butene, hexene or octene, preferably butene), wherein the oligomer has:
  i) at least 90% allyl chain ends (preferably at least 91%, preferably at least 93%, preferably at least 95%, preferably at least 98%);
  ii) a number average molecular weight (Mn) of about 150 to about 15,000 g/mol, as measured by $^1$H NMR (preferably 200 to 12,000, preferably 250 to 10,000, preferably 300 to 10,000, preferably 400 to 9500, preferably 500 to 9,000, preferably 750 to 9,000); and
  iii) an isobutyl chain end to allylic vinyl group ratio of 0.8:1 to 1.35:1.0.

Vinyl terminated olefin oligomers and polymers useful in this invention also include propylene oligomers, comprising: at least 50 (preferably at least 60, preferably 70 to 99.5, preferably 80 to 99, preferably 90 to 98.5) mol % propylene, from 0.1 to 45 (alternately at least 35, preferably 0.5 to 30, preferably 1 to 20, preferably 1.5 to 10) mol % ethylene, and from 0.1 to 5 (preferably 0.5 to 3, preferably 0.5 to 1) mol % diene (such as $C_4$ to $C_{12}$ alpha-omega dienes (such as butadiene, hexadiene, octadiene), norbornene, ethylidene norbornene, vinylnorbornene, norbornadiene, and dicyclopentadiene), wherein the oligomer has:
  i) at least 90% allyl chain ends (preferably at least 91%, preferably at least 93%, preferably at least 95%, preferably at least 98%);
  ii) a number average molecular weight (Mn) of about 150 to about 20,000 g/mol, as measured by $^1$H NMR (preferably 200 to 15,000, preferably 250 to 12,000, preferably 300 to 10,000, preferably 400 to 9,500, preferably 500 to 9,000, preferably 750 to 9,000); and
  iii) an isobutyl chain end to allylic vinyl group ratio of 0.7:1 to 1.35:1.0.

In another embodiment, the vinyl terminated polyolefin (also referred to as a vinyl terminated macromer or "VTM") useful herein may be one or more vinyl terminated polyolefins having an Mn (measured by $^1$H NMR) of 200 g/mol or more, (preferably 300 to 60,000 g/mol, 400 to 50,000 g/mol, preferably 500 to 35,000 g/mol, preferably 300 to 15,000 g/mol, preferably 400 to 12,000 g/mol, or preferably 750 to 10,000 g/mol); and comprising: (i) from about 20 to 99.9 mol % (preferably from about 25 to about 90 mol %, from about 30 to about 85 mol %, from about 35 to about 80 mol %, from about 40 to about 75 mol %, or from about 50 to about 95 mol %) of at least one $C_5$ to $C_{40}$ olefin (preferably $C_5$ to $C_{30}$ α-olefins, more preferably $C_5$ to $C_{20}$ α-olefins, preferably, $C_5$ to $C_{12}$ α-olefins, preferably pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexane, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene); and (ii) from about 0.1 to 80 mol % of propylene (preferably from about 5 mol % to 70 mol %, from about 10 to about 65 mol %, from about 15 to about 55 mol %, from about 25 to about 50 mol %, or from about 30 to about 80 mol %); wherein the VTM has at least 40% allyl chain ends (preferably at least 50% allyl chain ends, at least 60% allyl chain ends, at least 70% allyl chain ends; at least 80% allyl chain ends, at least 90% allyl chain ends; at least 95% allyl chain ends); and, optionally, an isobutyl chain end to allylic chain end ratio of less than 0.70:1 (preferably less than 0.65:1, less than 0.60:1, less than 0.50:1, or less than 0.25:1), and further optionally, an allyl chain end to vinylidene chain end (as determined by $^1$H NMR) ratio of more than 2:1 (preferably more than 2.5:1, more than 3:1, more than 5:1, or more than 10:1), and further optionally, an allyl chain end to vinylene chain end ratio of greater than 10:1 (preferably greater than 15:1, or greater than 20:1); and even further optionally preferably substantially no isobutyl chain ends (preferably less than 0.1 wt % isobutyl chain ends). For further information on such VTM's please see concurrently filed U.S. Ser. No. 13/072,249, filed Mar. 25, 2011, entitled "Vinyl Terminated Higher Olefin Copolymers and Methods to Produce Thereof."

In another embodiment, the VTM useful herein may be one or more vinyl terminated polyolefins having an Mn (measured by $^1$H NMR) of 200 g/mol or more (preferably 300 to 60,000 g/mol, 400 to 50,000 g/mol, preferably 500 to 35,000 g/mol, preferably 300 to 15,000 g/mol, preferably 400 to 12,000 g/mol, or preferably 750 to 10,000 g/mol) and comprises: (i) from about 80 to 99.9 mol % (preferably 85 to 99.9 mol %, more preferably 90 to 99.9 mol %) of at least one $C_4$ olefin (preferably 1-butene); and (ii) from about 0.1 to 20 mol % of propylene, preferably 0.1 to 15 mol %, more preferably 0.1 to 10 mol %; wherein the VTM has at least 40% allyl chain ends, preferably at least 50% allyl chain ends, at least 60% allyl chain ends, at least 70% allyl chain ends; or at least 80% allyl chain ends; and, optionally, an isobutyl chain end to allylic chain end ratio of less than 0.70:1, less than 0.65:1, less than 0.60:1, less than 0.50:1, or less than 0.25:1, and further optionally, an allyl chain end to vinylidene chain end ratio of more than 2:1, more than 2.5:1, more than 3:1, more than 5:1, or more than 10:1, and further optionally, an allyl chain end to vinylene chain end ratio of greater than 10:1 (preferably greater than 15:1, or greater than 20:1); and even further optionally preferably substantially no isobutyl chain ends (preferably less than 0.1 wt % isobutyl chain ends). For further information on such VTM's please see concurrently filed U.S. Ser. No. 13/072,249, filed Mar. 25, 2011, entitled "Vinyl Terminated Higher Olefin Copolymers and Methods to Produce Thereof."

In particular embodiments herein, the invention relates to a composition comprising vinyl terminated polyolefins having an Mn of at least 200 g/mol, (preferably 200 to 100,000 g/mol, preferably 200 to 75,000 g/mol, preferably 200 to 60,000 g/mol, preferably 300 to 60,000 g/mol, or preferably 750 to 30,000 g/mol) (measured by $^1$H NMR) comprising of one or more (preferably two or more, three or more, four or more, and the like) $C_4$ to $C_{40}$ (preferably $C_4$ to $C_{30}$, $C_4$ to $C_{20}$, or $C_4$ to $C_{12}$, preferably butene, pentene, hexene, heptene, octene, nonene, decene, undecene, dodecene, norbornene, cyclopentene, cycloheptene, cyclooctene, cyclooctadiene, cyclododecene, 7-oxanorbornene, 7-oxanorbornadiene, substituted derivatives thereof, and isomers thereof) higher olefin derived units, where the vinyl terminated higher olefin polymer comprises substantially no propylene derived units (preferably less than 0.1 wt % propylene); and wherein the higher olefin polymer has at least 5% (at least 10%, at least 15%, at least 20%, at least 30%, at least 40%, at least 50%, at least 60%, at least 70% allyl; at least 80%, at least 90%, or at least 95%) allyl chain ends; and optionally, an allyl chain end to vinylidene chain end ratio of greater than 2:1 (preferably greater than 2.5:1, greater than 3:1, greater than 5:1, or greater than 10:1); and further optionally, an allyl chain end to vinylene chain end ratio of greater than 10:1 (preferably greater than 15:1, or greater than 20:1); and even further optionally preferably substantially no isobutyl chain ends (preferably less than 0.1 wt % isobutyl chain ends). In some embodiments, these higher olefin vinyl terminated polymers may comprise ethylene derived units, preferably at least 5 mol % ethylene (preferably at least 15 mol % ethylene, preferably at least 25 mol % ethylene, preferably at least 35 mol % ethylene, preferably at least 45 mol % ethylene, preferably at least 60 mol % ethylene, preferably at least 75 mol % ethylene, or preferably at least 90 mol % ethylene). For further information on such vinyl terminated polyolefins please see concurrently filed U.S. Ser. No. 13/072,288, filed Mar. 25, 2011, entitled "Vinyl Terminated Higher Olefin Polymers and Methods to Produce Thereof."

In another embodiment, the vinyl terminated polyolefin useful herein is a branched polyolefin having an Mn of 7,500 to 60,000 g/mol (and optionally a Tm of greater than 60° C. (preferably greater than 100° C.), and/or, optionally, a ΔHf of greater than 7 J/g (preferably greater than 50 J/g)) comprising one or more alpha olefins (preferably ethylene and/or propylene and optionally a $C_4$ to $C_{10}$ alpha olefin), said branched polyolefin having: (i) 50 mol % or greater allyl chain ends, relative to total unsaturated chain ends (preferably 60% or more, preferably 70% or more, preferably 75% or more, preferably 80% or more, preferably 90% or more, preferably 95% or more); (ii) a g'(vis) of 0.90 or less (preferably 0.85 or less, preferably 0.80 or less); (iii), optionally, an allyl chain end to internal vinylidene ratio of greater than 5:1 (preferably greater than 10:1); (iv) optionally, an allyl chain end to vinylidene chain end ratio of greater than 10:1 (preferably greater than 15:1).

In another embodiment, the vinyl terminated polyolefin useful herein is a branched polyolefin having an Mn of 60,000 g/mol or more (and optionally a Tm of greater than 60° C. (preferably greater than 100° C.), and/or, optionally, a ΔHf of greater than 7 J/g (preferably greater than 50 J/g)) comprising one or more alpha olefins (preferably ethylene and/or propylene and optionally a $C_4$ to $C_{10}$ alpha olefin), and having: (i) 50 mol % or greater allyl chain ends, relative to total unsaturated chain ends (preferably 60% or more, preferably 70% or more, preferably 75% or more, preferably 80% or more, preferably 90% or more, preferably 95% or more); (ii) a g'(vis) of 0.90 or less (preferably 0.85 or less, preferably 0.80 or less); (iii) a bromine number which, upon complete hydrogenation, decreases by at least 50% (preferably at least 75%); (iv), optionally, an allyl chain end to internal vinylidene ratio of greater than 5:1 (preferably greater than 10:1); (v) optionally, an allyl chain end to vinylidene chain end ratio of greater than 10:1 (preferably greater than 15:1).

In another embodiment, the vinyl terminated polyolefin useful herein is a branched polyolefin having an Mn of less than 7,500 g/mol, preferably from 100 to 7,000 g/mol, preferably form 400 to 6,500 g/mol (and optionally a Tm of greater than 60° C. (preferably greater than 100° C.), and/or, optionally, a ΔHf of greater than 7 J/g (preferably greater than 50 J/g) comprising one or more alpha olefins (preferably ethylene and/or propylene and optionally a $C_4$ to $C_{10}$ alpha olefin), and having: (i) 50 mol % or greater allyl chain ends, relative to total unsaturated chain ends (preferably 60% or more, preferably 70% or more, preferably 80% or more, preferably 90% or more, preferably 95% or more); (ii) a ratio of percentage of saturated chain ends to percentage of allyl chain ends of 1.2 to 2.0, preferably a ratio of percentage of saturated chain ends (preferably isobutyl chain ends) to percentage of allyl chain ends of 1.6 to 1.8, wherein the percentage of saturated chain ends is determined using $^{13}$C NMR as described in WO 2009/155471 at paragraph [0095] and [0096] except that the spectra are referenced to the chemical shift of the solvent, tetrachloroethane-$d_2$, and/or a ratio of Mn(GPC)/Mn($^1$H NMR) of 0.95 or less (preferably 0.90 or less, preferably 0.85 or less, preferably 0.80 or less); and (iii) optionally, a bromine number which, upon complete hydrogenation, decreases by at least 50% (preferably by at least 75%); (iv), optionally, an allyl chain end to internal vinylidene ratio of greater than 5:1 (preferably greater than 10:1); (v) optionally, an allyl chain end to vinylidene chain end ratio of greater than 2:1 (preferably greater than 10:1), preferably the branched vinyl terminated polyolefin has a ratio of Mn(GPC)/Mn($^1$H NMR) of 0.95 or less (preferably 0.90 or less, preferably 0.85 or less, preferably 0.80 or less).

$C_4$ to $C_{10}$ alpha olefin monomers useful in the branched polymers described above include butene, pentene, hexene, heptene, octene, nonene, decene, cyclopentene, cycloheptene, cyclooctene, and isomers thereof.

For more information on useful branched polymers and methods to produce them, please see concurrently filed U.S. Ser. No. 61/467,681, filed Mar. 25, 2011, entitled "Branched Vinyl Terminated Polymers and Methods for Production Thereof".

Any of the vinyl terminated polyolefins described herein preferably have less than 1400 ppm aluminum, preferably less than 1000 ppm aluminum, preferably less than 500 ppm aluminum, preferably less than 100 ppm aluminum, preferably less than 50 ppm aluminum, preferably less than 20 ppm aluminum, preferably less than 5 ppm aluminum.

The "isobutyl chain end to allylic vinyl group ratio" is defined to be the ratio of the percentage of isobutyl chain ends to the percentage of allylic vinyl groups.

In a preferred embodiment, the vinyl terminated polyolefin (preferably a propylene oligomer) comprises less than 3 wt % of functional groups selected from hydroxide, aryls and substituted aryls, halogens, alkoxys, carboxylates, esters, acrylates, oxygen, and carboxyl, preferably less than 2 wt %, more preferably less than 1 wt %, more preferably less than 0.5 wt %, more preferably less than 0.1 wt %, more preferably 0 wt %, based upon the weight of the vinyl terminated polyolefin.

In a preferred embodiment, the vinyl terminated polyolefin is an oligomer having an $M_n$ as determined by $^1$H NMR of 150 to 25,000 g/mole, 200 to 20,000 g/mol, preferably 250 to 15,000 g/mol, preferably 300 to 15,000 g/mol, preferably 400 to 12,000 g/mol, preferably 750 to 10,000 g/mol. Further a desirable molecular weight range can be any combination of any upper molecular weight limit with any lower molecular weight limit described above. $M_n$ is determined according to the methods described below in the examples section.

In a preferred embodiment, the vinyl terminated polyolefin preferably has a glass transition temperature (Tg) of less than 0° C. or less (as determined by differential scanning calorimetry as described below), preferably −10° C. or less, more preferably −20° C. or less, more preferably −30° C. or less, more preferably −50° C. or less.

In a preferred embodiment, the vinyl terminated polyolefin preferably contains less than 80 wt % of $C_4$ olefin(s), (such as isobutylene n-butene, 2-butene, isobutylene, and butadiene), based upon the weight of the vinyl terminated polyolefin, preferably less than 10 wt %, preferably 5 wt %, preferably less than 4 wt %, preferably less than 3 wt %, preferably less than 2 wt %, preferably less than 1 wt %, preferably less than 0.5 wt %, preferably less than 0.25 wt % of $C_4$ olefin(s) based upon the weight of the vinyl terminated polyolefin.

Alternately, the vinyl terminated polyolefin preferably contains less than 20 wt % of $C_4$ or more olefin(s), (such as $C_4$ to $C_{30}$ olefins, typically such as $C_4$ to $C_{12}$ olefins, typically such as $C_4$, $C_6$, $C_8$, $C_{12}$, olefins, etc.), based upon the weight of the vinyl terminated polyolefin, preferably less than 10 wt %, preferably 5 wt %, preferably less than 4 wt %, preferably less than 3 wt %, preferably less than 2 wt %, preferably less than 1 wt %, preferably less than 0.5 wt %, preferably less than 0.25 wt % of $C_4$ olefin(s) based upon the weight of the vinyl terminated polyolefin, as determined by $^{13}$C NMR.

In another embodiment, the vinyl terminated polyolefin composition produced comprises less than 20 wt % dimer and trimer (preferably less than 10 wt %, preferably less than 5 wt %, more preferably less than 2 wt %, based upon the weight of the vinyl terminated polyolefin composition), as measured by GC. Products are analyzed by gas chromatography (Agilent 6890N with auto-injector) using helium as a carrier gas at 38 cm/sec. A column having a length of 60 m (J & W Scientific DB-1, 60 m×0.25 mm I.D.x 1.0 μm film thickness) packed with a flame ionization detector (FID), an Injector temperature of 250° C., and a Detector temperature of 250° C. are used. The sample was injected into the column in an oven at 70° C., then heated to 275° C. over 22 minutes (ramp rate 10° C./min to 100° C., 30° C./min to 275° C., hold). An internal standard, usually the monomer, is used to derive the amount of dimer or trimer product that is obtained. Yields of dimer and trimer product are calculated from the data recorded on the spectrometer. The amount of dimer or trimer product is calculated from the area under the relevant peak on the GC trace, relative to the internal standard.

In another embodiment, the vinyl terminated polyolefin produced here contains less than 25 ppm hafnium, preferably less than 10 ppm hafnium, preferably less than 5 ppm hafnium based on the yield of polymer produced and the mass of catalyst employed.

Particularly useful vinyl terminated polyolefins may be isotactic, highly isotactic, syndiotactic, or highly syndiotactic propylene polymer, particularly isotactic polypropylene. As used herein, "isotactic" is defined as having at least 10% isotactic pentads, preferably having at least 40% isotactic pentads of methyl groups derived from propylene according to analysis by $^{13}$C NMR. As used herein, "highly isotactic" is defined as having at least 60% isotactic pentads according to analysis by $^{13}$C NMR. In a desirable embodiment, the amine functionalized polyolefin (preferably polypropylene) has at least 85% isotacticity. As used herein, "syndiotactic" is defined as having at least 10% syndiotactic pentads, preferably at least 40%, according to analysis by $^{13}$C NMR. As used herein, "highly syndiotactic" is defined as having at least 60% syndiotactic pentads according to analysis by $^{13}$C NMR. In another embodiment, the amine functionalized polyolefin (preferably polypropylene) has at least 85% syndiotacticity.

In a preferred embodiment, little or no alumoxane is used in the process to produce the vinyl terminated macromers. Preferably, alumoxane is present at zero mol %, alternately the alumoxane is present at a molar ratio of aluminum to transition metal less than 500:1, preferably less than 300:1, preferably less than 100:1, preferably less than 1:1.

In an alternate embodiment, if an alumoxane is used to produce the vinyl terminated polyolefins then, the alumoxane has been treated to remove free alkyl aluminum compounds, particularly trimethyl aluminum.

In a preferred embodiment, little or no scavenger is used in the process to produce the vinyl terminated macromers. Preferably, scavenger is present at zero mol %, alternately the scavenger is present at a molar ratio of scavenger metal to transition metal of less than 100:1, preferably less than 50:1, preferably less than 15:1, preferably less than 10:1.

In a preferred embodiment, the vinyl terminated macromer used herein comprises at least 10 mol % (alternately at least 20 mol %, alternately at least 40 mol %, alternately at least 60 mol %) of a $C_4$ or greater olefin (such as butene, pentene, octene, nonene, decene, undecene, dodecene) and has: 1) at least 30% allyl chain ends (relative to total unsaturations), preferably at least 40%, preferably at least 50%, preferably at least 60%, preferably at least 70%, preferably at least 75%, preferably at least 80%, preferably at least 85%, preferably at least 90%, preferably at least 95% allyl chain ends (relative to total unsaturations); and 2) an Mn of from 200 to 60,000 g/mol, preferably from 200 to 50,000 g/mol, preferably from 500 to 40,000 g/mol.

In another embodiment, the vinyl terminated polyolefins described herein may have a melting point (DSC first melt) of from 60° C. to 175° C., alternately 50° C. to 100° C. In another embodiment, the vinyl terminated polyolefins described herein have no detectable melting point by DSC following storage at ambient temperature (23° C.) for at least 48 hours.

For more information on useful vinyl terminated polyolefins useful herein please see U.S. Ser. No. 12/143,663, filed Jun. 20, 2008.

Melting temperature ($T_m$) and glass transition temperature (Tg) are measured using Differential Scanning calorimetry (DSC) using commercially available equipment such as a TA Instruments 2920 DSC. Typically, 6 to 10 mg of the sample, that has been stored at room temperature for at least 48 hours, is sealed in an aluminum pan and loaded into the instrument at room temperature. The sample is equilibrated at 25° C., then it is cooled at a cooling rate of 10° C./min to −80° C. The sample is held at −80° C. for 5 min and then heated at a heating rate of 10° C./min to 25° C. The glass transition temperature is measured from the heating cycle. Alternatively, the sample is equilibrated at 25° C., then heated at a heating rate of 10° C./min to 150° C. The endothermic melting transition, if present, is analyzed for onset of transition and peak temperature. The melting temperatures reported are the peak melting temperatures from the first heat unless otherwise specified. For samples displaying multiple peaks, the melting point (or melting temperature) is defined to be the peak melting temperature (i.e., associated with the largest endothermic calorimetric response in that range of temperatures) from the DSC melting trace.

In another embodiment, the oligomers described herein are a liquid at 25° C. In another embodiment, the vinyl terminated polymers described herein have a viscosity at 60° C. of greater than 1000 cP, greater than 12,000 cP, or greater than 100,000 cP. In other embodiments, the vinyl terminated polymers have a viscosity of less than 200,000 cP, less than 150,000 cP, or less than 100,000 cP. Viscosity is measured using a Brookfield Digital Viscometer.

In another embodiment, any of the vinyl terminated polyolefins described or useful herein have 3-alkyl vinyl end groups (where the alkyl is a C1 to C38 alkyl), also referred to as a "3-alkyl chain ends" or a "3-alkyl vinyl termination", represented by the formula:

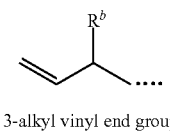

3-alkyl vinyl end group where "••••" represents the polyolefin chain and $R^b$ is a C1 to C38 alkyl group, preferably a $C_1$ to $C_{20}$ alkyl group, such as methyl, ethyl, propyl, butyl, pentyl, hexyl, heptyl, octyl, nonyl, decyl, undecyl, docecyl, and the like. The amount of 3-alkyl chain ends is determined using $^{13}C$ NMR as set out below.

In a preferred embodiment, any of the vinyl terminated polyolefins described or useful herein have at least 5% 3-alkyl chain ends (preferably at least 10% 3-alkyl chain ends, at least 20% 3-alkyl chain ends, at least 30% 3-alkyl chain ends; at least 40% 3-alkyl chain ends, at least 50% 3-alkyl chain ends, at least 60% 3-alkyl chain ends, at least 70% 3-alkyl chain ends; at least 80% 3-alkyl chain ends, at least 90% 3-alkyl chain ends; at least 95% 3-alkyl chain ends, relative to total unsaturation.

In a preferred embodiment, any of the vinyl terminated polyolefins described or useful herein have at least 5% of 3-alkyl+allyl chain ends, (e.g., all 3-alkyl chain ends plus all allyl chain ends), preferably at least 10% 3-alkyl+allyl chain ends, at least 20% 3-alkyl+allyl chain ends, at least 30% 3-alkyl+allyl chain ends; at least 40% 3-alkyl+allyl chain ends, at least 50% 3-alkyl+allyl chain ends, at least 60% 3-alkyl+allyl chain ends, at least 70% 3-alkyl+allyl chain ends; at least 80%3-alkyl+allyl chain ends, at least 90% 3-alkyl+allyl chain ends; at least 95% 3-alkyl+allyl chain ends, relative to total unsaturation.

In another embodiment, the oligomers described herein have an Mw (measured as described below) of 1,000 to about 30,000 g/mol, alternately 2000 to 25,000 g/mol, alternately 3,000 to 20,000 g/mol and/or an Mz of about 1700 to about 150,000 g/mol, alternately 800 to 100,000 g/mol.

Mw, Mn, Mz, number of carbon atoms, and $g'_{vis}$ are determined by Gel Permeation Chromatography (GPC) using a High Temperature Size Exclusion Chromatograph (either from Waters Corporation or Polymer Laboratories), equipped with three in-line detectors, a differential refractive index detector (DRI), a light scattering (LS) detector, and a viscometer. Experimental details, including detector calibration, are described in: T. Sun, P. Brant, R. R. Chance, and W. W. Graessley, Macromolecules, Vol. 34, No. 19, 6812-6820, (2001) and references therein. Three Polymer Laboratories PLgel 10 mm Mixed-B LS columns are used. The nominal flow rate is 0.5 cm³/min, and the nominal injection volume is 300 μL. The various transfer lines, columns and differential refractometer (the DRI detector) are contained in an oven maintained at 145° C. Solvent for the experiment is prepared by dissolving 6 grams of butylated hydroxy toluene as an antioxidant in 4 liters of Aldrich reagent grade 1, 2, 4 trichlorobenzene (TCB). The TCB mixture is then filtered through a 0.7 μm glass pre-filter and subsequently through a 0.1 μm Teflon filter. The TCB is then degassed with an online degasser before entering the Size Exclusion Chromatograph. Polymer solutions are prepared by placing dry polymer in a glass container, adding the desired amount of TCB, then heating the mixture at 160° C. with continuous agitation for about 2 hours. All quantities are measured gravimetrically. The TCB densities used to express the polymer concentration in mass/volume units are 1.463 g/ml at room temperature and 1.324 g/ml at 145° C. The injection concentration is from 0.75 to 2.0 mg/ml, with lower concentrations being used for higher molecular weight samples. Prior to running each sample the DRI detector and the injector are purged. Flow rate in the apparatus is then increased to 0.5 ml/minute, and the DRI is allowed to stabilize for 8 to 9 hours before injecting the first sample. The LS laser is turned on 1 to 1.5 hours before running the samples. The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the refractive index increment for the system. The refractive index, n=1.500 for TCB at 145° C. and λ=690 nm. For purposes of this invention and the claims thereto (dn/dc)=0.104 for propylene polymers, 0.098 for butene polymers and 0.1 otherwise. Units on parameters throughout this description of the SEC method are such that concentration is expressed in g/cm³, molecular weight is expressed in g/mole, and intrinsic viscosity is expressed in dL/g.

The LS detector is a Wyatt Technology High Temperature mini-DAWN. The molecular weight, M, at each point in the chromatogram is determined by analyzing the LS output using the Zimm model for static light scattering (M. B. Huglin, LIGHT SCATTERING FROM POLYMER SOLUTIONS, Academic Press, 1971):

$$\frac{K_o c}{\Delta R(\theta)} = \frac{1}{MP(\theta)} + 2A_2 c$$

Here, $\Delta R(\theta)$ is the measured excess Rayleigh scattering intensity at scattering angle $\theta$, c is the polymer concentration determined from the DRI analysis, $A_2$ is the second virial coefficient for purposes of this invention, $A_2$=0.0006 for propylene polymers, 0.0015 for butene polymers and 0.001 otherwise, (dn/dc)=0.104 for propylene polymers, 0.098 for butene polymers and 0.1 otherwise, $P(\theta)$ is the form factor for a monodisperse random coil, and $K_O$ is the optical constant for the system:

$$K_o = \frac{4\pi^2 n^2 (dn/dc)^2}{\lambda^4 N_A}$$

where $N_A$ is Avogadro's number, and (dn/dc) is the refractive index increment for the system. The refractive index, n=1.500 for TCB at 145° C. and $\lambda$=690 nm.

A high temperature Viscotek Corporation viscometer, which has four capillaries arranged in a Wheatstone bridge configuration with two pressure transducers, is used to determine specific viscosity. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, $[\eta]$, at each point in the chromatogram is calculated from the following equation:

$$\eta_s = c[\eta] + 0.3(c[\eta])^2$$

where c is concentration and was determined from the DRI output.

The branching index ($g'_{vis}$) is calculated using the output of the SEC-DRI-LS-VIS method as follows. The average intrinsic viscosity, $[\eta]_{avg}$, of the sample is calculated by:

$$[\eta]_{avg} = \frac{\sum c_i [\eta]_i}{\sum c_i}$$

where the summations are over the chromatographic slices, i, between the integration limits.

The branching index $g'_{vis}$ is defined as:

$$g'vis = \frac{[\eta]_{avg}}{kM_v^\alpha}$$

where, for purpose of this invention and claims thereto, $\alpha$=0.695 and k=0.000579 for linear ethylene polymers, $\alpha$=0.705 k=0.000262 for linear propylene polymers, and $\alpha$=0.695 and k=0.000181 for linear butene polymers. $M_v$ is the viscosity-average molecular weight based on molecular weights determined by LS analysis. See Macromolecules, 2001, 34, 6812-6820 and Macromolecules, 2005, 38, 7181-7183, for guidance on selecting a linear standard having similar molecular weight and comonomer content, and determining k coefficients and a exponents.

Molecular weight distribution (Mw by GPC-DRI divided by Mn by GPC-DRI) is determined by the method above. In some embodiments, the polyolefins of this invention have an Mw/Mn (by GPC-DRI) of 1.5 to 20, alternately 1.7 to 10.

Process to Make Vinyl Terminated Polyolefins

The vinyl terminated polyolefins described above are typically prepared in a homogeneous process, preferably a bulk process, as described in U.S. Ser. No. 12/143,663, filed on Jun. 20, 2008, which is incorporated by reference herein.

Vinyl terminated polyolefins may also be produced using the processes (and catalyst compounds and/or activators) disclosed in concurrently filed U.S. Ser. No. 13/072,280, filed Mar. 25, 2011, entitled "Novel Catalysts and Methods of Use Thereof to Produce Vinyl Terminated Polymers" and U.S. Ser. No. 13/072,279, filed Mar. 25, 2011, entitled "Enhanced Catalyst Performance for Production of Vinyl Terminated Propylene and Ethylene/Propylene Macromers". Useful vinyl terminated polyolefins can also be produced using the processes disclosed in concurrently filed U.S. Ser. No. 13/072,288, filed Mar. 25, 2011, entitled "Vinyl Terminated Higher Olefin Polymers and Methods to Produce Thereof", and concurrently filed U.S. Ser. No. 13/072,249, filed Mar. 25, 2011, entitled "Vinyl Terminated Higher Olefin Copolymers and Methods to Produce Thereof", and concurrently filed U.S. Ser. No. 61/467,681, filed Mar. 25, 2011, entitled "Branched Vinyl Terminated Polymers and Methods for Production Thereof".

In a preferred embodiment, one, two, three or more $C_2$ to $C_{40}$ alpha olefins, such as ethylene, propylene, butene, pentene, hexene, octene, decene and dodecene (preferably ethylene and/or propylene) and optional comonomers (such as one, two or three or more of ethylene, butene, hexene, octene, decene and dodecene) can be polymerized/polymerized by reacting a catalyst system (comprising metallocene compound(s), and one or more activators) with the olefins. Other additives may also be used, as desired, such as scavengers and/or hydrogen. Any conventional suspension, homogeneous bulk, solution, slurry, or high-pressure polymerization process can be used. Such processes can be run in a batch, semi-batch, or continuous mode. Such processes and modes are well known in the art. Homogeneous polymerization processes are preferred. A bulk homogeneous process is particularly preferred. Alternately no solvent or diluent is present or added in the reaction medium, (except for the small amounts used as the carrier for the catalyst system or other additives, or amounts typically found with the monomer; e.g., propane in propylene).

Suitable diluents/solvents for polymerization include non-coordinating, inert liquids. Examples include straight and branched-chain hydrocarbons such as isobutane, butane, pentane, isopentane, hexanes, isohexane, heptane, octane, dodecane, and mixtures thereof; cyclic and alicyclic hydrocarbons such as cyclohexane, cycloheptane, methylcyclohexane, methylcycloheptane, and mixtures thereof such as can be found commercially (Isopars); perhalogenated hydrocarbons such as perfluorinated $C_{4-10}$ alkanes, chlorobenzene, and aromatic and alkylsubstituted aromatic compounds such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, and 1-decene. Mixtures of the foregoing are also suitable. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably at 0 wt % based upon the weight of the solvents.

In a preferred embodiment, the feed concentration for the polymerization is 60 vol % solvent or less, preferably 40 vol % or less, preferably 20 vol % or less. Preferably the polymerization is run in a bulk process.

In some embodiments, where butene is the comonomer, the butene source may be a mixed butene stream comprising various isomers of butene. The 1-butene monomers are expected to be preferentially consumed by the polymerization process. Use of such mixed butene streams will provide an economic benefit, as these mixed streams are often waste streams from refining processes, for example $C_4$ raffinate streams, and can therefore be substantially less expensive than pure 1-butene.

Suitable additives to the polymerization process can include one or more scavengers, promoters, modifiers, reducing agents, oxidizing agents, hydrogen, aluminum alkyls, or silanes.

In a preferred embodiment, little or no scavenger is used in the process to produce the vinyl terminated polyolefin. Preferably, scavenger is present at zero mol %, alternately the scavenger is present at a molar ratio of scavenger metal to transition metal of less than 100:1, preferably less than 50:1, preferably less than 15:1, preferably less than 10:1.

In a preferred embodiment, hydrogen is present in the polymerization reactor at a partial pressure of 0.001 to 50 psig (0.007 to 345 kPa), preferably from 0.01 to 25 psig (0.07 to 172.4 kPa), more preferably 0.1 to 10 psig (0.7 to 68.95 kPa). It has been found that in the present systems, hydrogen can be used to provide increased activity without significantly impairing the catalyst's ability to produce allylic chain ends. Preferably the catalyst activity (calculated as g/mmolcatalyst/hr) is at least 20% higher than the same reaction without hydrogen present, preferably at least 50% higher, preferably at least 100% higher.

"Catalyst productivity" is a measure of how many grams of polymer (P) are produced using a polymerization catalyst comprising W g of catalyst (cat), over a period of time of T hours; and may be expressed by the following formula: P/(T×W) and expressed in units of gPgcat$^{-1}$hr$^{-1}$. Conversion is the amount of monomer that is converted to polymer product, and is reported as mol % and is calculated based on the polymer yield and the amount of monomer fed into the reactor. Catalyst activity is a measure of how active the catalyst is and is reported as the mass of product polymer (P) produced per mole of catalyst (cat) used (kgP/molcat).

In an alternate embodiment, the activity of the catalyst is at least 50 g/mmol/hour, preferably 500 or more g/mmol/hour, preferably 5000 or more g/mmol/hr, preferably 50,000 or more g/mmol/hr. In an alternate embodiment, the conversion of olefin monomer is at least 10%, based upon polymer yield and the weight of the monomer entering the reaction zone, preferably 20% or more, preferably 30% or more, preferably 50% or more, preferably 80% or more. In an alternate embodiment, the productivity at least 4500 g/mmol/hour, preferably 5000 or more g/mmol/hour, preferably 10,000 or more g/mmol/hr, preferably 50,000 or more g/mmol/hr. In an alternate embodiment, the productivity is at least 80,000 g/mmol/hr, preferably at least 150,000 g/mmol/hr, preferably at least 200,000 g/mmol/hr, preferably at least 250,000 g/mmol/hr, preferably at least 300,000 g/mmol/hr.

Preferred polymerizations can be run at typical temperatures and/or pressures, such as from 25° C. to 150° C., preferably 40° C. to 120° C., preferably 45° C. to 80° C., and preferably from 0.35 to 10 MPa, preferably from 0.45 to 6 MPa, preferably from 0.5 to 4 MPa.

In a typical polymerization, the residence time of the reaction is up to 60 minutes, preferably between 5 to 50 minutes, preferably 10 to 40 minutes.

In a preferred embodiment hydrogen is present in the polymerization reactor at a partial pressure of 0.001 to 50 psig (0.007 to 345 kPa), preferably from 0.01 to 25 psig (0.07 to 172 kPa), more preferably 0.1 to 10 psig (0.7 to 70 kPa). It has been found that in the present systems, hydrogen can be used to provide increased activity without significantly impairing the catalyst's ability to produce allylic chain ends. Preferably the catalyst activity (calculated as g/mmol catalyst/hr) is at least 20% higher than the same reaction without hydrogen present, preferably at least 50% higher, preferably at least 100% higher.

In a preferred embodiment, little or no alumoxane is used in the process to produce the vinyl terminated polymers. Preferably, alumoxane is present at zero mole %, alternately the alumoxane is present at a molar ratio of aluminum to transition metal less than 500:1, preferably less than 300:1, preferably less than 100:1, preferably less than 1:1.

In an alternate embodiment, if an alumoxane is used to produce the vinyl terminated polymers then, the alumoxane has been treated to remove free alkyl aluminum compounds, particularly trimethyl aluminum.

Further, in a preferred embodiment, the activator used herein to produce the vinyl terminated polymer is a bulky activator as defined herein and is discrete.

In a preferred embodiment, little or no scavenger is used in the process to produce the vinyl terminated polymers. Preferably, scavenger (such as tri alkyl aluminum) is present at zero mole %, alternately the scavenger is present at a molar ratio of scavenger metal to transition metal of less than 100:1, preferably less than 50:1, preferably less than 15:1, preferably less than 10:1.

In a preferred embodiment, the polymerization: 1) is conducted at temperatures of 0 to 300° C. (preferably 25 to 150° C., preferably 40 to 120° C., preferably 45 to 80° C.), and 2) is conducted at a pressure of atmospheric pressure to 10 MPa (preferably 0.35 to 10 MPa, preferably from 0.45 to 6 MPa, preferably from 0.5 to 4 MPa), and 3) is conducted in an aliphatic hydrocarbon solvent (such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof; preferably where aromatics are present in the solvent at less than 1 wt %, preferably at less than 0.5 wt %, preferably at 0 wt % based upon the weight of the solvents); and 4) wherein the catalyst system used in the polymerization comprises less than 0.5 mol %, preferably 0 mol % alumoxane, alternately the alumoxane is present at a molar ratio of aluminum to transition metal less than 500:1, preferably less than 300:1, preferably less than 100:1, preferably less than 1:1); and 5) the polymerization occurs in one reaction zone; and 6) the productivity of the catalyst compound is at least 80,000 g/mmol/hr (preferably at least 150,000 g/mmol/hr, preferably at least 200,000 g/mmol/hr, preferably at least 250,000 g/mmol/hr, preferably at least 300,000 g/mmol/hr); and 7) optionally scavengers (such as trialkyl aluminum compounds) are absent (e.g. present at zero mole %, alternately the scavenger is present at a molar ratio of scavenger metal to transition metal of less than 100:1, preferably less than 50:1, preferably less than 15:1, preferably less than 10:1); and 8) optionally hydrogen is present in the polymerization reactor at a partial pressure of 0.001 to 50 psig (0.007 to 345 kPa) (preferably from 0.01 to 25 psig (0.07 to 172 kPa), more preferably 0.1 to 10 psig (0.7 to 70 kPa)). In preferred embodiment, the catalyst system used in the polymerization comprises no more than one catalyst compound. A "reaction zone" also referred to as a "polymerization zone" is a vessel where polymerization takes place, for example a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In a preferred embodiment, the polymerization occurs in one reaction zone. Room temperature is 23° C. unless otherwise noted.

Catalyst Compounds to Make Vinyl Terminated Polyolefins

Catalyst compounds useful herein to produce the vinyl terminated polyolefins include one or more metallocene compound(s) represented by the formulae:

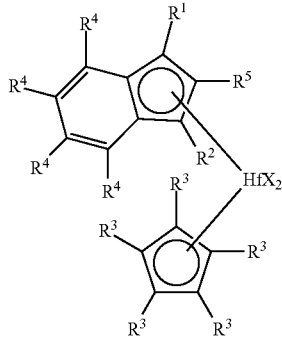

I

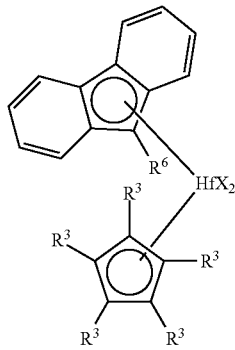

II

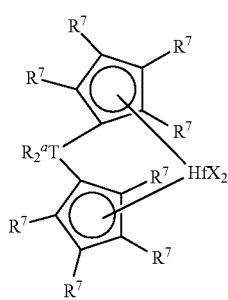

III

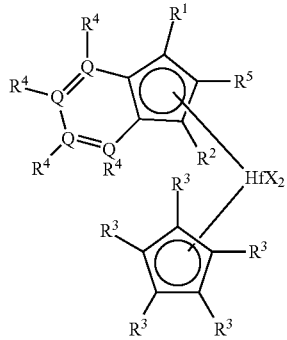

IV where
Hf is hafnium;
each X is, independently, selected from the group consisting of hydrocarbyl radicals having from 1 to 20 carbon atoms, hydrides, amides, alkoxides, sulfides, phosphides, halogens, dienes, amines, phosphines, ethers, or a combination thereof, preferably methyl, ethyl, propyl, butyl, phenyl, benzyl, chloride, bromide, iodide, (alternately two X's may form a part of a fused ring or a ring system);
each Q is, independently carbon or a heteroatom, preferably C, N, P, S (preferably at least
one Q is a heteroatom, alternately at least two Q's are the same or different heteroatoms, alternately at least three Q's are the same or different heteroatoms, alternately at least four Q's are the same or different heteroatoms);
each $R^1$ is, independently, hydrogen or a $C_1$ to $C_8$ alkyl group, preferably a $C_1$ to $C_8$ linear alkyl group, preferably methyl ethyl, propyl, butyl, pentyl, hexyl, heptyl or octyl, $R^1$ may the same or different as $R^2$;
each $R^2$ is, independently, hydrogen or a $C_1$ to $C_8$ alkyl group, preferably a $C_1$ to $C_8$ linear alkyl group, preferably methyl ethyl, propyl, butyl, pentyl, hexyl, heptyl or octyl, provided that at least one of $R^1$ or $R^2$ is not hydrogen, preferably both of $R^1$ and $R^2$ are not hydrogen, preferably $R^1$ and/or $R^2$ are not branched;
each $R^3$ is, independently, hydrogen, or a substituted or unsubstituted hydrocarbyl group having from 1 to 8 carbon atoms, preferably 1 to 6 carbon atoms, preferably a substituted or unsubstituted $C_1$ to $C_8$ linear alkyl group, preferably methyl ethyl, propyl, butyl, pentyl, hexyl, heptyl, octyl, provided however that at least three $R^3$ groups are not hydrogen (alternately four $R^3$ groups are not hydrogen, alternately five $R^3$ groups are not hydrogen);
{Alternately, when the catalyst compound is to used to make the homo-polymer then each $R^3$ is, independently, hydrogen, or a substituted or unsubstituted hydrocarbyl group having from 1 to 8 carbon atoms, preferably 1 to 6 carbon atoms, preferably a substituted or unsubstituted $C_1$ to $C_8$ linear alkyl group, preferably methyl ethyl, propyl, butyl, pentyl, hexyl, heptyl, octyl, provided however that: 1) all five $R^3$ groups are methyl, or 2) four $R^3$ groups are not hydrogen and at least one $R^3$ group is a $C_2$ to $C_8$ substituted or unsubstituted hydrocarbyl (preferably at least two, three, four or five $R^3$ groups are a $C_2$ to $C_8$ substituted or unsubstituted hydrocarbyl)};
each $R^4$ is, independently, hydrogen or a substituted or unsubstituted hydrocarbyl group, a heteroatom or heteroatom containing group, preferably a substituted or unsubstituted hydrocarbyl group having from 1 to 20 carbon atoms, preferably 1 to 8 carbon atoms, preferably a substituted or unsubstituted $C_1$ to $C_8$ linear alkyl group, preferably methyl ethyl, propyl, butyl, pentyl, hexyl, heptyl, octyl, substituted phenyl (such as propyl phenyl), phenyl, silyl, substituted silyl, (such as $CH_2SiR'$, where R' is a $C_1$ to $C_{12}$ hydrocarbyl, such as methyl, ethyl, propyl, butyl, phenyl);

$R^5$ is hydrogen or a $C_1$ to $C_8$ alkyl group, preferably a $C_1$ to $C_8$ linear alkyl group, preferably methyl, ethyl, propyl, butyl, pentyl, hexyl, heptyl or octyl;

$R^6$ is hydrogen or a $C_1$ to $C_8$ alkyl group, preferably a $C_1$ to $C_8$ linear alkyl group, preferably methyl, ethyl, propyl, butyl, pentyl, hexyl, heptyl or octyl;

each $R^7$ is, independently, hydrogen, or a $C_1$ to $C_8$ alkyl group, preferably a $C_1$ to $C_8$ linear alkyl group, preferably methyl ethyl, propyl, butyl, pentyl, hexyl, heptyl or octyl, provided however that at least seven $R^7$ groups are not hydrogen, alternately at least eight $R^7$ groups are not hydrogen, alternately all $R^7$ groups are not hydrogen, (preferably the $R^7$ groups at the 3 and 4 positions on each Cp ring of Formula IV are not hydrogen);

N is nitrogen;

$R_2^aT$ is a bridge, preferably T is Si or Ge, preferably Si, and each $R^a$, is independently, hydrogen, halogen or a $C_1$ to $C_{20}$ hydrocarbyl, such as methyl, ethyl, propyl, butyl, pentyl, hexyl, heptyl, octyl, phenyl, benzyl, substituted phenyl, and two $R^a$ can form a cyclic structure including aromatic, partially saturated, or saturated cyclic or fused ring system; and further provided that any two adjacent R groups may form a fused ring or multicenter fused ring system where the rings may be aromatic, partially saturated or saturated.

In an alternate embodiment, at least one $R^4$ group is not hydrogen, alternately at least two $R^4$ groups are not hydrogen, alternately at least three $R^4$ groups are not hydrogen, alternately at least four $R^4$ groups are not hydrogen, alternately all $R^4$ groups are not hydrogen.

Catalyst compounds that are particularly useful in this invention include one or more of: (1,3-Dimethylindenyl)(pentamethylcyclopentadienyl) hafniumdimethyl, (1,3,4,7-Tetramethylindenyl) (pentamethylcyclopentadienyl)hafniumdimethyl, (1,3- Dimethylindenyl)(tetramethylcyclopentadienyl)hafniumdimethyl, (1,3-Diethylindenyl)(pentamethylcyclopentadienyl) hafniumdimethyl, (1,3- Dipropylindenyl)(pentamethylcyclopentadienyl)hafniumdimethyl, (1-Methyl, 3-propyllindenyl)(pentamethylcyclopentadienyl) hafniumdimethyl, (1,3- Dimethylindenyl)(tetramethylpropylcyclopentadienyl)hafniumdimethyl, (1,2,3-Trim ethylindenyl)(pentamethylcyclopentadienyl) hafniumdimethyl, (1,3- Dimethylbenzindenyl)(pentamethylcyclopentadienyl)hafniumdimethyl, (2,7-Bis t-butylfluorenyl)(pentamethylcyclopentadienyl)hafniumdimethyl, (9-Methylfluorenyl)(pentamethylcyclopentadienyl)hafniumdimethyl, (2,7,9-Trimethylfluorenyl)(pentamethylcyclopentadienyl)hafniumdimethyl, μ- Dihydrosilyl-bis(tetramethylcyclopentadienyl)hafniumdimethyl, μ-Dimethylsilyl(tetramethylcyclopentadienyl)(3-propyltrimethylcyclopentadienyl) hafniumdimethyl, μ-Dicyclopropylsilyl(bis tetramethylcyclopentadienyl)hafniumdimethyl, In an alternate embodiment, the "dimethyl" after the transition metal in the list of catalyst compounds above is replaced with a dihalide (such as dichloride, dibromide, or difluoride) or a bisphenoxide, particularly for use with an alumoxane activator.

Preferred activators useful with the above include: dimethylaniliniumtetrakis(pentafluorophenyl) borate, dimethylaniliniumtetrakis(heptafluoronaphthyl) borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl) ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis (perfluorobiphenyl) borate, tropillium tetrakis (perfluorobiphenyl) borate, triphenylcarbenium tetrakis (perfluorobiphenyl) borate, triphenylphosphonium tetrakis (perfluorobiphenyl) borate, triethylsilylium tetrakis (perfluorobiphenyl) borate, benzene(diazonium) tetrakis (perfluorobiphenyl) borate, and [4-t-butyl- $PhNMe_2H$][($C_6F_3$ $(C_6F_5)_2)_4B$] (where Ph is phenyl and Me is methyl).

In another embodiment, the vinyl terminated polyolefins useful here in may be produced using the catalyst compound represented by the formula:

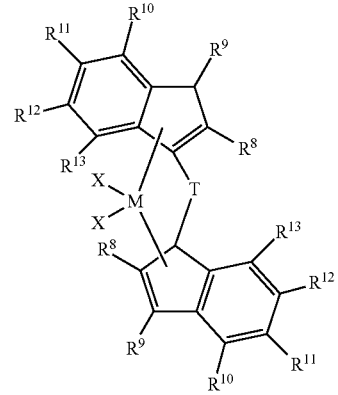

where M is hafnium or zirconium (preferably hafnium); each X is, independently, selected from the group consisting of hydrocarbyl radicals having from 1 to 20carbon atoms, hydrides, amides, alkoxides, sulfides, phosphides, halides, dienes, amines, phosphines, ethers, and a combination thereof, (two X's may form a part of a fused ring or a ring system) (preferably each X is independently selected from halides and $C_1$ to $C_5$ alkyl groups, preferably each X is a methyl group); each $R^8$ is, independently, a $C_1$ to $C_{10}$ alkyl group (preferably methyl, ethyl, propyl, butyl, pentyl, hexyl, or isomers thereof, preferably each $R^8$ is a methyl group); each $R^9$ is, independently, a $C_1$ to $C_{10}$ alkyl group (preferably methyl, ethyl, propyl, butyl, pentyl, hexyl, or isomers thereof, preferably each $R^9$ is a n-propyl group); each $R^{10}$ is hydrogen; each $R^{11}$, $R^{12}$ and $R^{13}$, is, independently, hydrogen or a substituted or unsubstituted hydrocarbyl group, a heteroatom or heteroatom containing group (preferably hydrogen); T is a bridging group (preferably T is dialkyl silicon or dialkyl germanium, preferably T is dimethyl silicon); and further provided that any of adjacent $R^{11}$, $R^{12}$, and $R^{13}$ groups may form a fused ring or multicenter fused ring system where the rings may be aromatic, partially saturated or saturated. For further information on such catalyst compounds and their use to make vinyl terminated macromers, please see concurrently filed U.S. Ser. No. 13/072,280, filed Mar. 25, 2011, entitled "Novel Catalysts and Methods of Use Thereof to Produce Vinyl Terminated Polymers".

Catalyst compounds that are particularly useful in this invention include one or more of: rac-dimethylsilyl bis(2-methyl,3-propylindenyl)hafniumdimethyl, rac-dimethylsilyl bis(2-methyl,3-propylindenyl)zirconiumdimethyl, rac-dimethylsilyl bis(2-ethyl,3-propylindenyl)hafniumdimethyl, rac-dimethylsilyl bis(2-ethyl,3-propylindenyl)zirconiumdimethyl, rac-dimethylsilyl bis(2-methyl,3-ethylindenyl)hafniumdimethyl, rac-dimethylsilyl bis(2-methyl,3-ethylindenyl)zirconiumdimethyl, rac-dimethylsilyl bis(2-methyl,3-isopropylindenyl)hafniumdimethyl, rac-dimethylsilyl bis(2-methyl,3-isopropylindenyl)zirconiumdimethyl, rac-dimethylsilyl bis(2-methyl,3-butyllindenyl)hafniumdimethyl, rac-dimethylsilyl bis(2-methyl,3-butylindenyl)zirconiumdimethyl, rac-dimethylgermanyl bis(2-methyl,3-propylindenyl)hafniumdimethyl, rac-dimethylgermanyl bis(2-methyl,3-propylindenyl)zirconiumdimethyl, rac-dimethylgermanyl bis(2-ethyl,3-propylindenyl)hafniumdimethyl, rac-dimethylgermanyl bis(2-ethyl,3-propylindenyl)zirconiumdimethyl, rac-dimethylgermanyl bis(2-methyl,3-ethylindenyl)hafniumdimethyl, rac-dimethylgermanyl bis(2-methyl,3-ethylindenyl)zirconiumdimethyl, rac-dimethylgermanyl bis(2-methyl,3-isopropylindenyl)hafniumdimethyl, rac-dimethylgermanyl bis(2-methyl,3-isopropylindenyl)zirconiumdimethyl, rac-dimethylgermanyl bis(2-methyl,3-butyllindenyl)hafniumdimethyl, rac-dimethylgermanyl bis(2-methyl,3-propylindenyl)zirconiumdimethyl, rac-dimethylsilyl bis(2-propyl,3-methylindenyl)hafniumdimethyl, rac-dimethylsilyl bis(2-propyl,3-methylindenyl)zirconiumdimethyl, rac-dimethylsilyl bis(2-propyl,3-ethylindenyl)hafniumdimethyl, rac-dimethylsilyl bis(2-propyl,3-ethylindenyl)zirconiumdimethyl, rac-dimethylsilylbis(2-propyl,3-butylindenyl)hafniumdimethyl, rac-dimethylsilylbis(2-propyl,3-butylindenyl)zirconiumdimethyl, rac-dimethylsilyl bis(2-methyl,3-butylindenyl)hafniumdimethyl, rac-dimethylsilyl bis(2-methyl,3-butylindenyl)zirconiumdimethyl, rac-dimethylsilyl bis(2,3-dimethyl)hafniumdimethyl, rac-dimethylsilyl bis(2,3-dimethyl)zirconiumdimethyl, rac-dimethylgermanyl bis(2-propyl,3-methylindenyl)hafniumdimethyl, rac-dimethylgermanyl bis(2-propyl,3-methylindenyl)zirconiumdimethyl, rac-dimethylgermanyl bis(2-propyl,3-ethylindenyl)hafniumdimethyl, rac-dimethylgermanyl bis(2-propyl,3-ethylindenyl)zirconiumdimethyl, rac-dimethylgermanyl bis(2-propyl,3-butylindenyl)hafniumdimethyl, rac-dimethylgermanyl bis(2-propyl,3-butylindenyl)zirconiumdimethyl, rac-dimethylgermanyl bis(2-methyl,3-butylindenyl)hafniumdimethyl, rac-dimethylgermanyl bis(2-methyl,3-butylindenyl)zirconiumdimethyl, rac-dimethylgermanyl bis(2,3-dimethyl)hafniumdimethyl and rac-dimethylgermanyl bis(2,3-dimethyl)zirconiumdimethyl.

In an alternate embodiment, the "dimethyl" after the transition metal in the list of catalyst compounds above is replaced with a dihalide (such as dichloride or difluoride) or a bisphenoxide, particularly for use with an alumoxane activator.

In particular embodiments, the catalyst compound is rac-dimethylsilylbis(2-methyl,3-propylindenyl)hafniumdimethyl or dichloride, or rac-dimethylsilylbis(2-methyl,3-propylindenyl)zirconiumdimethyl or dichloride.

Preferred activators useful with the above include: dimethylaniliniumtetrakis(pentafluorophenyl) borate, dimethylaniliniumtetrakis(heptafluoronaphthyl) borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis (perfluorobiphenyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium) tetrakis (perfluorobiphenyl)borate, and [4-t-butyl-PhNMe$_2$H][(C$_6$F$_3$(C$_6$F$_5$)$_2$)$_4$B] (where Ph is phenyl and Me is methyl).

Preferred combinations of catalyst and activator include: N,N-dimethylanilinium tetrakis(perfluorobiphenyl)borate and rac-dimethylsilylbis(2-methyl,3-propylindenyl)hafniumdimethyl, or rac-dimethylsilylbis(2-methyl,3-propylindenyl)zirconiumdimethyl.

In another embodiment, the vinyl terminated polyolefins useful here in may be produced using the catalyst compound represented by the formula:

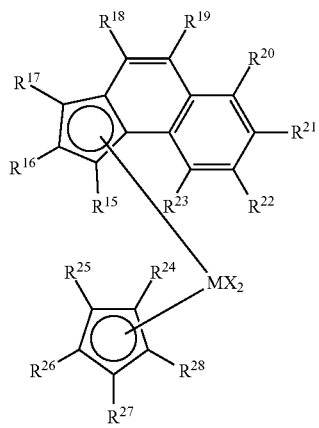

wherein M is hafnium or zirconium; each X is, independently, selected from the group consisting of hydrocarbyl radicals having from 1 to 20 carbon atoms, hydrides, amides, alkoxides, sulfides, phosphides, halogens, dienes, amines, phosphines, ethers, or a combination thereof; each $R^{15}$ and $R^{17}$ are, independently, a $C_1$ to $C_8$ alkyl group (preferably a $C_1$ to $C_8$ linear alkyl group, preferably methyl ethyl, propyl, butyl, pentyl, hexyl, heptyl or octyl); and each $R^{16}$, $R^{18}$, $R^{19}$, $R^{20}$ $R^{21}$, $R^{22}$, $R^{23}$, $R^{24}$, $R^{25}$, $R^{26}$, $R^{27}$, and $R^{28}$ are, independently, hydrogen, or a substituted or unsubstituted hydrocarbyl group having from 1 to 8 carbon atoms (preferably 1 to 6 carbon atoms, preferably a substituted or unsubstituted $C_1$ to $C_8$ linear alkyl group, preferably methyl ethyl, propyl, butyl, pentyl, hexyl, heptyl, octyl). In a preferred embodiment, at least three of $R^{24}$-$R^{28}$ groups are not hydrogen (alternately four of $R^{24}$-$R^{28}$ groups are not hydrogen, alternately five of $R^{24}$-$R^{28}$ groups are not hydrogen). In a preferred embodiment, all five groups of $R^{24}$-$R^{28}$ are methyl. In a preferred embodiment, four of the $R^{24}$-$R^{28}$ groups are not hydrogen and at least one of the $R^{24}$-$R^{28}$ groups is a $C_2$ to $C_8$ substituted or unsubstituted hydrocarbyl (preferably at least two, three, four or five of $R^{24}$-$R^{28}$ groups are a $C_2$ to $C_8$ substituted or unsubstituted hydrocarbyl). In another preferred embodiment, $R^{15}$ and $R^{17}$ are methyl groups, $R^{16}$ is a hydrogen, $R^{18}$-$R^{23}$ are all hydrogens, $R^{24}$-$R^{28}$ are all methyl groups, and each X is a methyl group. For further information on such catalyst compounds and their use to make vinyl terminated macromers, please see concurrently filed U.S. Ser. No. 13/072,279, filed Mar. 25, 2011, entitled "Enhanced Catalyst Performance for Production of Vinyl Terminated Propylene and Ethylene/Propylene Macromers."

Catalyst compounds that are particularly useful in this invention include: (CpMe$_5$)(1,3-Me$_2$-benz[e]indenyl)HfMe$_2$, (CpMe$_5$)(1-methyl-3-n-propylbenz[e]indenyl)HfMe$_2$, (CpMe$_5$)(1-n-propyl,3-methylbenz[e]indenyl)HfMe$_2$, (CpMe$_5$)(1-methyl-3-n-butylbenz[e]indenyl)HfMe$_2$, (CpMe$_5$)(1-n-butyl,3-methylbenz[e]indenyl)HfMe$_2$, (CpMe$_5$)(1-ethyl,3-methylbenz[e]indenyl)HfMe$_2$, (CpMe$_5$)(1-methyl, 3-ethylbenz[e]indenyl)HfMe$_2$, (CpMe$_4$n-propyl)(1,3-Me$_2$-benz[e]indenyl)HfMe$_2$, (CpMe$_4$-n-propyl)(1-methyl-3-n-propylbenz[e]indenyl)HfMe$_2$, (CpMe$_4$-n-propyl)(1-n-propyl,3-methylbenz[e]indenyl)HfMe$_2$, (CpMe$_4$-n-propyl)(1-methyl-3-n-butylbenz[e]indenyl)HfMe$_2$, (CpMe$_4$-n-propyl)(1-n-butyl,3-methylbenz[e]indenyl)HfMe$_2$, (CpMe$_4$-n-propyl)(1-ethyl,3-methylbenz[e]indenyl)HfMe$_2$, (CpMe$_4$-n-propyl)(1-methyl, 3-ethylbenz[e]indenyl)HfMe$_2$, (CpMe$_4$n-butyl)(1,3-Me$_2$-benz[e]indenyl)HfMe$_2$, (CpMe$_4$n-butyl)(1-methyl-3-n-propylbenz[e]indenyl)HfMe$_2$, (CpMe$_4$n-butyl)(1-n-propyl,3-methylbenz[e]indenyl)HfMe$_2$, (CpMe$_4$n-butyl)(1-methyl-3-n-butylbenz[e]indenyl)HfMe$_2$, (CpMe$_4$n-butyl)(1-n-butyl,3-methylbenz[e]indenyl)HfMe$_2$, (CpMe$_4$n-butyl)(1-ethyl,3-methylbenz[e]indenyl)HfMe$_2$, (CpMe$_4$n-butyl)(1-methyl, 3-ethylbenz[e]indenyl)HfMe$_2$, and the zirconium analogs thereof.

In an alternate embodiment, the "dimethyl" (Me$_2$) after the transition metal in the list of catalyst compounds above is replaced with a dihalide (such as dichloride or difluoride) or a bisphenoxide, particularly for use with an alumoxane activator.

Other activators useful with the above catalysts include: dimethylaniliniumtetrakis(pentafluorophenyl) borate, dimethylaniliniumtetrakis(heptafluoronaphthyl) borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, and [4-t-butyl-PhNMe$_2$H][(C$_6$F$_3$(C$_6$F$_5$)$_2$)$_4$B].

In a preferred embodiment, the branched polymers described herein may be produced as described in concurrently filed U.S. Ser. No. 61/467,681, filed Mar. 25, 2011, entitled "Branched Vinyl Terminated Polymers and Methods for Production Thereof".

With regard to the above catalyst compounds, the term "substituted" means that a hydrogen group has been replaced with a hydrocarbyl group, a heteroatom or a heteroatom containing group. For example methyl cyclopentadiene (Cp) is a Cp group substituted with a methyl group and ethyl alcohol is an ethyl group substituted with an —OH group.

Activators and Activation Methods for Catalyst Compounds to Make Vinyl Terminated Polymers The terms "cocatalyst" and "activator" are used herein interchangeably and are defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract one reactive, σ-bound, metal ligand making the metal complex cationic and providing a charge-balancing noncoordinating or weakly coordinating anion.

In one embodiment, alumoxane activators are utilized as an activator in the catalyst composition. Alumoxanes are generally polymeric compounds containing —Al(R$^1$)—O— subunits, where R$^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. Another alumoxane is a modified methyl alumoxane (MMAO) cocatalyst type 3A (commercially available from Akzo Chemicals, Inc. under the trade name Modified Methylalumoxane type 3A, covered under U.S. Pat. No. 5,041,584).

When the activator is an alumoxane (modified or unmodified), some embodiments select the maximum amount of activator at a 5000-fold molar excess Al/M over the catalyst precursor (per metal catalytic site). The minimum activator-to-catalyst-precursor is a 1:1 molar ratio. Alternate preferred ranges include up to 500:1, alternately up to 200:1, alternately up to 100:1 alternately from 1:1 to 50:1.

In a preferred embodiment, little or no alumoxane is used in the process to produce the vinyl terminated polyolefin. Preferably, alumoxane is present at zero mol %, alternately the alumoxane is present at a molar ratio of aluminum to transition metal less than 500:1, preferably less than 300:1, preferably less than 100:1, preferably less than 1:1.

In an alternate embodiment, if an alumoxane is used to produce the VTM's then, the alumoxane has been treated to remove free alkyl aluminum compounds, particularly trimethyl aluminum.

Further, in a preferred embodiment, the activator used herein to produce the vinyl terminated polyolefin is bulky as defined herein and is discrete.

Aluminum alkyl or organoaluminum compounds which may be utilized as co-activators (or scavengers) include trimethylaluminum, triethylaluminum, triisobutylaluminum, tri-n-hexylaluminum, tri-n-octylaluminum and the like.

Ionizing Activators

It is within the scope of this invention to use an ionizing or stoichiometric activator, neutral or ionic non-coordinating anion (as defined in U.S. Ser. No. 12/143,663, filed on Jun. 20, 2008) such as tri (n-butyl) ammonium tetrakis (pentafluorophenyl) borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators. Preferably the activator is N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetrakis (perfluorophenyl)borate. For additional activators useful herein, please see U.S. Ser. No. 12/143,663, filed on Jun. 20, 2008.

In another embodiment, the activator is a bulky activator represented by the formula:

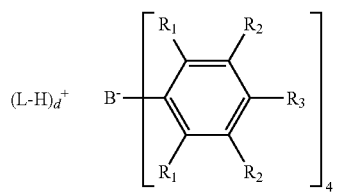

where:
each $R_1$ is, independently, a halide, preferably a fluoride;
each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_2$ is a fluoride or a perfluorinated phenyl group);
each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring);
L is an neutral Lewis base; $(L-H)^+$ is a Bronsted acid; d is 1, 2, or 3;
wherein the anion has a molecular weight of greater than 1020 g/mole; and
wherein at least three of the substituents on the B atom each have a molecular volume of greater than 250 cubic Å, alternately greater than 300 cubic Å, or alternately greater than 500 cubic Å.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple "Back of the Envelope" Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: $MV=8.3V_s$, where $V_s$ is the scaled volume. $V_s$ is the sum of the relative volumes of the constituent atoms, and is calculated from the molecular formula of the substituent using the following table of relative volumes. For fused rings, the $V_s$ is decreased by 7.5% per fused ring.

| Element | Relative Volume |
| --- | --- |
| H | 1 |
| 1st short period, Li to F | 2 |
| 2nd short period, Na to Cl | 4 |
| 1st long period, K to Br | 5 |
| 2nd long period, Rb to I | 7.5 |
| 3rd long period, Cs to Bi | 9 |

Exemplary bulky substituents of activators suitable herein and their respective scaled volumes and molecular volumes are shown in the table below. The dashed bonds indicate binding to boron, as in the general formula above.

| Activator | Structure of boron substituents | Molecular Formula of each substituent | $V_S$ | MV Per subst. (Å³) | Total MV (Å³) |
| --- | --- | --- | --- | --- | --- |
| Dimethylanilinium tetrakis(perfluoronaphthyl)borate | | $C_{10}F_7$ | 34 | 261 | 1044 |
| Dimethylanilinium tetrakis(perfluorobiphenyl)borate | | $C_{12}F_9$ | 42 | 349 | 1396 |

| Activator | Structure of boron substituents | Molecular Formula of each substituent | $V_S$ | MV Per subst. (Å³) | Total MV (Å³) |
|---|---|---|---|---|---|
| [4-t-butyl-PhNMe₂H][(C₆F₃(C₆F₅)₂)₄B] | 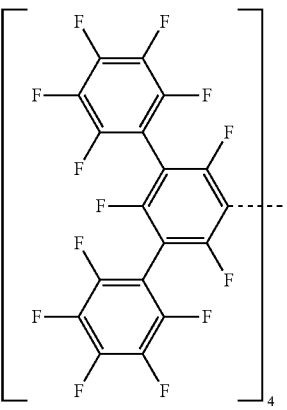 | $C_{18}F_{13}$ | 62 | 515 | 2060 |

Exemplary bulky activators useful in catalyst systems herein include: trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, [4-t-butyl-PhNMe₂H] [(C₆F₃(C₆F₅)₂)₄B], and the types disclosed in U.S. Pat. No. 7,297,653.

The typical activator-to-catalyst-precursor ratio is a 1:1 molar ratio for non-alumoxane activators. Alternate preferred ranges include from 0.1:1 to 100:1, alternately from 0.5:1 to 200:1, alternately from 1:1 to 500:1 alternately from 1:1 to 1000:1. A particularly useful range is from 0.5:1 to 10:1, preferably 1:1 to 5:1.

Support Materials

In embodiments herein, the catalyst system to make the vinyl terminated polyolefins may comprise an inert support material. Preferably the supported material is a porous support material, for example, talc, and inorganic oxides. Other support materials include zeolites, clays, organoclays, or any other organic or inorganic support material and the like, or mixtures thereof.

Preferably, the support material is an inorganic oxide in a finely divided form. Suitable inorganic oxide materials for use in metallocene catalyst systems herein include Groups 2, 4, 13, and 14 metal oxides such as silica, alumina and mixtures thereof. Other inorganic oxides that may be employed either alone or in combination with the silica, or alumina are magnesia, titania, zirconia, and the like. Other suitable support materials, however, can be employed, for example, finely divided functionalized polyolefins such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania and the like. Preferred support materials include $Al_2O_3$, $ZrO_2$, $SiO_2$, and combinations thereof, more preferably $SiO_2$, $Al_2O_3$, or $SiO_2/Al_2O_3$.

It is preferred that the support material, most preferably an inorganic oxide, has a surface area in the range of from about 10 to about 700 m²/g, pore volume in the range of from about 0.1 to about 4.0 cc/g and average particle size in the range of from about 5 to about 500 µm. More preferably, the surface area of the support material is in the range of from about 50 to about 500 m²/g, pore volume of from about 0.5 to about 3.5 cc/g and average particle size of from about 10 to about 200 µm. Most preferably the surface area of the support material is in the range is from about 100 to about 400 m²/g, pore volume from about 0.8 to about 3.0 cc/g and average particle size is from about 5 to about 100 µm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 m²/gm; pore volume of 1.65 cm³/gm), examples of which are marketed under the tradenames of DAVISON 952 or DAVISON 955 by the Davison Chemical Division of W.R. Grace and Company. In other embodiments, DAVISON 948 is used.

The support material should be dry, that is, free of absorbed water. Drying of the support material can be effected by heating or calcining at about 100° C. to about 1000° C., preferably at least about 600° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours. The calcined support material must have at least some reactive hydroxyl (OH) groups to produce the catalyst system of this invention. The calcined support material is then contacted with at least one polymerization catalyst comprising at least one metallocene compound and an activator.

Methods of Making the Supported Catalyst Systems

The support material, having reactive surface groups, typically hydroxyl groups, is slurried in a non-polar solvent and the resulting slurry is contacted with a solution of a metallocene compound and an activator. The slurry of the support material in the solvent is prepared by introducing the support material into the solvent, and heating the mixture to about 0° to about 70° C., preferably to about 25° to about 60° C., preferably at room temperature. Contact times typically range from about 0.5 hours to about 24 hours, from about 0.5 hours to about 8 hours, or from about 0.5 hours to about 4 hours.

Suitable non-polar solvents are materials in which all of the reactants used herein, i.e., the activator, and the metallocene compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene and ethylbenzene, may also be employed.

In embodiments herein, the support material is contacted with a solution of a metallocene compound and an activator, such that the reactive groups on the support material are titrated, to form a supported polymerization catalyst. The period of time for contact between the metallocene compound, the activator, and the support material is as long as is necessary to titrate the reactive groups on the support material. To "titrate" is meant to react with available reactive groups on the surface of the support material, thereby reducing the surface hydroxyl groups by at least 80%, at least 90%, at least 95%, or at least 98%. The surface reactive group concentration may be determined based on the calcining temperature and the type of support material used. The support material calcining temperature affects the number of surface reactive groups on the support material available to react with the metallocene compound and an activator: the higher the drying temperature, the lower the number of sites. For example, where the support material is silica which, prior to the use thereof in the first catalyst system synthesis step, is dehydrated by fluidizing it with nitrogen and heating at about 600° C. for about 16 hours, a surface hydroxyl group concentration of about 0.7 millimoles per gram (mmols/gm) is typically achieved. Thus, the exact molar ratio of the activator to the surface reactive groups on the carrier will vary. Preferably, this is determined on a case-by-case basis to assure that only so much of the activator is added to the solution as will be deposited onto the support material without leaving excess of the activator in the solution.

The amount of the activator which will be deposited onto the support material without leaving excess in the solution can be determined in any conventional manner, e.g., by adding the activator to the slurry of the carrier in the solvent, while stirring the slurry, until the activator is detected as a solution in the solvent by any technique known in the art, such as by $^1$H NMR. For example, for the silica support material heated at about 600° C., the amount of the activator added to the slurry is such that the molar ratio of B to the hydroxyl groups (OH) on the silica is about 0.5:1 to about 4:1, preferably about 0.8:1 to about 3:1, more preferably about 0.9:1 to about 2:1 and most preferably about 1:1. The amount of boron on the silica may be determined by using ICPES (Inductively Coupled Plasma Emission Spectrometry), which is described in J. W. Olesik, "Inductively Coupled Plasma-Optical Emission Spectroscopy," in the Encyclopedia of Materials Characterization, C. R. Brundle, C. A. Evans, Jr. and S. Wilson, eds., Butterworth-Heinemann, Boston, Mass., 1992, pp. 633-644. In another embodiment, it is also possible to add such an amount of activator which is in excess of that which will be deposited onto the support, and then remove, e.g., by filtration and washing, any excess of the activator.

In another embodiment, a vinyl terminated polyolefin can be produced by the method disclosed in Macromol. Chem. Phys. 2010, 211, pp. 1472-1481.

Hydrosilane Functionalized Polyolefins

Preferred hydrosilane-functionalized polyolefins prepared herein are preferably represented by the formula: PO—Si(R*)$_m$H$_n$, PO—Si(R*)$_2$H, or PO—Si(R*)2-L-Si(R**)$_2$H, wherein m is 1 or 2; n is 1 or 2; m+n=3; PO is substituted or unsubstituted hydrocarbyl group having from 20 to about 10,000 carbon atoms (optionally PO is any of the vinyl terminated polyolefins described herein above or below except that the allyl chain ends are absent); each R*, independently, is a H, or a $C_1$ to a $C_{20}$ substituted or unsubstituted hydrocarbyl group (preferably H or methyl, ethyl, propyl, butyl, pentyl, hexyl, heptyl, octyl, nonyl, decyl undecyl, dodecyl, phenyl, substituted phenyl (such as methyl phenyl, di methyl phenyl), preferably hydrogen, methyl or phenyl), where any two R* may form a cyclic structure with Si; L is a bond or a linking group (preferably L is an oxygen, a substituted or unsubstituted hydrocarbyl group, or a substituted or unsubstituted hydrocarbyl containing ether group, preferably L is a substituted or unsubstituted $C_1$ to a $C_{12}$ hydrocarbyl group, such as methyl, ethyl, propyl, butyl, pentyl, hexyl, heptyl, octyl, nonyl, decyl undecyl, dodecyl, phenyl, substituted phenyl (such as methyl phenyl, di methyl phenyl); and each R, independently, is a H, or a $C_1$ to a $C_{20}$ substituted or unsubstituted hydrocarbyl group (preferably H or methyl, ethyl, propyl, butyl, pentyl, hexyl, heptyl, octyl, nonyl, decyl undecyl, dodecyl, phenyl, substituted phenyl (such as methyl phenyl, di methyl phenyl), preferably hydrogen, methyl or phenyl), where any two R may form a cyclic structure with Si.

In a preferred embodiment, L is a $C_1$ to $C_{12}$ substituted or unsubstituted hydrocarbyl containing ether group, preferably a $C_2$ to $C_{12}$ substituted or unsubstituted hydrocarbyl containing ether group, preferably L is —CH$_2$OCH$_2$—, —CH$_2$CH$_2$—O—CH$_2$CH$_2$—, —CH$_2$CH$_2$CH$_2$—O—CH$_2$CH$_2$CH$_2$—, or —C$_6$H$_4$—O—C$_6$H$_4$—.

In a preferred embodiment, the PO in the formulae above is a hydrocarbyl or substituted hydrocarbyl having 100 to 10,000 carbon atoms, preferably 500 to 10,000, preferably 1000 to 10,000, preferably 5000 to 10,000 carbon atoms, preferably PO is substituted or unsubstituted eicosene, polyethylene or polypropylene.

In a preferred embodiment, the hydrosilane-functionalized polyolefin has a Mn of from 500 to 50,000 g/mol, preferably from 1000 to 30,000 g/mol, preferably from 1500 to 10,000 g/mol. In a preferred embodiment the "polyolefin" portion of the hydrosilane-functionalized polyolefin is a homopolymer, homo-oligomer, copolymer or co-oligomer comprising one or more $C_2$ to $C_{40}$ olefins, preferably $C_2$ to $C_{40}$ alpha-olefins, preferably ethylene, propylene, butene, pentene, hexene, octene, nonene, decene, undecene, and dodecene.

In a preferred embodiment, the hydrosilane-functionalized polyolefin is an oligomer having an Mn of from 500 to 21,000 g/mol (preferably 700 to 21,000, preferably 800 to 20,000 g/mol) comprising one or more alpha-olefins selected from the group consisting of $C_2$ to $C_{40}$ alpha-olefins, preferably ethylene, propylene, butene, pentene, hexene, octene, nonene, decene, undecene and dodecene. Preferably the oligomer portion of the hydrosilane-functionalized polyolefin is an ethylene oligomer, e.g., a homo-oligomer of ethylene or co-oligomer of ethylene and up to 50 mol % (preferably from 0.5 to 25 mol %, preferably from 1 to 20 mol %) of one or more $C_2$ to $C_{40}$ alpha-olefin comonomers, preferably selected from the group consisting of propylene, butene, pentene, hexene, octene, nonene, decene, undecene and dodecene. Alternately, the oligomer portion of the hydrosilane-functionalized polyolefin is a propylene oligomer, e.g., a homo-oligomer of propylene or co-oligomer of propylene and up to 50 mol % (preferably from 0.5 to 25 mol %, preferably from 1 to 20 mol %) of one or more $C_2$ to $C_{40}$ alpha-olefin comonomers, preferably selected from the group consisting of ethylene, butene, pentene, hexene, octene, nonene, decene, undecene and dodecene.

In a preferred embodiment, the hydrosilane-functionalized polyolefin is a polymer having an Mn of greater than 21,000 g/mol (preferably from 25,000 to 100,000, preferably 25,000 to 50,000 g/mol) comprising one or more alpha-olefins selected from the group consisting of $C_2$ to $C_{40}$ alpha-olefins, preferably ethylene, propylene, butene, pentene, hexene, octene, nonene, decene, undecene and dodecene. Preferably the polymer portion of the hydrosilane-functionalized polyolefin is an ethylene polymer, e.g., a homopolymer of ethylene or co-polymer of ethylene and up to 50 mol % (preferably from 0.5 to 25 mol %, preferably from 1 to 20 mol %) of one or more $C_3$ to $C_{40}$ alpha-olefin comonomers, preferably selected from the group consisting of propylene, butene, pentene, hexene, octene, nonene, decene, undecene and dodecene. Alternately, the polymer portion of the hydrosilane-functionalized polyolefin is propylene polymer, e.g., a homopolymer of propylene or a co-polymer of propylene and up to 50 mol % (preferably from 0.5 to 25 mol %, preferably from 1 to 20 mol %) of one or more $C_2$ to $C_{40}$ alpha-olefins comonomers, preferably selected from the group consisting of ethylene, butene, pentene, hexene, octene, nonene, decene, undecene and dodecene.

In another embodiment, the hydrosilane-functionalized polyolefins consist essentially of propylene, functional group and optionally ethylene. Alternately $C_4$ olefins (such as isobutylene, butadiene, n-butene) are substantially absent from the hydrosilane-functionalized polyolefins. Alternately $C_{4-20}$ olefins are substantially absent from the hydrosilane-functionalized polyolefins. Alternately isobutylene is substantially absent from the hydrosilane-functionalized polyolefins. By substantially absent is meant that the monomer is present in the polyolefin at 1 wt % or less, preferably at 0.5 wt % or less, preferably at 0 wt %.

In a preferred embodiment, the hydrosilane-functionalized polyolefins produced herein have a melting point (DSC, second melt) of 100° C. or more, preferably 120° C. or more, preferably 130° C. or more. In another preferred embodiment, the hydrosilane-functionalized polyolefin produced herein is an hydrosilane-functionalized propylene polymer having a melting point (DSC, second melt) of 145° C. or more, preferably 150° C. or more, preferably 155° C. or more. In another preferred embodiment, the hydrosilane-functionalized polyolefin produced herein is an hydrosilane-functionalized ethylene polymer having a melting point (DSC, second melt) of 100° C. or more, preferably 110° C. or more, preferably 125° C. or more.

The hydrosilane-functionalized polyolefins may be characterized by any degree of tacticity, including isotacticity or syndiotacticity, and/or may be atactic. In an embodiment the hydrosilane-functionalized polyolefin has more than 50% meso dyads as measured by $^{13}C$ NMR, preferably more than 60%. In an alternate embodiment the hydro-silane functionalized polyolefin has more than 50% racemic dyads as measured by $^{13}C$ NMR, preferably more than 60%.

Particularly useful hydrosilane-functionalized polyolefins may be isotactic, highly isotactic, syndiotactic, or highly syndiotactic propylene polymer, particularly isotactic polypropylene. As used herein, "isotactic" is defined as having at least 10% isotactic pentads, preferably having at least 40% isotactic pentads of methyl groups derived from propylene according to analysis by $^{13}C$ NMR. As used herein, "highly isotactic" is defined as having at least 60% isotactic pentads according to analysis by $^{13}C$ NMR. In a desirable embodiment, the hydrosilane-functionalized polyolefin (preferably polypropylene) has at least 85% isotacticity. As used herein, "syndiotactic" is defined as having at least 10% syndiotactic pentads, preferably at least 40%, according to analysis by $^{13}C$ NMR. As used herein, "highly syndiotactic" is defined as having at least 60% syndiotactic pentads according to analysis by $^{13}C$ NMR. In another embodiment, the hydrosilane functionalized polyolefin (preferably polypropylene) has at least 85% syndiotacticity.

In a preferred embodiment, the hydrosilane-functionalized polyolefins described herein have less than 10% allyl chain ends, preferably less than 8%, preferably less than 6%, preferably less than 5%, preferably less than 4%, preferably less than 3%, preferably less than 2%, preferably less than 1% (relative to total unsaturations as measured by $^1H$ NMR, using the protocol described in U.S. Ser. No. 12/143,663, filed on Jun. 20, 2008). No hydrogen or chain transfer/termination agent should be used during functionalization, derivatization or stripping (of unreacted monomer) for measurement of unsaturations.

In another embodiment, the number of functional groups (i.e., hydrosilane groups) is present at 0.60 to 1.2, alternately 0.75 to 1.1 functional groups per chain (preferably assuming that Mn has not altered by more than 15% as compared to the Mn of the polyolefin prior to functionalization and optional derivatization). Number of functional groups per chain=F/Mn as determined by $^1H$ NMR as follows: The instrument used is a 400 MHz Varian pulsed Fourier transform NMR spectrometer equipped with a variable temperature proton detection probe operating at 120° C. The sample is dissolved in 1,1,2,2-tetrachloroethane-$d_2$ (TCE-$d_2$) or $CDCl_3$ and transferred into a 5 mm glass NMR tube. (The solvent has less than 10,000 ppm water and is free of other contaminants that could change the chemical shifts in the NMR spectrum). Acquisition parameters are pulse width=45°, acquisition delay=8 s and number of scans=120. Chemical shifts are determined relative to the residual TCE-$d_1$ signal which is set to 5.98 ppm and residual $CHCl_3$. which is set at 7.24 ppm. VRA is the normalized integrated signal intensity for the vinyls with shifts between from about 4.9 to 5.1 ppm. VDRA is the normalized integrated signal intensity for the vinylidene resonances between from about 4.65 to 4.85 ppm and the vinylene resonances at from about 5.15 to 5.6 ppm. IA is the normalized integrated signal intensities for the aliphatic region of interest between from about 0 to 2.1 ppm (IA). The number of vinyl groups/1000 Carbons (VI) is determined from the formula: (VRA*1000)/(IA+VRA+VDRA). Likewise, the number of vinylidene & vinylene groups/1000 carbons (VE) is determined from the formula: (VDRA*1000)/(IA+VRA+VDRA). VRA, VDRA and IA are the normalized integrated signal intensities in the chemical shift regions defined above. Mn is calculated assuming one unsaturated end-group per polyolefin chain. Mn=(14,000 g/mol)/(VI+VE).

After the polyolefin in question is functionalized it is necessary to determine the resonances/chemical shift regions of the functional group to determine % functionalization. To do so, repeat the above $^1$H NMR procedure on a clean sample of the functionalized polyolefin (e.g., washed to remove unreacted materials, contaminants, etc.). Refer to "The Sadtler Guide to NMR Spectra", ed. William Walter Simons, published by the Sadtler Research Laboratories, 1972 for assistance in determining the shift regions for specific functional groups. The number of functional groups/1000 C's (F)= (FA*1000)/(FA+IA+VRA+VDRA), where FA=normalized integrated signal intensities in the chemical shift region of the functional group, and IA, VRA, VDRA are as defined above.

Percent functionalization of the polyolefin=(F*100)/(F+VI+VE). The number of vinyl groups/1000 carbons (VI*) and number of vinylidene groups/1000 carbons (VE*) for the functionalized polyolefin are determined from the $^1$HNMR spectra of the functionalized oligomer in the same manner as VI and VE for the unfunctionalized polyolefin. Preferably the percent functionalization of the polyolefin is 75% or more, preferably 80% or more, preferably 90% or more, preferably 95% or more.

In a preferred embodiment, $F+VI^*+VE^* \geqq (0.50(VI+VE))$, preferably $F+VI^*+VE^* \geqq (0.60(VI+VE))$, preferably $F+VI^*+VE^* \geqq (0.70(VI+VE))$, preferably $F+VI^*+VE^* \geqq (0.75(VI+VE))$, preferably $F+VI^*+VE^* \geqq (0.80(VI+VE))$, preferably $F+VI^*+VE^* \geqq (0.85(VI+VE))$, preferably $F+VI^*+VE^* \geqq (0.90(VI+VE))$, preferably $F+VI^*+VE^* \geqq (0.95(VI+VE))$, preferably $F+VI^*+VE^* \geqq (0.98(VI+VE))$, preferably $F+VI^*+VE^* \geqq (0.99(VI+VE))$.

Preferred functional groups include acyl groups derived from monounsaturated mono- or dicarboxylic acids and their derivatives, e.g., esters and salts.

In another embodiment, the hydrosilane-functionalized polyolefin produced herein has a branching index, $g'_{vis}$ (as determined by GPC), of 0.98 or less, alternately 0.96 or less, alternately 0.95 or less, alternately 0.93 or less, alternately 0.90 or less, alternately 0.85 or less, alternately 0.80 or less, alternately 0.75 or less, alternately 0.70 or less, alternately 0.65 or less, alternately 0.60 or less, alternately 0.55 or less.

Derivatization and Further Reactions

The functionalized vinyl terminated polyolefins described herein may be further derivatized as described in U.S. Pat. No. 6,022,929. The Si—H bond can be converted to a halides; PO—Si—X by reaction with $AlX_3$ or organic $RX_4$ (PO is a polyolefin and X is a halogen, such as Cl). The PO—Si—H could be transformed into a radical [PO—Si] by a variety of reactants (see Organosilanes in Radical Chemistry, Wiley, 2004) and further derivatized into silyl-halides, siloxanes, or silazanes. The PO-silanes or derivatized versions themselves may be polymerized to polysilanes; —Si(PO)—Si(PO)—Si(PO)— (See Silicon Chemistry: From the Atom to Extended Systems, Wiley-VCH, 2007). Less substituted PO—SiH$_2$— themselves may act as hydrosilation reagents with unsaturated molecules such as alkynes, ketones, alkenes, etc with suitable hydrosilation catalysts as $H_2PtCl_6$. The PO—SiH molecules can be oxidized to PO—SiOH or PO—SiOR, R=alkyl, aryl, etc with suitable reagents.

Blends of Hydrosilane-Functionalized Polyolefins

In some embodiments, the hydrosilane-functionalized (and optionally derivatized) polyolefins produced by this invention may be blended with up to 99 wt % (typically 80-98%, and ideally about 2 to about 5 wt %) of one or more other polymers, including but not limited to, thermoplastic polymer(s) and/or elastomer(s).

By thermoplastic polymer(s) is meant a polymer that can be melted by heat and then cooled without appreciable change in properties. Thermoplastic polymers typically include, but are not limited to, polyolefins, polyamides, polyesters, polycarbonates, polysulfones, polyacetals, polylactones, acrylonitrile-butadiene-styrene resins, polyphenylene oxide, polyphenylene sulfide, styrene-acrylonitrile resins, styrene maleic anhydride, polyimides, aromatic polyketones, or mixtures of two or more of the above. Preferred polyolefins include, but are not limited to, polymers comprising one or more linear, branched or cyclic $C_2$ to $C_{40}$ olefins, preferably polymers comprising propylene copolymerized with one or more $C_3$ to $C_{40}$ olefins, preferably a $C_3$ to $C_{20}$ alpha-olefin, more preferably $C_3$ to $C_{10}$ alpha-olefins. More preferred polyolefins include, but are not limited to, polymers comprising ethylene including but not limited to ethylene copolymerized with a $C_3$ to $C_{40}$ olefin, preferably a $C_3$ to $C_{20}$ alpha-olefin, more preferably propylene and/or butene.

By elastomers is meant all natural and synthetic rubbers, including those defined in ASTM D1566. Examples of preferred elastomers include, but are not limited to, ethylene propylene rubber, ethylene propylene diene monomer rubber, styrenic block copolymer rubbers (including SI, SIS, SB, SBS, SIBS, and the like, where S=styrene, I=isobutylene, and B=butadiene), butyl rubber, halobutyl rubber, copolymers of isobutylene and para-alkylstyrene, halogenated copolymers of isobutylene and para-alkylstyrene, natural rubber, polyisoprene, copolymers of butadiene with acrylonitrile, polychloroprene, alkyl acrylate rubber, chlorinated isoprene rubber, acrylonitrile chlorinated isoprene rubber, polybutadiene rubber (both cis and trans).

In another embodiment, the hydrosilane-functionalized (and optionally derivatized) polyolefins produced herein may further be combined with one or more of polybutene, ethylene vinyl acetate, low density polyethylene (density 0.915 to less than 0.935 g/cm$^3$) linear low density polyethylene, ultra low density polyethylene (density 0.86 to less than 0.90 g/cm$^3$), very low density polyethylene (density 0.90 to less than 0.915 g/cm$^3$), medium density polyethylene (density 0.935 to less than 0.945 g/cm$^3$), high density polyethylene (density 0.945 to 0.98 g/cm$^3$), ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, crosslinked polyethylene, copolymers of ethylene and vinyl alcohol (EVOH), polymers of aromatic monomers such as polystyrene, poly-1 esters, polyacetal, polyvinylidine fluoride, polyethylene glycols and/or polyisobutylene. Preferred polymers include those available from ExxonMobil Chemical Company in Baytown, Tex. under the tradenames EXCEED™ and EXACTT™.

Tackifiers may be blended with the hydrosilane-functionalized (and optionally derivatized) polyolefins produced herein and/or with blends of the hydrosilane-functionalized (and optionally derivatized) polyolefins produced by this inventions (as described above). Examples of useful tackifiers include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, and hydrogenated rosin esters. In some embodiments the tackifier is hydrogenated. In some embodiments the tackifier has a softening point (Ring and Ball, as measured by ASTM E-28) of 80° C. to 140° C., preferably 100° C. to 130° C. The tackifier, if present, is typically present at about 1 wt % to about 50 wt %, based upon the weight of the blend, more preferably 10 wt % to 40 wt %, even more preferably 20 wt % to 40 wt %.

In another embodiment the hydrosilane-functionalized (and optionally derivatized) polyolefins of this invention, and/or blends thereof, further comprise typical additives known in the art such as fillers, cavitating agents, antioxidants, surfactants, adjuvants, plasticizers, block, antiblock, color masterbatches, pigments, dyes, processing aids, UV stabilizers, neutralizers, lubricants, waxes, and/or nucleating agents. The additives may be present in the typically effective amounts well known in the art, such as 0.001 wt % to 10 wt %. Preferred fillers, cavitating agents and/or nucleating agents include titanium dioxide, calcium carbonate, barium sulfate, silica, silicon dioxide, carbon black, sand, glass beads, mineral aggregates, talc, clay and the like. Preferred antioxidants include phenolic antioxidants, such as Irganox 1010, Irganox, 1076 both available from Ciba-Geigy. Preferred oils include paraffinic or naphthenic oils such as Primol 352, or Primol 876 available from ExxonMobil Chemical France, S. A. in Paris, France. More preferred oils include aliphatic naphthenic oils, white oils or the like.

In a particularly preferred embodiment, the hydrosilane-functionalized (and optionally derivatized) polyolefins produced herein are combined with polymers (elastomeric and/or thermoplastic) having functional groups such as unsaturated molecules-vinyl bonds, ketones or aldehydes under conditions such that they react. Reaction may be confirmed by an at least 20% (preferably at least 50%, preferably at least 100%) increase in Mw as compared to the Mw of the hydrosilane-functionalized polyolefin prior to reaction. Such reaction conditions may be increased heat (for example, above the Tm of the hydrosilane-functionalized polyolefin), increased shear (such as from a reactive extruder), presence or absence of solvent. Conditions useful for reaction include temperatures from 150° C. to 240° C. and where the PO—Si—H species can be added to a stream comprising polymer and other species via a side arm extruder, gravimetric feeder, or liquids pump. Useful polymers having functional groups that can be reacted with the hydrosilane-functionalized polyolefins produced herein include polyesters, polyvinyl acetates, nylons (polyamides), polybutadiene, nitrile rubber, hydroxylated nitrile rubber.

In some embodiments, the hydrosilane-functionalized (and optionally derivatized) polyolefin of this invention may be blended with up to 99 wt % (preferably up to 25 wt %, preferably up to 20 wt %, preferably up to 15 wt %, preferably up to 10 wt %, preferably up to 5 wt %), based upon the weight of the composition, of one or more additional polymers.

Suitable polymers include:

PM1) Polyethylenes, including (but not limited to):
Copolymers of ethylene and one or more polar monomers, preferably selected from vinyl acetate, methyl acrylate, n-butyl acrylate, acrylic acid, and vinyl alcohol (i.e., EVA, EMA, EnBA, EAA, and EVOH); ethylene homopolymers and copolymers synthesized using a high-pressure free radical process, including LDPE; copolymers of ethylene and $C_3$ to $C_{40}$ olefins (preferably propylene and/or butene) with a density of greater than 0.91 g/cm$^3$ to less than 0.94 g/cm$^3$), including LLDPE; and high density PE (0.94 to 0.98 g/cm$^3$).

PM2) Polybutene-1 and copolymers of polybutene-1 with ethylene and/or propylene.

PM3) Non-EP Rubber Elastomers, including (but not limited to):
Polyisobutylene, butyl rubber, halobutyl rubber, copolymers of isobutylene and para-alkylstyrene, halogenated copolymers of isobutylene and para-alkylstyrene, natural rubber, polyisoprene, copolymers of butadiene with acrylonitrile, polychloroprene, alkyl acrylate rubber, chlorinated isoprene rubber, acrylonitrile chlorinated isoprene rubber, and polybutadiene rubber (both cis and trans).

PM4) Low-crystallinity propylene/olefin copolymers, preferably random copolymers, comprising:
i) at least 70 wt % propylene;
ii) 5 to 30 wt % (preferably 5 to 20 wt %) of comonomer selected from ethylene and $C_4$ to $C_{12}$ olefins (preferably selected from ethylene, butene, and hexene; preferably ethylene); preferably made using a metallocene-type catalyst; and having one or more of the following properties:
  a) $M_w$ of 20 to 5,000 kg/mol (preferably 30 to 2,000 kg/mol, preferably 40 to 1,000 kg/mol, preferably 50 to 500 kg/mol, preferably 60 to 400 kg/mol); and/or
  b) molecular weight distribution index ($M_w/M_n$) of 1.5 to 10 (preferably 1.7 to 5, preferably 1.8 to 3); and/or
  c) GPC-determined g' index value of 0.9 or greater (preferably 0.95 or greater, preferably 0.99 or greater); and/or
  d) density of 0.85 to about 0.90 g/cm$^3$ (preferably 0.855 to 0.89 g/cm$^3$, preferably 0.86 to about 0.88 g/cm$^3$); and/or
  e) melt flow rate (MFR) of at least 0.2 dg/min (preferably 1-500 dg/min, preferably 2-300 dg/min); and/or
  f) heat of fusion ($H_f$) of 0.5 J/g or more (preferably 1 J/g or more, preferably 2.5 J/g or more, preferably 5 J/g or more) but less than or equal to 75 J/g (preferably less than or equal to 50 J/g, preferably less than or equal to 35 J/g, preferably less than or equal to 25 J/g); and/or
  g) DSC-determined crystallinity of from 1 to 30 wt % (preferably 2 to 25 wt %, preferably 2 to 20 wt %, preferably 3 to 15 wt %); and/or
  h) a single broad melting transition with a peak melting point of 25° C. to about 105° C. (preferably 25° C. to 85° C., preferably 30° C. to 70° C., preferably 30° C. to 60° C.), where the highest peak considered the melting point; and/or
  i) crystallization temperature ($T_c$) of 90° C. or less (preferably 60° C. or less); and/or
  j) greater than 80% of the propylene residues (exclusive of any other monomer such as ethylene) arranged as 1,2 insertions with the same stereochemical orientation of the pendant methyl groups, either meso or racemic, as determined by $^{13}$C NMR; and/or
  k) $^{13}$C NMR-determined propylene tacticity index of more than 1; and/or
  l) $^{13}$C NMR-determined mm triad tacticity index of 75% or greater (preferably 80% or greater, preferably 82% or greater, preferably 85% or greater, preferably 90% or greater).

Useful low-crystallinity propylene/olefin copolymers are available from ExxonMobil Chemical; suitable examples include Vistamaxx™ 6100, Vistamaxx™ 6200 and Vistamaxx™ 3000. Other useful low-crystallinity propylene/olefin copolymers are described in WO 03/040095, WO 03/040201, WO 03/040233, and WO 03/040442, all to Dow Chemical, which disclose propylene-ethylene copolymers made with non-metallocene catalyst compounds. Still other useful low-crystallinity propylene/olefin copolymers are described in U.S. Pat. No. 5,504,172 to Mitsui Petrochemical. Preferred low-crystallinity propylene/olefin copolymers are described in U.S. Published Application No. 2002/0004575 to ExxonMobil Chemical.

PM5) Propylene oligomers suitable for adhesive applications, such as those described in WO 2004/046214, particular those at pages 8 to 23.

PM6) Olefin block copolymers, including those described in WO 2005/090425, WO 2005/090426, and WO 2005/090427.

PM7) Polyolefins that have been post-reactor functionalized with maleic anhydride (so-called maleated polyolefins), including maleated ethylene polymers, maleated EP Rubbers, and maleated propylene polymers. Preferably, the amount of free acid groups present in the maleated polyolefin is less than about 1000 ppm (preferably less than about 500 ppm, preferably less than about 100 ppm), and the amount of phosphite present in the maleated polyolefin is less than 100 ppm.

PM8) Styrenic Block Copolymers (SBCs), including (but not limited to):
Unhydrogenated SBCs such as SI, SIS, SB, SBS, SIBS and the like, where S=styrene, I=isobutylene, and B=butadiene; and hydrogenated SBCs, such as SEBS, where EB=ethylene/butene.

PM9) Engineering Thermoplastics, including (but are not limited to):
Polycarbonates, such as poly(bisphenol-a carbonate); polyamide resins, such as nylon 6 (N6), nylon 66 (N66), nylon 46 (N46), nylon 11 (N11), nylon 12 (N12), nylon 610 (N610), nylon 612 (N612), nylon 6/66 copolymer (N6/66), nylon 6/66/610 (N6/66/610), nylon MXD6 (MXD6), nylon 6T (N6T), nylon 6/6T copolymer, nylon 66/PP copolymer, and nylon 66/PPS copolymer; polyester resins, such as polybutylene terephthalate (PBT), polyethylene terephthalate (PET), polyethylene isophthalate (PEI), PET/PEI copolymer, polyacrylate (PAR), polybutylene naphthalate (PBN), liquid crystal polyester, polyoxalkylene diimide diacid/polybutyrate terephthalate copolymer, and other aromatic polyesters; nitrile resins, such as polyacrylonitrile (PAN), polymethacrylonitrile, styrene-acrylonitrile copolymers (SAN), methacrylonitrile-styrene copolymers, and methacrylonitrile-styrene-butadiene copolymers; acrylate resins, such as polymethyl methacrylate and polyethylacrylate; polyvinyl acetate (PVAc); polyvinyl alcohol (PVA); chloride resins, such as polyvinylidene chloride (PVDC), and polyvinyl chloride (PVC); fluoride resins, such as polyvinylidene fluoride (PVDF), polyvinyl fluoride (PVF), polychlorofluoroethylene (PCFE), and polytetrafluoroethylene (PTFE); cellulose resins, such as cellulose acetate and cellulose acetate butyrate; polyimide resins, including aromatic polyimides; polysulfones; polyacetals; polylactones; polyketones, including aromatic polyketones; polyphenylene oxide; polyphenylene sulfide; styrene resins, including polystyrene, styrene-maleic anhydride copolymers, and acrylonitrile-butadiene-styrene resin.

PM10) EP Rubbers, including copolymers of ethylene and propylene, and optionally one or more diene monomer(s), where the ethylene content is from 35 to 85 mol %, the total diene content is 0 to 5 mol %, and the balance is propylene with a minimum propylene content of 15 mol %. Typically the EP Rubbers have a density of less than 0.86 g/cc.

Applications

The hydrosilane-functionalized polyolefins of this invention (and blends thereof as described above) may be used in any known thermoplastic or elastomer application. Examples include uses in molded parts, films, tapes, sheets, tubing, hose, sheeting, wire and cable coating, adhesives, shoe soles, bumpers, gaskets, bellows, films, fibers, elastic fibers, nonwovens, spun bonds, corrosion protection coatings and sealants. Preferred uses include additives for lubricants and/or fuels.

This invention further relates to:

1. A hydrosilane-functionalized polyolefin represented by the formula: PO—Si(R*)$_m$H$_n$, PO—Si(R*)$_2$H, or PO—Si(R*)$_2$- L-Si(R**)$_2$H, wherein m is 1 or 2; n is 1 or 2; m+n=3; PO is substituted or unsubstituted hydrocarbyl group having from 20 to about 10,000 carbon atoms; each R*, independently, is a H, or a $C_1$ to a $C_{20}$ substituted or unsubstituted hydrocarbyl group, where any two R* may form a cyclic structure with Si; L is a bond or a linking group; and each R, independently, is a H, or a $C_1$ to a $C_{20}$ substituted or unsubstituted hydrocarbyl group, where any two R may form a cyclic structure with Si.

2. The hydrosilane-functionalized polyolefin of paragraph 1, wherein at least one R* is H or methyl, ethyl, propyl, butyl, pentyl, hexyl, heptyl, octyl, nonyl, decyl undecyl, dodecyl, phenyl, substituted phenyl (such as alkyl substituted phenyl, such as C1 to C12 alkyl substituted phenyl, such as methyl substituted phenyl), preferably hydrogen, phenyl group or a methyl group.

3. The hydrosilane-functionalized polyolefin of paragraph 1 or 2, wherein PO is substituted or unsubstituted eicosene.

4. The hydrosilane-functionalized polyolefin of any of paragraphs 1 through 3, wherein PO has 100 to 10,000 carbon atoms, preferably 500 to 10,000, preferably 1000 to 10,000, preferably 5000 to 10,000 carbon atoms.

5. The hydrosilane-functionalized polyolefin of any of paragraphs 1 through 4, wherein L is an oxygen, a substituted or unsubstituted hydrocarbyl group, or a substituted or unsubstituted hydrocarbyl containing ether group.

6. The hydrosilane-functionalized polyolefin of any of paragraphs 1 to 5, wherein at least one R** is H or methyl, ethyl, propyl, butyl, pentyl, hexyl, heptyl, octyl, nonyl, decyl undecyl, dodecyl, phenyl, substituted phenyl (such as alkyl substituted phenyl, such as C1 to C12 alkyl substituted phenyl, such as methyl substituted phenyl), preferably hydrogen, phenyl group or a methyl group.

7. The hydrosilane-functionalized polyolefin of any of paragraphs 1 to 6, wherein L is $C_1$ to a $C_{12}$ substituted or unsubstituted hydrocarbyl containing ether group, preferably a $C_2$ to $C_{12}$ substituted or unsubstituted hydrocarbyl containing ether group, preferably L is —CH$_2$OCH$_2$—, —CH$_2$CH$_2$—O—CH$_2$CH$_2$—, —CH$_2$CH$_2$CH$_2$—O—CH$_2$CH$_2$CH$_2$—, or —C$_6$H$_4$—O—C$_6$H$_4$—.

8. The hydrosilane-functionalized polyolefin of any of paragraphs 1 to 7, where the vinyl terminated polyolefin is any of the vinyl terminated polyolefins described herein above or below.

9. The hydrosilane-functionalized polyolefin of any of paragraphs 1 to 8, wherein the hydrosilane-functionalized polyolefin has an Mn of 100 to 100,000 g/mol.

10. The hydrosilane-functionalized polyolefin of any of paragraphs 1 to 9, wherein the hydrosilane-functionalized polyolefin comprises at least 50 mol % propylene.

11. A process to produce a hydrosilane-functionalized polyolefin such as the hydrosilane-functionalized polyolefin of paragraphs 1 to 10, comprising contacting a metallocene, a hydrosilylation reagent, optionally a reducing agent, and one or more vinyl terminated polyolefins, wherein the metallocene is represented by the formula: TnCp$_2$MX$_2$, T is a bridging group; n is 0 or 1; each Cp is, independently, a substituted or unsubstituted cyclopentadienyl ring; M is Zr, Ti, or Hf, preferably Zr; each X is, independently, selected from the group consisting of hydrocarbyl radicals having from 1 to 20 carbon atoms, hydrides, amides, alkoxides, sulfides, phosphides, halogens, dienes, amines, phosphines, ethers, or a combination thereof; wherein the hydrosilylation agent is represented by the formula: $Si(R^*)_mH_n$, or $Si(R^*)_rH_sLSi(R^{**})_pH_q$, m=1 or 2, n=2 or 3; m+n=4; each $R^*$, independently, is a H, or a C1 to a C20 substituted or unsubstituted hydrocarbyl group, where any two $R^*$ may form a cyclic structure with Si, r=0 or 1; s=2 or 3; r+s=3; p=0 or 1; q=2 or 3; p+q=3; L is a bond or a linking group; each $R^{}$, independently, is a H, or a $C_1$ to a $C_{20}$ substituted or unsubstituted hydrocarbyl group, where any two $R^{}$ may form a cyclic structure with Si; and the vinyl terminated polyolefin is substituted or unsubstituted hydrocarbyl group having from 20 to about 10,000 carbon atoms and having at least 5% allyl chain ends; and obtaining a hydrosilane-functionalized polyolefin such as the hydrosilane-functionalized polyolefin of paragraphs 1 to 10.

12. A process to functionalize polyolefins comprising contacting a metallocene, a hydrosilylation reagent, optionally a reducing agent, and one or more vinyl terminated polyolefins, wherein the metallocene is represented by the formula: $TnCp_2MX_2$, T is a bridging group; n is 0 or 1; each Cp is, independently, a substituted or unsubstituted cyclopentadienyl ring; M is Zr, Ti, or Hf (preferably Zr); each X is, independently, selected from the group consisting of hydrocarbyl radicals having from 1 to 20 carbon atoms, hydrides, amides, alkoxides, sulfides, phosphides, halogens, dienes, amines, phosphines, ethers, or a combination thereof; wherein the hydrosilylation agent is represented by the formula: $Si(R^*)_mH_n$, or $Si(R^*)_rH_sLSi(R^{**})_pH_q$, m=1 or 2, n=2 or 3; m+n=4; each $R^*$, independently, is a H, or a $C_1$ to a $C_{20}$ substituted or unsubstituted hydrocarbyl group, where any two $R^*$ may form a cyclic structure with Si, r=0 or 1; s=2 or 3; r+s=3; p=0 or 1; q=2 or 3; p+q=3; L is a bond or a linking group; each $R^{}$, independently, is a H, or a $C_1$ to a $C_{20}$ substituted or unsubstituted hydrocarbyl group, where any two $R^{}$ may form a cyclic structure with Si; and the vinyl terminated polyolefin is substituted or unsubstituted hydrocarbyl group having from 20 to about 10,000 carbon atoms, preferably having at least 5% allyl chain ends.

13. The process of paragraph 11 or 12, wherein n is 0 and at least one position on the Cp ring is hydrogen, alternately at least two positions on the Cp ring are hydrogen, alternately at least three positions on the Cp ring are hydrogen, alternately at least four positions on the Cp ring are hydrogen, alternately five positions on the Cp ring are hydrogen.

14. The process of paragraph 11 or 12, wherein n is 0 and the Cp ring is an indene and at least one position on the indene is hydrogen, alternately at least two positions on the indene are hydrogen, alternately at least three positions on the indene are hydrogen, alternately at least four positions on the indene are hydrogen, alternately at least five positions on the indene are hydrogen, alternately at least six positions on the indene are hydrogen, alternately seven positions on the indene are hydrogen.

15. The process of any of paragraphs 11 to 15, wherein the metallocene is one or more of $T_n(CpMe)_2MX_2$, $T_n(CpPrMe)_2MX_2$, $T_n(CpBuMe)_2MX_2$, $T_n(Cpn-Pr)_2MX_2$, $T_n(Cpt-Bu)_2MX_2$, $T_n(CpSiMe_3)_2MX_2$, $T_n(Indenyl)(Cp)MX_2$, $T_n(Fluorenyl)(Cp)MX_2$, wherein: each Cp is, independently, a substituted or unsubstituted cyclopentadienyl ring; T is a bridging group; n is 0 or 1; M is Zr, Ti, or Hf; each X is, independently, selected from the group consisting of hydrocarbyl radicals having from 1 to 20 carbon atoms, hydrides, amides, alkoxides, sulfides, phosphides, halogens, dienes, amines, phosphines, ethers, or a combination thereof; Pr is propyl, Me is methyl, Bu is butyl, and n-Pr is n-propyl.

16. The process of paragraph 15, wherein n is zero.

17. The process of paragraph 15, wherein n is one and T is $Me_2Si$, $CR^*_2$, $Et_2Si$, or $CH_2CH_2$, wherein $R^*$ is a hydrocarbyl group, Me is methyl, and Et is ethyl.

18. The process of any of paragraphs 11 to 17, wherein the hydrosilylation reagent is one or more of the reagents represented by the formulae:

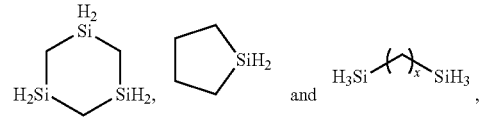

wherein x is a number from 1 to 40, or the hydrosilylation reagent is one or more of $PhMeSiH_2$, $Ph_2SiH_2$, n-hexylSiH$_3$, allyldimethoxysilane, allylsilane, allylmethylsilane, benzylsilane, benzylmethylsilane, bicycloheptenyl)ethyl]methylsilane, bicycloheptenyl)ethyl]silane, 5-(bicycloheptenyl)methylsilane, 5-(bicycloheptenyl)silane, 2-(bicycloheptyl) silane', 1,4-bis(methylsilyl)benzene, 1,4-bis(methylsilyl)butane, 1,2-bis(methylsilyl)ethane bis(nonafluorohexyl)silane, $SiH_3(CH_2)_2SiH_3$, $SiH_3(CH_2)_6SiH_3$, $SiH_3(CH_2)_{16}SiH_3$, $SiH_3(CH_2)_8SiH_3$, $SiH_3(CH_2)_3SiH_3$, $SiH_3(CH_2)_{10}SiH_3$, $SiH_3(CH_2)SiH_3$, ortho, meta or para-$SiH_3(C_6H_4)_2SiH_3$, bis(trimethylsilylmethyl)silane, butenylmethylsilane, t-butylsilane, n-butylmethylsilane, t-butylmethylsilane, p-(t-butyl)phenethylsilane, t-butylphenylsilane, n-butylsilane, (p-chloromethyl)phenylsilane, [2-(3-cyclohexenyl)ethyl]methylsilane, [2-(3-cyclohexenyl)ethyl] silane, 3-cyclohexenylsilane, cyclohexylmethylsilane, cyclooctylsilane, cyclopentylsilane, n-decylsilane, n-decylmethylsilane, di(t-butylamino)silane, di-t-butylsilane, dicyclopentylsilane, diethylsilane, di-n-hexylsilane, diisopropylsilane, dimesitylsilane, (3,3-dimethylbutyl)silane, dimethylsilane, di-n-octylsilane, diphenylsilane, 1,3-disilabutane, 1,4-disilabutane, disilane, 1,3-disilapropane, di(p-tolyl))silane, docosylsilane, dodecylsilane, eicosylsilane, ethylsilane, ethylmethylsilane, n-heptylmethylsilane, n-heptylsilane, hexylsilane, isobutylsilane, isooctylsilane, isopropylmethylsilane, isopropylsilane, methylsilane, p-(methylphenethyl)methylsilane, (1-naphthylmethyl)silane, n-octadecylmethylsilane, n-octadecylsilane, n-octylsilane, n-octylmethylsilane, pentafluorophenylpropylmethylsilane, pentafluorophenylpropylsilane, pentylsilane, n-pentylmethylsilane, phenylethylsilane, 6-phenylhexylsilane, phenylmethylsilane, 1-phenyl-1-(methyl,4-sila)butane, phenylsilane, n-propylsilane, p-tolylsilane, p-tolylmethylsilane, 1,3,5-trisilacyclohexane, trisilane, 10-undecenylsilane, and the like.

19. The process of any of paragraphs 11 to 18, wherein the reducing agent is present and is one or more of n-BuLi, t-BuLi, EtMgCl, Na, Li, Mg, K, LiH, LiBEt$_3$H, NaBH$_4$, LiAlH$_4$, sec-BuLi, (nBu)$_2$Mg, MeLi, and $R^*ZnX^*$, wherein $X^*$ is a leaving group, $R^*$ is a hydrocarbyl group, Bu is butyl, Et is ethyl, Me is methyl.

20. The process of any of paragraphs 11 to 19, wherein the wherein the vinyl terminated polyolefin has at least 60% allyl chain ends.

21. The process of any of paragraphs 11 to 20, wherein the vinyl terminated polyolefin has at least 70% allyl chain ends and is a polymer comprising propylene and/or ethylene.

22. The process of any of paragraphs 10 to 21, wherein the vinyl terminated polyolefin has an Mn of from 200 to 60,000 g/mol.
23. The process of any of paragraphs 11 to 22, wherein the vinyl terminated polyolefin comprises propylene and at least 10 mol % of a $C_4$ or greater olefin and has: 1) at least 30% allyl chain ends (relative to total unsaturations); and 2) an Mn of from 200 to 60,000 g/mol, preferably from 200 to 50,000 g/mol, preferably from 500 to 40,000 g/mol.
24. The process of paragraph 23, wherein where in the $C_4$ or greater olefin is a $C_5$ to $C_{40}$ alpha olefin.
25. The process of any of paragraphs 11 to 24, wherein the vinyl terminated polyolefin has an Mn of at least 200 g/mol and comprises one or more $C_4$ to $C_{40}$ olefin derived units, where the vinyl terminated polyolefin comprises substantially no propylene derived units; and wherein the vinyl terminated polyolefin has at least 5% allyl chain ends, relative to total unsaturations.
26. The process of any of paragraphs 11 to 25, wherein the vinyl terminated polyolefin has an allyl chain end to vinylidene chain end ratio of greater than 2:1 and/or an allyl chain end to vinylene chain end ratio of greater than 10:1.
27. The process of any of paragraphs 11 to 26, where the vinyl terminated polyolefin is any of the vinyl terminated polyolefins described herein above or below.

EXAMPLES

Tests and Materials

Products were characterized by $^1$H NMR as follows:
$^1$H NMR data was collected at either room temperature or 120° C. (for purposes of the claims, 120° C. shall be used) in a 5 mm probe using a Varian spectrometer with a $^1$Hydrogen frequency of at least 400 MHz or a Bruker 500 MHz. Data was recorded using a maximum pulse width of 45°, 8 seconds between pulses and signal averaging 120 transients. Spectral signals were integrated and the number of unsaturation types per 1000 carbons was calculated by multiplying the different groups by 1000 and dividing the result by the total number of carbons. $M_n$ of the macromer is determined by $^1$H NMR spectroscopy by comparison of integrals of the aliphatic region to the olefin region as determined using the protocol described in the Experimental section of U.S. Ser. No. 12/143,663, filed on Jun. 20, 2008.

For the hydrosilylated products $^1$H NMR were collected in the same manner but Mn was not calculated by NMR when some products still contained unreacted vinylidene and other unreacted unsaturated groups. In these cases, the best comparison was Mn of starting macromer to Mn of hydrosilylated product. In most cases, Mn is higher in the silylated product because of work-up procedure. Low MW products were washed away from the solid products in the PE and iPP examples and are more comparable in the EP product that was worked up differently.

GPC conditions are those described above.

All molecular weights are number average unless otherwise noted. All molecular weights are reported in g/mol, unless otherwise noted.

The following abbreviations are used in the Examples:
aPP is atactic polypropylene, iPP is isotactic polypropylene, EP is ethylene-propylene copolymer, TCE is 1,1,2,2-tetrachloroethane, h is hours, min is minutes. The vinyl-terminated polyolefins listed in Table 1 were prepared according to procedures described in WO 2009/155471 (U.S. Ser. No. 12/143,663, filed on Jun. 20, 2008).

Discussion

Eicosene (also referred to as macromer A), a $C_{20}$ alpha-olefin was cleanly hydrosilylated with $PhMeSiH_2$ using $Cp_2ZrMe_2/nBuLi$ catalyst in toluene at 90° C. The reaction was complete in 2 or less hours and gave high yields of the anti-Markovnikov product or α-silane as determined by $^1$H NMR. The spectrum is shown in FIG. 1. The Si—H resonance at δ 4.59 (J=3.6 Hz) is a sextet as expected from the α-silane product; the β-silane Si—H resonance would be a pentad. Other characteristic resonances occur at δ (ppm) 0.26 (Si-Me, d, J=3.8 Hz), a slightly resolved triplet at 0.89 (methyl end group, 3H, J=7.1 Hz) and a complex multiplet at 0.78 attributable to the Si—$CH_2$— group. The spectrum also shows additional resonances attributable to the silane coupling by-product $H(SiPhMe)_xH$ at δ (ppm) 0.2 to 0.4, 4.68, and in the aromatic region (7.5 to 7.0) which interferes with integration of the major product 1. (See Scheme 1.)

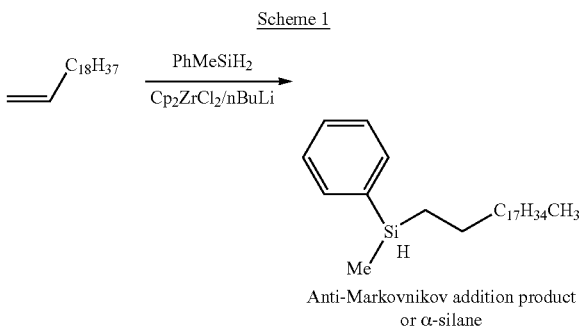

Scheme 1

Anti-Markovnikov addition product or α-silane

An EP macromer B (54% ethylene), produced in a continuous solution polymerization according to the methods generally described in WO 2009/155474, with high levels of vinyl chain ends was also hydrosilylated in a similar manner to yield 2. The reaction was complete in 2 hours and gave high yields of α-silane 2. Due to the overlapping peaks in the proton spectrum it was not possible to determine the regiochemistry of Si—H addition. The most likely product is the anti-Markovnikov silane shown in Scheme 2. The $^1$H NMR spectrum did not exhibit two distinct types of silylated ends as a result of the identity of the penultimate group adjacent to the original vinyl group, propylene or ethylene. Two types of vinyl chain ends were resolved in the original spectrum of macromer B for this reason.

Scheme 2

2; R = Me, R' = Ph
3; R = R' = Ph

The hydrosilylation of a homopolyethylene PE macromer C (produced using silica supported 2,6 bis[1-(2-benzylphenylimine)ethyl]pyridine iron dichloride in gas phase according to the general methods described in U.S. Patent Publication No. 2009/0088542) was performed using $Cp_2ZrMe_2$ and $Ph_2SiH_2$. The reaction was monitored periodically and was slow, even longer than the reaction to synthesize 4. (See Scheme 3) The proton spectrum indicated the silane displayed as the a-silane with characteristic resonances.

Scheme 3

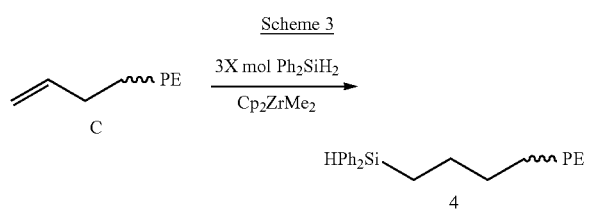

The EP macromer B was hydrosilylated with Ph$_2$SiH$_2$ as well using Cp$_2$ZrMe$_2$ in toluene at 90° C. to yield 3 (see Scheme 2). The reaction was complete after 23 hours using an excess of Ph$_2$SiH$_2$ to yield 3 as major product with regiochemistry assigned as shown in Scheme 2. In addition, the crude reaction contained both unreacted Ph$_2$SiH$_2$ as well as some silane coupled product, H(SiPh$_2$)xH. Much longer reaction times were required for complete conversion due to differences in the species responsible for initiation. The initiating species is postulated to be a d2 intermediate [Cp2Zr] which undergoes oxidative addition of R$_3$Si—H to yield Cp$_2$Zr(SiR$_3$)(H). The reaction of Cp$_2$ZrCl$_2$ with nBuLi has been shown to lead to Cp$_2$Zr(nBu)$_2$ which decomposes above 0° C. to ultimately yield d2 intermediates for oxidative additions or d4 species reactive towards sigma bond metathesis.

For comparative purposes, an iPP macromer D having roughly equivalent amounts of vinyl and vinylidene termini was reacted with PhMeSiH$_2$ using the Cp$_2$ZrCl$_2$/nBuLi catalyst. After 1 hour at 120° C., all the vinyl resonances were gone and a characteristic Si—H resonance at 4.4 ppm was present. The vinylidene resonances were still present indicating only vinyl terminated macromer had reacted. The reaction was monitored periodically over 55 hrs. New resonances began to appear after 2 hours whereas the amount of vinylidene terminated iPP decreased somewhat. The new resonances are most likely attributable to silane coupled products generalized by the formula H(SiMePh)xH, since a large excess of PhMeSiH$_2$ to macromer was employed. As the silane coupled product increased the vinylidene population slowly decreased. After 55 hours of reaction time, about 50% of the original vinylidene terminated iPP remained. The reaction product was not identified but most likely is hydrogenated iPP with "H$_2$" being supplied as a byproduct of the silane coupled product. (See Scheme 4.)

Scheme 4

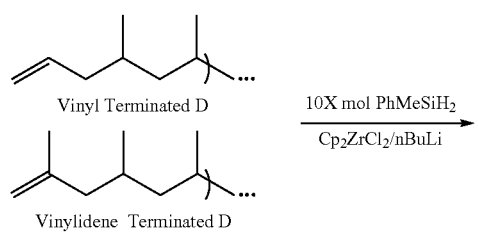

-continued

HMePhSi~~~~~~~~~~
5

Vinylidene Terminated D
Reaction mixture at 1 hr

HMePhSi~~~~~~~~~~
5

Vinylidene Terminated D      ?
Reaction mixture at 55 hr

EXAMPLES

PhMeSiH$_2$, Ph$_2$SiH$_2$, and n-hexylSiH$_3$ were purchased from Gelest. Eicosene (macromer A) was purchased from Aldrich. Anhydrous solvents were purchased from Aldrich and dried further over 3A sieves. Hydrosilylation reactions were performed in the dry box under an N$_2$ atmosphere. Macromers were dried prior to use by dissolving them in toluene and drying with 3A sieves. Solid macromers were dried in a vacuum oven at 70° C. for 12 hrs.

Macromer D was made in a batch reactor: A 2 L stainless autoclave was charged with 0.3 ml of 1.0 M triisobutylaluminum (Aldrich) and 700 mls of isohexanes. Propylene (400 mls) was added and the reactor was heated to 120° C. A catalyst solution was prepared by combining rac-Me$_2$Si(2-Methyl,4-phenylindenyl)$_2$zirconium dimethyl (Boulder Scientific, 10 mg) and [PhNHMe$_2$][B(C$_6$F$_5$)$_4$] (Albemarle, 13.6 mg) in 10 mls toluene. The catalyst solution was stirred at room temperature for 60 minutes. Catalyst solution (2.0 mls of original solution) was put in a catalyst tube and injected into the reactor with high pressure nitrogen. The polymerization was allowed to proceed for 10 minutes and the reactor cooled to room temperature. After the pressure was vented the reactor contents were transferred into a glass container, volatiles removed and the solid product dried in vacuo (70° C., 3 hrs). The yield was 195 g.

Hydrosilylation of Eicosene (Macromer A) with PhMeSiH$_2$, 1

Cp$_2$ZrCl$_2$ (62 mg, 0.21 mmol) in 10 ml of toluene was cooled to −30° C. nBuLi (0.2 ml, 0.42 mmol, 2.5 M in hexanes) was added to the reaction mixture and the mixture warmed to 0° C. PhMeSiH$_2$ (1.01 g, 8.3 mmol), dissolved in 10 ml toluene, was added next followed by 1-eicosene (2.05 g, 7.3 mmol), dissolved in 30 ml toluene. The reaction mixture was heated to 90° C. for 4 hours. After two hours the dark brown solution turned a dark reddish color. $^1$H NMR showed 100% conversion. The solution was cooled overnight. Hexane (20 ml) was added and the solution filtered through Celite, the Celite was washed with additional hexane, and combined filtrates reduced to a red oil (2.0 g, 68% yield).

Hydrosilylation of EP Macromer B with PhMeSiH$_2$, 2

PhMeSiH$_2$ (1.0 g, 8.3 mmol) in 10 ml toluene was added to a solution of EP macromer B (10.6 g, 7.4 mmol) in 30 ml toluene. Cp$_2$ZrCl$_2$ (62 mg, 0.21 mmol) in 10 ml of toluene was cooled to −30° C. and reacted with nBuLi (0.2 ml, 0.42 mmol, 2.5 M in hexane). The metallocene solution was warmed to 0° C. and then added to the macromer solution. The reaction mixture was heated to 90° C. for 5 hours. After two hours the dark brown solution turned a dark reddish color. $^1$H NMR showed 100% conversion. The solution was cooled overnight. Hexane (20 ml) was added and the solution filtered through Celite and the Celite was washed with additional hexane. The combined filtrates were reduced under $N_2$ flow to yield a brown viscous oil (8.72 g, 77% yield).

Hydrosilylation of EP Macromer B with $Ph_2SiH_2$, 3

$Ph_2SiH_2$ (1.04 g, 5.6 mmol) was dissolved in 30 ml toluene and added to a solution of 5.0 g EP vinyl macromer B (2200 g/mol, 2.3 mmol) in 30 ml toluene (previously dried over 3A sieves for 3 days). $Cp_2ZrMe_2$ (25 mg, 0.1 mmol) was added as a solid and the reaction heated to 90° C. The reaction was monitored at 1.5 and 23 hrs by $^1$H NMR. At 1.5 hrs conversion to the silane 3 was about 5% and at 23 hrs the conversion was 100%. After 23 hrs the reaction was cooled, stripped of volatiles and the product was washed with acetone (2×100 ml). The oily product was dried in a vacuum oven. A colorless amorphous product was obtained (3.2 g).

Hydrosilylation of PE Macromer C with $Ph_2SiH_2$, 4

PE macromer C (14.3 g, 8.8 mmol) was slurried in toluene (80 ml). $Ph_2SiH_2$ (4.3 g, 23.4 mmol) was added to the reaction mixture and all were heated to 100° C. $Cp_2ZrMe_2$ (25 mg, 0.1 mmol) was added and the reaction mixture heated to 120° C. A 3 hr aliquot analyzed by $^1$H NMR showed about 10% conversion. An aliquot at 21 hrs indicated the reaction was about 50% complete. The reaction was continued for 72 hrs at which time the color was a deep purple. $^1$H NMR analysis indicated all vinyl termini had reacted. The reaction mixture was cooled, acetone (100 ml) was added and the solid filtered. The product was dried in a vacuum oven for 3 hrs at 70° C. (12.9 g). (See Scheme 3.)

Hydrosilylation of iPP Macromer D with $PhMeSiH_2$, 5 iPP Macromer D (14.3 g, 2.4 mmol) containing a 46/52 mixture of vinyl/vinylidene termini was dried in a vacuum oven for 12 hours at 70° C. The dried iPP macromer and $PhMeSiH_2$ (3.6 g, 29.5 mmol) was slurried in 120 ml toluene. $Cp_2ZrCl_2$ (30 mg) was added to a pre-cooled (−20° C.) mixture of nBuLi (120 mg, 1.6 M, hexanes) in 20 ml toluene. The catalyst mixture was stirred and warmed to RT. The catalyst mixture was added to the toluene slurry containing iPP macromer and the reaction mixture heated to 120° C. Aliquots (0.5 ml) were transferred to a glass vial and dried in a vacuum oven for 1 hour prior to analysis. The reaction was cooled after 55 hrs and filtered over a medium glass frit. The solid material was washed with acetone (3×60 ml) and dried in a vacuum oven at 70° C. for 3 hours (13.4 g).

Hydrosilylation of EP Macromer B with n-hexylSiH$_3$, 6 n-hexylSiH$_3$ (1.7 g, 14.6 mmol) and a solution of EP macromer B (3.7 g, 2.6 mmol) in 30 ml toluene were combined and stirred at room temperature. $Cp_2ZrCl_2$ (25 mg) in 10 ml of toluene was cooled to −30° C. and reacted with nBuLi (110 mg, 2.5 M in hexane). The metallocene solution was warmed to 0° C. and then added to the macromer solution. The reaction mixture was heated to 90° C. for 0.5 hours. $^1$H NMR analysis indicated all vinyls were absent. The solution was cooled and the oily product washed with acetone (3×30 mls). The product was dried in vacuo at 70° C. for 48 hrs (2.8 g). $^1$H NMR ($C_6D_6$) δ ppm; 3.9 (m) $SiH_2$ (2H), 2.0 to 0.8 (m) EP aliphatics, 198.3H.

TABLE 1

Macromers used for Hydrosilylation Reactions

| Macromer | Composition | Mw$^a$ | Mn$^a$ | Mw$^a$/Mn$^a$ | Mn $^1$H NMR | % Vinyl | % Vinylidene | % Others |
|---|---|---|---|---|---|---|---|---|
| A | $C_{20}$ α-olefin | | | | | 100 | 0 | 0 |
| B | EP | 5127 | 1416 | 3.6 | 2198 | 96 | 2 | 2 |
| C | PE | 24,510 | 827 | 30 | 2321 | 86 | 0 | 14 |
| D | iPP | 18,218 | 4914 | 3.7 | 5983 | 46 | 52 | 2 |

$^a$determined by GPC-DRI.

TABLE 2

Products from Hydrosilylation Reactions Using $Cp_2ZrCl_2$/nBuLi or $Cp_2ZrMe_2$

| Starting Macromer | Silane | Catalyst | Reaction time, hrs | Product | Mw$^a$ kg/mol | Mn$^b$ kg/mol | Mw/Mn |
|---|---|---|---|---|---|---|---|
| A | $PhMeSiH_2$ | $Cp_2ZrCl_2$/nBuLi | 2 | 1 | — | — | — |
| B | $PhMeSiH_2$ | $Cp_2ZrCl_2$/nBuLi | 2 | 2 | 4.2 | 1.7 | 2.4 |
| B | $Ph_2SiH_2$ | $Cp_2ZrMe_2$ | 23 | 3 | — | — | — |
| C | $Ph_2SiH_2$ | $Cp_2ZrMe_2$ | 72 | 4 | 21.9 | 2.2 | 9.8 |
| D | $PhMeSiH_2$ | $Cp_2ZrCl_2$/nBuLi | 1$^a$ | 5 | 16.6 | 7.2 | 2.3 |
| B | hexylSiH$_3$ | $Cp_2ZrCl_2$/nBuLi | 0.5 | 6 | | 1.4 | |

$^a$determined by GPC-DRI,
$^b$calculated by the $^1$H NMR of the product.

All documents described herein are incorporated by reference herein for purposes of all jurisdictions where such practice is allowed, including any priority documents, related applications and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A hydrosilane-functionalized polyolefin represented by the formula:

PO—Si(R*)$_2$-L-Si(R**)$_2$H; wherein PO is a substituted or unsubstituted eicosanyl or a homopolymer, homo-oligomer, copolymer or co-oligomer consisting of any one or combination of ethylene, propylene, butene, pentene, hexene, octene, nonene, decene, and dodecene; L is a substituted or unsubstituted hydrocarbyl group; each R*, independently, is a H, or a C$_1$ to a C$_{20}$ substituted or unsubstituted hydrocarbyl group, where any two R* may form a cyclic structure with Si; and each R, independently, is a H, or a C$_1$ to a C$_{20}$ substituted or unsubstituted hydrocarbyl group, where any two R may form a cyclic structure with Si.

2. The hydrosilane-functionalized polyolefin of claim 1, wherein one R* is a hydrogen, a phenyl group, hexyl group or a methyl group.

3. The hydrosilane-functionalized polyolefin of claim 1, wherein PO has at least 1000 carbon atoms.

4. The hydrosilane-functionalized polyolefin of claim 1, wherein PO has at least 5000 carbon atoms.

5. The hydrosilane-functionalized polyolefin of claim 1, wherein one R** is a hydrogen, a phenyl or methyl group.

* * * * *